US010717785B2

(12) United States Patent
Hack et al.

(10) Patent No.: US 10,717,785 B2
(45) Date of Patent: Jul. 21, 2020

(54) BINDING MOLECULES THAT BIND HUMAN COMPLEMENT FACTOR C2 AND USES THEREOF

(71) Applicant: BROTEIO PHARMA B.V., Utrecht (NL)

(72) Inventors: Cornelis Erik Hack, Diemen (NL); Cafer Yildiz, Arnhem (NL); Louis Boon, Badhoevedorp (NL); Petrus Johannes Simons, Hillegom (NL)

(73) Assignee: BROTEIO PHARMA B.V., Utrecht (NL)

( * ) Notice: Subject to any disclaimer, the term of this patent is extended or adjusted under 35 U.S.C. 154(b) by 31 days.

(21) Appl. No.: 15/903,810

(22) Filed: Feb. 23, 2018

(65) Prior Publication Data

US 2018/0319895 A1 Nov. 8, 2018

Related U.S. Application Data

(62) Division of application No. 14/892,850, filed as application No. PCT/NL2014/050327 on May 22, 2014, now Pat. No. 9,944,717.

(30) Foreign Application Priority Data

May 23, 2013 (EP) .................................. 13168941

(51) Int. Cl.
| | | |
|---|---|---|
| C12N 15/00 | (2006.01) | |
| C12N 5/00 | (2006.01) | |
| C07H 21/04 | (2006.01) | |
| C07K 16/00 | (2006.01) | |
| C07K 16/40 | (2006.01) | |
| C07K 16/18 | (2006.01) | |

(52) U.S. Cl.
CPC .............. *C07K 16/40* (2013.01); *C07K 16/18* (2013.01); *C07K 2317/24* (2013.01); *C07K 2317/565* (2013.01); *C07K 2317/76* (2013.01)

(58) Field of Classification Search
None
See application file for complete search history.

(56) References Cited

U.S. PATENT DOCUMENTS 8,221,756 B2 7/2012 Fung et al.

FOREIGN PATENT DOCUMENTS

WO 010 708 18 9/2001

OTHER PUBLICATIONS

Ricklin, et al., "Complement-targeted Therapeutics," Nature Biotechnology, vol. 25, No. 11, Nov. 2007.
Xu, et al., "Contribution of the Complement Control Protein Modules of C2 in C4b Binding Assessed by Analysis of C2/Factor B Chimeras," The Journal of Immunology, 158: 5958-5965, 1997.
Oglesby, et al., "Evidence for a C4b Binding Site on the C2b Domain of C2-1," The Journal of Immunology, 141: 926-931, No. 1, Aug. 1, 1988.
Stenbaek, et al., "Human Component C2: Production and Characterization of Polyclonal and Monoclonal Antibodies against C2," Molecular Immunology, 23: 879-886, No. 8, 1986.
Oglesby, et al., "Probing a C4b-Binding Site(s) on C2b with Murine Monoclonal Antibodies," University of Alabama at Birmingham, Birmingham, AL, no date available.
Heinz, et al., "Monoclonal Antibodies against Components of the Classical Pathway of Complement," Complement Inflamm, 6: 166-174, 1989.
Oglesby, et al., "Radioassays for Quantitation of Intact Complement Proteins C2 and B In Human Serum," Journal of Immunological Methods, 110: 55-62, 1988.
Krishnan, et al., "The Structure of C2b, a Fragment of Complement Component C2 Produced during C3 Convertase Formation," Acta Crystallography, D65: 266-274, 2009.
Jackson, et al., "In Vitro Antibody Maturation," Journal of Immunology, 1995, 154: 3310-3319.
Wong, et al., "Structural Requirements for a Specificity Switch and for Maintenance of Affinity using Mutational Analysis of a Phage-Displayed Anti-Arsonate Antibody of Fab Heavy Chain First Complementarity-Determining Region," Journal of Immunology, 1998, 160: 5990-5997.
EPO, PCT/NL2014/050327, "Search Report," dated Oct. 1, 2014.
Huda, R., et al., "Complement C2 siRNA Mediated Therapy of Myasthenia Gravis in Mice," Journal of Autoimmunity, vol. 42, pp. 94-104, May 1, 2013.
Oglesby, T.J., et al., "Radioassays for Quantitation of Intact Complement Proteins C2 and B in Human Serum," Journal of Immunological Methods, Elsevier Science Publishers B.V., Amsterdam, NL, vol. 110, No. 1, pp. 55-62, May 25, 1988.
Anderson, C.M., et al., "A Monoclonal Antibody Against Human Complement Component C2," Biochemical Society Transactions, Portland Press Ltd, BG, vol. 15, No. 4, pp. 660-661, Jan. 1, 1987.
Stenbaek, E.I., et al., "Human Complement Component C2: Production and Characterization of Polyclonal and Monoclonal Antibodies Against C2," Molecular Immunology, Pergamon, GB, vol. 23, No. 8, pp. 879-886, Aug. 1, 1986.
Heinz, H.P., et al., "Monoclonal Antibodies Against Components of the Classical Pathway of Complement," Complement and Inflammation, Karger Basel, CH, vol. 6, No. 3, pp. 166-174, Jan. 1, 1989.
Paul, W.E., Fundamental Immunology, 3rd Edition, pp. 292-295, under heading "Fv Structure and Diversity in Three Dimensions," 1993.
Rudikoff, S. et al., "Single Amino Acid Substitution Altering Antigen-Binding Specificity," Proc. Natl. Acad. Sci. USA, vol. 79, pp. 1979-1983, Mar. 1982.
Coleman, P.M., Research Immunology, vol. 145, pp. 33-36, 1994.

*Primary Examiner* — Shulamith H Shafer
(74) *Attorney, Agent, or Firm* — Lathrop GPM LLP; James H. Velema, Esq.

(57) ABSTRACT

The invention relates to means and methods that relate to binding molecules that bind human complement factor C2. Specific binding molecules are described with specific C2 activity inhibiting properties. Such binding molecules are useful in the treatment of symptoms of various human diseases among which there is inflammatory disease, neuroinflammatory disease or ischemia-reperfusion (I/R) injury disease.

Figure 1:
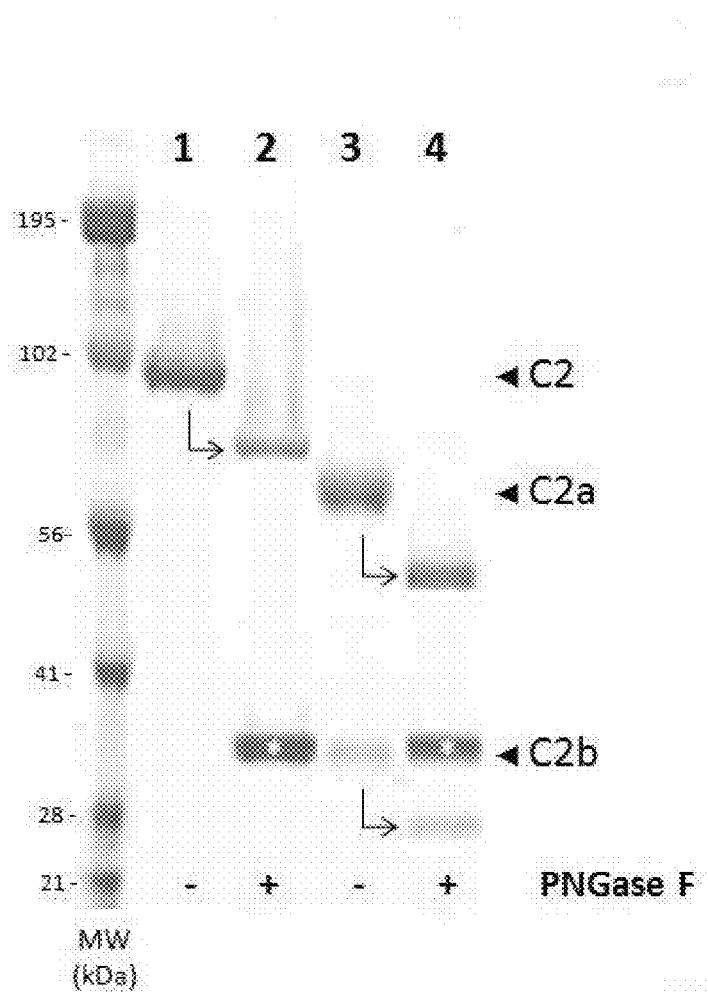

20 Claims, 40 Drawing Sheets
(5 of 40 Drawing Sheet(s) Filed in Color)
Specification includes a Sequence Listing.

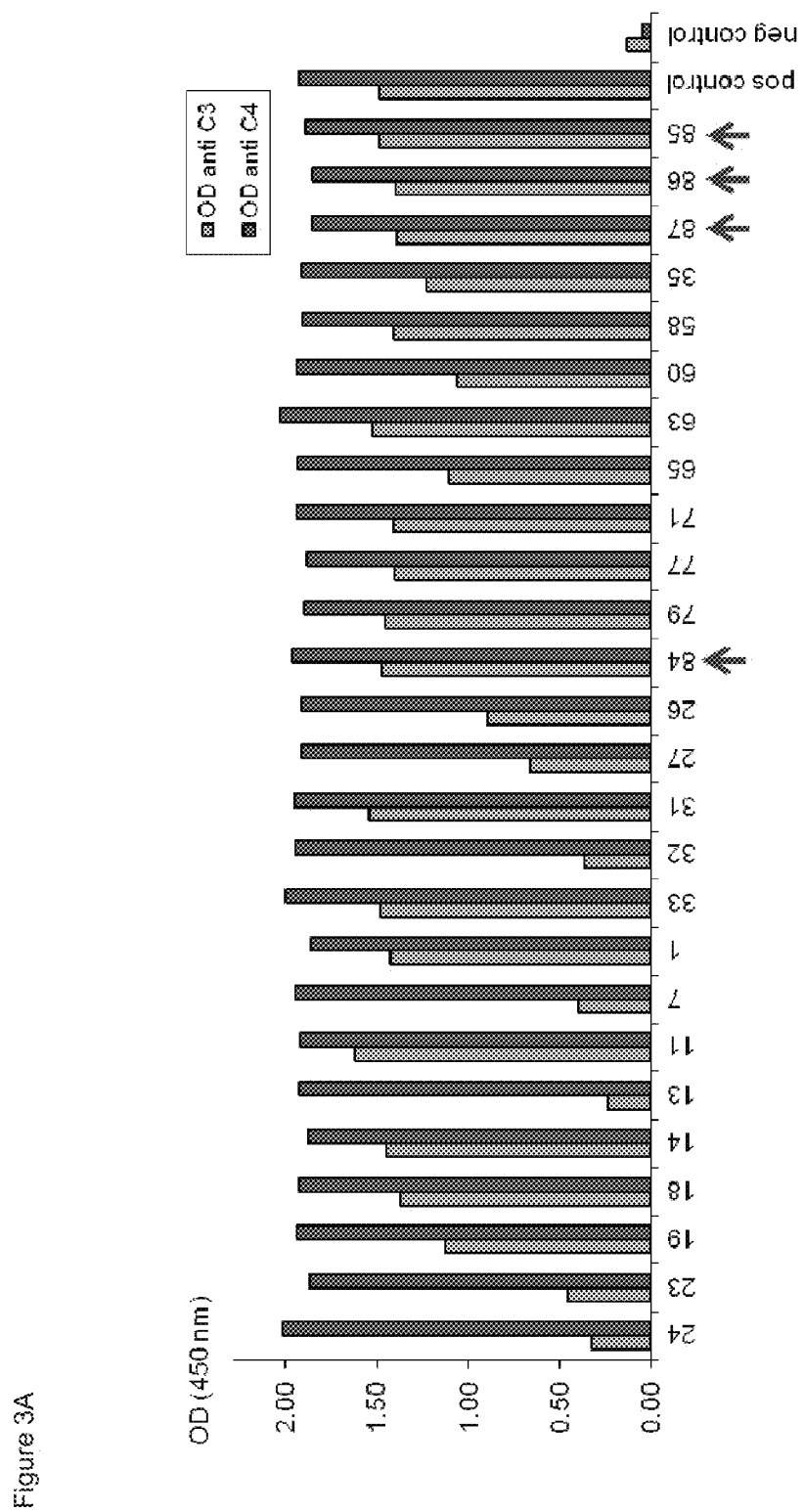

Figure 16A

SEQ ID NO. 1 Amino acid sequence human complement C2 (GenBank accession no. NM_000063; aa 1-752)

```
  1   MGPLMVLFCL LFLYPGLADS APSCPQNVNI SGGTFTLSHG WAPGSLLTYS CPQGLYPSPA
 61   SRLCKSSGQW QTPGATRSLS KAVCKPVRCP APVSFENGIY TPRLGSYPVG GNVSFECEDG
121   FILRGSPVRQ CRPNGMWDGE TAVCDNGAGH CPNPGISLGA VRTGFRFGHG DKVRYRCSSN
181   LVLTGSSERE CQGNGVWSGT EPICRQPYSY DFPEDVAPAL GTSFSHMLGA TNPTQKTKES
241   LGRKIQIQRS GHLNLYLLLD CSQSVSENDF LIPKESASLM VDRIPSFEIN VSVAIITFAS
301   EPKVLMSVLN DNSRDMTEVI SSLENANYKD HENGTGTNTY AALNSVYLMM NNQMRLLGME
361   TMAWQEIRHA IILLTDGKSN MGGSPKTAVD HIREILNINQ KRNDYLDIYA IGVGKLDVDW
421   RELNELGSKK DGERHAFILQ DTKALHQVFE HMLDVSKLTD TICGVGNMSA NASDQERTPW
481   HVTIKPKSQE TCRGALISDQ WVLTAAHCFR DGNDHSLWRV NVGDPKSQWG KEFLIEKAVI
541   SPGFDVFAKK NQGILEFYGD DIALLKLAQK VKMSTHARPI CLPCTMEANL ALRRPQGSTC
601   RDHENELLNK QSVPAHFVAL NGSKLNINLK MGVEWTSCAE VVSQEKTMFP NLTDVREVVT
661   DQFLCSGTQE DESPCKGESG GAVFLERRFR FFQVGLVSWG LYNPCLGSAD KNSRKRAPRS
721   KVPPPRDFHI NLFRMQPWLR QHLGDVLNFL PL
```

*Signal peptide (aa sequence 1-20) is boxed, subcomponent C2b is underlined (aa sequence 21-243), and subcomponent C2a comprises aa sequence 244-752.*

SEQ ID NO. 2 Amino acid sequence of no. 5F2.4 heavy chain variable region
```
  1   EVQLQQSGAE LVKPGASVKI SCKASGYTFT DYNMDWVKQS HGKSLEWIGD INPNYESTGY
 61   NQKFKGKATL TVDKSSSTAY MELRSLTSED TAVYYCARED DHDAFAYWGQ GTLVTVSA
```

SEQ ID NO. 3 Amino acid sequence of no. 5F2.4 light chain variable region
```
  1   DIVLTQSPAS VVVSLGQRAT ISCRASKSVR TSGYNYMHWY QQKPGQPPKL LIYLASNLKS
 61   GVPARFSGSG SGTDFTLNIH PVEEADAATY YCQHSRELPY TFGGGTKLEI KR
```

Complementarity determining regions (CDRs) of mouse anti-human complement C2 antibody no. 5F2.4: SEQ ID NO 4-9

SEQ ID NO. 4 Amino acid sequence of no. 5F2.4 heavy chain CDR1
DYNMD

SEQ ID NO. 5 Amino acid sequence of no. 5F2.4 heavy chain CDR2
DINPNYESTGYNQKFKG

SEQ ID NO. 6 Amino acid sequence of no. 5F2.4 heavy chain CDR3
EDDHDAFAY

SEQ ID NO. 7 Amino acid sequence of no. 5F2.4 light chain CDR1
RASKSVRTSGYNYMH

SEQ ID NO. 8 Amino acid sequence of no. 5F2.4 light chain CDR2
LASNLKS

Figure 16B

SEQ ID NO. 9 Amino acid sequence of no. 5F2.4 light chain CDR3
QHSRELPYT

SEQ ID NO. 10 Amino acid sequence of no. 13 heavy chain variable region
```
  1  QVQLQQPGAE LVKPGASVKL SCKASGYTFT IYYMYWVKQR PGQGLEWIGE VDPSIGGISF
 61  NEKFKSKATL TVDRSSSTAY MHLSSLTSED SAVYYCTRGG TYYAMDYWGQ GTSVTVSS
```

SEQ ID NO. 11
Amino acid sequence of no. 13 light chain variable region
```
  1  DVLMTQTPLS LPVSLGDQAS ISCRAGQSIV HSNGNTYLEW YLQKPGQSPK LLIYKVSNRF
 61  SGVPDRFSGS GSGTDFTLKI SRVEAEDLGV YYCFQGSHVP WTFGGGTKLE IKR
```

Complementarity determining regions (CDRs) of mouse anti-human complement C2 antibody no. 13: SEQ ID NO 12-17

SEQ ID NO. 12 Amino acid sequence of no. 13 heavy chain CDR1
IYYMY

SEQ ID NO. 13 Amino acid sequence of no. 13 heavy chain CDR2
EVDPSIGGISFNEKFKS

SEQ ID NO. 14 Amino acid sequence of no. 13 heavy chain CDR3
GGTYYAMDY

SEQ ID NO. 15 Amino acid sequence of no. 13 light chain CDR1
RAGQSIVHSNGNTYLE

SEQ ID NO. 16 Amino acid sequence of no. 13 light chain CDR2
KVSNRFS

SEQ ID NO. 17 Amino acid sequence of no. 13 light chain CDR3
FQGSHVPWT

SEQ ID NO. 18 Amino acid sequence of no. 32 heavy chain variable region
```
  1  QVQLQQSGAE LVKPGASVKL SCKASGYTFT SYDMYWVKQR PGQGLEWIGE INPSNGDTNF
 61  NEKFKSKATL TVDKSSSTAH MQLSSLTSED SAVYYCTRGG TFYAMDYWGQ GTSVTVSS
```

SEQ ID NO. 19 Amino acid sequence of no. 32 light chain variable region
```
  1  DIQMTQTPLS LPVSLGDQAS ISCRSSQSIV HSNGNTYLEW YLQKPGQSPK LLIYKVSNRF
 61  SGVPDRFSGS GSGTDFTLKI SRVEAEDLGV YYCFQGSHVP WTFGGGTKLE IKR
```

Complementarity determining regions (CDRs) of mouse anti-human complement C2 antibody no. 32: SEQ ID NO 20-25

SEQ ID NO. 20 Amino acid sequence of no. 32 heavy chain CDR1
SYDMY

SEQ ID NO. 21 Amino acid sequence of no. 32 heavy chain CDR2
EINPSNGDTNFNEKFKS

Figure 16C

SEQ ID NO. 22 Amino acid sequence of no. 32 heavy chain CDR3
GGTFYAMDY

SEQ ID NO. 23 Amino acid sequence of no. 32 light chain CDR1
RSSQSIVHSNGNTYLE

SEQ ID NO. 24 Amino acid sequence of no. 32 light chain CDR2
KVSNRFS

SEQ ID NO. 25 Amino acid sequence of no. 32 light chain CDR3
FQGSHVPWT

SEQ ID NO. 26 Amino acid sequence of no. 35 heavy chain variable region
```
  1  QVQLQQSGAE LVRSGASVKL SCTASGFNIK DYYMHWVKQR PEQGLEWIGW IDPENGDTEY
 61  APKFQGKATM TADTSSNTAY LQLSSLTSED TAVYYCNEWK FYAMDDWGQG TSVTVSS
```

SEQ ID NO. 27 Amino acid sequence of no. 35 light chain variable region
```
  1  DIVMSQSPSS LAVSVGEKVT MSCKSSQSLL YSSNQKNYLA WYQQKPGQSP KLLIYWASTR
 61  ESGVPDRFTG SGSGTDFTLT ISSVKAEDLA VYYCQQYYSY PRTFGGGTKL EIKR
```

Complementarity determining regions (CDRs) of mouse anti-human complement C2 antibody no. 35: SEQ ID NO 28-33

SEQ ID NO. 28 Amino acid sequence of no. 35 heavy chain CDR1
DYYMH

SEQ ID NO. 29 Amino acid sequence of no. 35 heavy chain CDR2
WIDPENGDTEYAPKFQG

SEQ ID NO. 30 Amino acid sequence of no. 35 heavy chain CDR3
WKFYAMDD

SEQ ID NO. 31 Amino acid sequence of no. 35 light chain CDR1
KSSQSLLYSSNQKNYLA

SEQ ID NO. 32 Amino acid sequence of no. 35 light chain CDR2
WASTRES

SEQ ID NO. 33 Amino acid sequence of no. 35 light chain CDR3
QQYYSYPRT

SEQ ID NO. 34 Amino acid sequence of no. 60 heavy chain variable region
```
  1  QVQLQQSGPG ILQPSQTLSL TCSFSGFSLS TSNMGVGWIR QPSGKGLEWL AHIWWDDDKR
 61  YNPALKSRLT ISKDTSSNQV FLKIASVDTA DTATYFCARI GRPTMITTWY LDVWGAGTTV
121  TVSS
```
SEQ ID NO. 35 Amino acid sequence of no. 60 light chain variable region
```
  1  DIQMTQSPAS LSVSVGETVT ITCRASENIY SNLAWYQQKQ GKSPQLLVYA ATKLADGVPS
 61  RFSGSGSGTQ YSLKINSLQS EDFGNYYCQH FWNTPYTFGG GTKLEIKR
```

Figure 16D

Complementarity determining regions (CDRs) of mouse anti-human complement C2 antibody no. 60: SEQ ID NO 36-41

SEQ ID NO. 36 Amino acid sequence of no. 60 heavy chain CDR1
TSNMGVG

SEQ ID NO. 37 Amino acid sequence of no. 60 heavy chain CDR2
HIWWDDDKRYNPALKS

SEQ ID NO. 38 Amino acid sequence of no. 60 heavy chain CDR3
IGRPTMITTWYLDV

SEQ ID NO. 39 Amino acid sequence of no. 60 light chain CDR1
RASENIYSNLA

SEQ ID NO. 40 Amino acid sequence of no. 60 light chain CDR2
AATKLAD

SEQ ID NO. 41 Amino acid sequence of no. 60 light chain CDR3
QHFWNTPYT

SEQ ID NO. 42 cDNA sequence coding for chimeric no. 5F2.4 human IgG4 chain
```
   1  ATGGAATGGA GCGGCGTGTT CATGTTCCTG CTGTCCGTGA CCGCGGGAGT GCACAGCGAG
  61  GTGCAGCTGC AGCAGTCTGG AGCTGAGCTG GTGAAGCCTG GGCTTCAGT GAAGATATCC
 121  TGCAAGGCTT CTGGCTACAC ATTCACTGAC TACAACATGG ACTGGGTGAA ACAGAGCCAT
 181  GGAAAGAGCC TTGAGTGGAT TGGAGATATT AATCCTAATT ATGAAAGTAC TGGGTACAAC
 241  CAGAAGTTCA AGGGAAAGGC CACATTGACT GTTGACAAGT CCTCCAGCAC AGCCTACATG
 301  GAACTCCGCA GCCTGACATC TGAGGACACT GCAGTCTATT ACTGTGCAAG AGAGGATGAT
 361  CACGACGCCT TTGCTTACTG GGGCCAAGGG ACTCTGGTCA CTGTCTCTGC AGCTAGCACC
 421  AAGGGCCCCT CCGTGTTTCC TCTGGCCCCT TGCTCCAGAT CCACCTCCGA GTCTACCGCC
 481  GCTCTGGGCT GCCTCGTGAA GGACTACTTC CCCGAGCCCG TGACAGTGTC TTGGAACTCT
 541  GGCGCCCTGA CCTCCGGCGT GCACACATTT CCAGCTGTGC TGCAGTCCTC CGGCCTGTAC
 601  TCCCTGTCCT CCGTCGTGAC TGTGCCTTCC TCTAGCCTGG GCACCAAGAC CTACACCTGT
 661  AACGTGGACC ACAAGCCCTC CAACACCAAG GTGGACAAGC GGGTGGAATC TAAGTACGGC
 721  CCTCCTTGCC CACCCTGCCC TGCCCCTGAA TTTCTGGGCG GACCTTCCGT GTTCCTGTTT
 781  CCCCCAAAGC CAAGGACAC CCTGATGATC TCCCGGACCC CCGAAGTGAC CTGCGTGGTG
 841  GTGGATGTGT CCCAGGAAGA TCCCGAGGTG CAGTTCAATT GGTACGTGGA CGGCGTGGAA
 901  GTGCACAACG CCAAGACCAA GCCAGAGAG GAACAGTTCA ACTCCACCTA CCGGGTGGTG
 961  TCCGTGCTGA CCGTGCTGCA CCAGGATTGG CTGAACGGCA AAGAGTACAA GTGCAAGGTG
1021  TCCAACAAGG GCCTGCCCTC CAGCATCGAA AAGACCATCT CCAAGGCCAA GGGCCAGCCC
1081  CGGGAACCCC AGGTGTACAC ACTGCCTCCA AGCCAGGAAG AGATGACCAA GAACCAGGTG
1141  TCCCTGACCT GTCTCGTGAA AGGCTTCTAC CCTCCGATA TCGCCGTGGA ATGGGAGTCC
1201  AACGGCCAGC CTGAGAACAA CTACAAGACC ACCCCCCCTG TGCTGGACTC CGACGGCTCC
1261  TTCTTCCTGT ACTCTCGCCT GACCGTGGAC AAGTCCCGGT GGCAGGAAGG CAACGTGTTC
1321  TCCTGCTCTG TGATGCACGA GGCCCTGCAC AACCACTACA CCCAGAAGTC CCTGTCCCTG
1381  TCTCTGGGCA AG
```

SEQ ID NO. 43 cDNA sequence coding for chimeric no. 5F2.4 human kappa chain
```
   1  ATGGAATGGA GCGGCGTGTT CATGTTCCTG CTGTCCGTGA CCGCGGGAGT GCACAGCGAC
  61  ATTGTGCTGA CACAGTCTCC TGCTTCCGTA GTTGTATCTC TGGGGCAGAG GGCCACCATC
```

Figure 16E

```
121  TCATGCAGGG CCAGCAAAAG TGTCAGAACA TCTGGCTATA ATTATATGCA CTGGTACCAA
181  CAGAAACCAG GACAGCCACC CAAACTCCTC ATCTATCTTG CATCCAACCT AAAATCTGGG
241  GTCCCTGCCA GGTTCAGTGG CAGTGGGTCT GGGACAGACT TCACCCTCAA CATCCATCCT
301  GTGGAGGAGG CGGATGCTGC AACCTATTAC TGTCAGCACA GTAGGGAGCT TCCGTACACG
361  TTCGGAGGGG GGACCAAGCT GGAAATAAAA CGGACCGTAG CCGCCCCTTC CGTGTTCATC
421  TTTCCACCCT CCGACGAGCA GCTGAAGTCT GGCACCGCTT CCGTCGTGTG CCTGCTGAAC
481  AACTTCTACC CCCGCGAGGC CAAGGTGCAG TGGAAGGTGG ACAACGCCCT GCAGTCCGGC
541  AACTCCCAGG AAAGCGTGAC CGAGCAGGAC TCCAAGGACA GCACCTACTC CCTGTCCTCC
601  ACCCTGACCC TGTCCAAGGC CGACTACGAG AAGCACAAGG TGTACGCCTG CGAAGTGACC
661  CACCAGGGCC TGTCTAGCCC CGTGACCAAG TCTTTCAACC GGGGCGAGTG C
```

SEQ ID NO. 44 cDNA sequence coding for chimeric no. 13 human IgG4 chain
```
   1  ATGGAATGGA GCGGCGTGTT CATGTTCCTG CTGTCCGTGA CCGCGGGAGT GCACAGTCAG
  61  GTCCAACTGC AGCAGCCTGG GGCTGAACTG GTGAAGCCTG GGGCTTCAGT GAAGTTGTCC
 121  TGCAAGGCTT CTGGCTACAC CTTCACCATC TACTATATGT ACTGGGTGAA GCAGAGGCCT
 181  GGACAAGGCC TTGAGTGGAT TGGGGAGGTT GATCCTAGCA TTGGTGGTAT TAGCTTCAAT
 241  GAGAAGTTCA AGAGCAAGGC CACACTGACT GTAGACAGAT CCTCCAGCAC AGCATACATG
 301  CACCTCAGCA GCCTGACATC TGAGGACTCT GCGGTCTATT ACTGTACAAG AGGTGGGACG
 361  TACTATGCTA TGGACTACTG GGGTCAAGGA ACCTCAGTCA CCGTCTCCTC AGCTAGCACC
 421  AAGGGCCCCT CCGTGTTTCC TCTGGCCCCT GCTCCAGAT CCACCTCCGA GTCTACCGCC
 481  GCTCTGGGCT GCCTCGTGAA GGACTACTTC CCCGAGCCCG TGACAGTGTC TTGGAACTCT
 541  GGCGCCCTGA CCTCCGGCGT GCACACATTT CCAGCTGTGC TGCAGTCCTC CGGCCTGTAC
 601  TCCCTGTCCT CCGTCGTGAC TGTGCCTTCC TCTAGCCTGG CACCAAGAC CTACACCTGT
 661  AACGTGGACC ACAAGCCCTC CAACACCAAG GTGGACAAGC GGGTGGAATC TAAGTACGGC
 721  CCTCCTTGCC CACCCTGCCC TGCCCCTGAA TTTCTGGGCG GACCTTCCGT GTTCCTGTTT
 781  CCCCCAAAGC CAAGGACAC CCTGATGATC TCCCGGACCC CCGAAGTGAC CTGCGTGGTG
 841  GTGGATGTGT CCCAGGAAGA TCCCGAGGTG CAGTTCAATT GGTACGTGGA CGGCGTGGAA
 901  GTGCACAACG CCAAGACCAA GCCCAGAGAG GAACAGTTCA ACTCCACCTA CCGGGTGGTG
 961  TCCGTGCTGA CCGTGCTGCA CCAGGATTGG CTGAACGGCA AGGAGTACAA GTGCAAGGTG
1021  TCCAACAAGG GCCTGCCCTC CAGCATCGAA AAGACCATCT CCAAGGCCAA GGGCCAGCCC
1081  CGGGAACCCC AGGTGTACAC ACTGCCTCCA AGCCAGGAAG AGATGACCAA GAACCAGGTG
1141  TCCCTGACCT GTCTCGTGAA AGGCTTCTAC CCCTCCGATA TCGCCGTGGA ATGGGAGTCC
1201  AACGGCCAGC CTGAGAACAA CTACAAGACC ACCCCCCCTG TGCTGGACTC CGACGGCTCC
1261  TTCTTCCTGT ACTCTCGCCT GACCGTGGAC AAGTCCCGGT GGCAGGAAGG CAACGTGTTC
1321  TCCTGCTCTG TGATGCACGA GGCCCTGCAC AACCACTACA CCCAGAAGTC CCTGTCCCTG
1381  TCTCTGGGCA AG
```

SEQ ID NO. 45 cDNA sequence coding for chimeric no. 13 human kappa chain
```
   1  ATGGAATGGA GCGGCGTGTT CATGTTCCTG CTGTCCGTGA CCGCGGGAGT GCACAGCGAT
  61  GTCCTCATGA CACAAACGCC TCTCTCCCTG CCTGTCAGTC TTGGAGATCA AGCCTCCATC
 121  TCTTGCAGAG CTGGTCAGAG CATTGTACAT AGTAATGGAA ACACCTATTT AGAATGGTAC
 181  CTGCAGAAAC CAGGCCAGTC TCCAAAGCTC CTGATCTACA AAGTTTCCAA CCGATTTTCT
 241  GGGGTCCCAG ACAGGTTCAG TGGCAGTGGA TCAGGGACAG ATTTCACACT CAAGATCAGC
 301  AGAGTGGAGG CTGAGGATCT GGGAGTTTAT TACTGCTTTC AGGGTTCACA TGTTCCGTGG
 361  ACGTTCGGTG GAGGCACCAA GCTGGAAATC AAACGGACCG TAGCCGCCCC TTCCGTGTTC
 421  ATCTTTCCAC CCTCCGACGA GCAGCTGAAG TCTGGCACCG CTTCCGTCGT GTGCCTGCTG
 481  AACAACTTCT ACCCCCGCGA GGCCAAGGTG CAGTGGAAGG TGGACAACGC CCTGCAGTCC
 541  GGCAACTCCC AGGAAAGCGT GACCGAGCAG GACTCCAAGG ACAGCACCTA CTCCCTGTCC
 601  TCCACCCTGA CCCTGTCCAA GGCCGACTAC GAGAAGCACA AGGTGTACGC CTGCGAAGTG
 661  ACCCACCAGG GCCTGTCTAG CCCCGTGACC AAGTCTTTCA ACCGGGGCGA GTGC
```

Figure 16F

SEQ ID NO. 46 cDNA sequence coding for chimeric no. 32 human IgG4 chain
```
   1  ATGGAATGGA GCGGCGTGTT CATGTTCCTG CTGTCCGTGA CCGCGGGAGT GCACAGTCAG
  61  GTGCAGCTGC AGCAGTCTGG CGCCGAGCTG GTGAAACCTG GCGCCTCCGT GAAGCTGTCC
 121  TGCAAGGCCT CCGGCTACAC CTTCACCAGC TACGACATGT ACTGGGTGAA ACAGCGGCCT
 181  GGCCAGGGCC TGGAATGGAT CGGCGAGATC AACCCCTCCA ACGGCGACAC CAACTTCAAC
 241  GAGAAGTTCA AGTCCAAGGC CACCCTGACC GTGGACAAGT CCTCCTCCAC CGCCCACATG
 301  CAGCTGTCCT CCCTGACCTC CGAGGACTCC GCCGTGTACT ACTGCACCAG AGGCGGCACC
 361  TTCTACGCTA TGGACTACTG GGGCCAGGGC ACCTCCGTGA CCGTGTCCTC TGCTAGCACC
 421  AAGGGCCCCT CCGTGTTTCC TCTGGCCCCT GCTCCAGAT CCACCTCCGA GTCTACCGCC
 481  GCTCTGGGCT GCCTCGTGAA GGACTACTTC CCCGAGCCCG TGACAGTGTC TTGGAACTCT
 541  GGCGCCCTGA CCTCCGGCGT GCACACATTT CCAGCTGTGC TGCAGTCCTC CGGCCTGTAC
 601  TCCCTGTCCT CCGTCGTGAC TGTGCCTTCC TCTAGCCTGG GCACCAAGAC CTACACCTGT
 661  AACGTGGACC ACAAGCCCTC CAACACCAAG GTGGACAAGC GGGTGGAATC TAAGTACGGC
 721  CCTCCTTGCC CACCCTGCCC TGCCCCTGAA TTTCTGGGCG GACCTTCCGT GTTCCTGTTT
 781  CCCCCAAAGC CAAGGACAC CCTGATGATC TCCCGGACCC CCGAAGTGAC CTGCGTGGTG
 841  GTGGATGTGT CCCAGGAAGA TCCCGAGGTG CAGTTCAATT GGTACGTGGA CGGCGTGGAA
 901  GTGCACAACG CCAAGACCAA GCCCAGAGAG GAACAGTTCA ACTCCACCTA CCGGGTGGTG
 961  TCCGTGCTGA CCGTGCTGCA CCAGGATTGG CTGAACGGCA AGGAGTACAA GTGCAAGGTG
1021  TCCAACAAGG GCCTGCCCTC CAGCATCGAA AAGACCATCT CCAAGGCCAA GGGCCAGCCC
1081  CGGGAACCCC AGGTGTACAC ACTGCCTCCA AGCCAGGAAG AGATGACCAA GAACCAGGTG
1141  TCCCTGACCT GTCTCGTGAA AGGCTTCTAC CCCTCCGATA TCGCCGTGGA ATGGGAGTCC
1201  AACGGCCAGC TGAGAACAA CTACAAGACC ACCCCCCCTG TGCTGGACTC CGACGGCTCC
1261  TTCTTCCTGT ACTCTCGCCT GACCGTGGAC AAGTCCCGGT GGCAGGAAGG CAACGTGTTC
1321  TCCTGCTCTG TGATGCACGA GGCCCTGCAC AACCACTACA CCCAGAAGTC CCTGTCCCTG
1381  TCTCTGGGCA AG
```

SEQ ID NO. 47 CHO-optimized cDNA sequence coding for chimeric no. 32 human IgG1 chain
```
   1  ATGGAGTGGT CCGGCGTGTT CATGTTCCTG CTGTCCGTGA CCGCTGGCGT GCACTCCCAG
  61  GTGCAGCTGC AGCAGTCTGG CGCCGAGCTG GTGAAACCTG GCGCCTCCGT GAAGCTGTCC
 121  TGCAAGGCCT CCGGCTACAC CTTCACCAGC TACGACATGT ACTGGGTGAA ACAGCGGCCT
 181  GGCCAGGGCC TGGAATGGAT CGGCGAGATC AACCCCTCCA ACGGCGACAC CAACTTCAAC
 241  GAGAAGTTCA AGTCCAAGGC CACCCTGACC GTGGACAAGT CCTCCTCCAC CGCCCACATG
 301  CAGCTGTCCT CCCTGACCTC CGAGGACTCC GCCGTGTACT ACTGCACCAG AGGCGGCACC
 361  TTCTACGCTA TGGACTACTG GGGCCAGGGC ACCTCCGTGA CCGTGTCCTC TGCCTCCACC
 421  AAGGGCCCCT CCGTGTTCCC TCTGGCCCCC TCCAGCAAGT CCACCTCTGG CGGCACCGCT
 481  GCCCTGGGCT GCCTGGTGAA AGACTACTTC CCCGAGCCTG TGACAGTGTC CTGGAACTCT
 541  GGCGCCCTGA CCAGCGGCGT GCACACCTTC CCTGCCGTGC TGCAGTCCTC CGGCCTGTAC
 601  TCCCTGTCCA GCGTGGTGAC AGTGCCCTCC TCCAGCCTGG GCACCCAGAC CTACATCTGC
 661  AACGTGAACC ACAAGCCCTC CAACACCAAG GTGGACAAGA AGGTGGAACC CAAGTCCTGC
 721  GACAAGACCC ACACCTGTCC CCCCTGCCCT GCCCCTGAAC TGCTGGGCGG ACCTTCCGTG
 781  TTCCTGTTCC CCCCAAAGCC TAAGGACACC CTGATGATCT CCCGGACCCC CGAAGTGACC
 841  TGCGTGGTGG TGGACGTGTC CCACGAGGAC CCTGAAGTGA AGTTCAATTG GTACGTGGAC
 901  GGCGTGGAAG TGCACAACGC CAAGACCAAG CCCAGAGAGG AACAGTACAA CTCCACCTAC
 961  CGGGTGGTGT CCGTGCTGAC CGTGCTGCAC CAGGACTGGC TGAACGGCAA AGAGTACAAG
1021  TGCAAGGTGT CCAACAAGGC CCTGCCTGCC CCCATCGAAA AGACCATCTC CAAGGCCAAG
1081  GGCCAGCCCC GCGAGCCCCA GGTGTACACC CTGCCCCCTA GCCGGGACGA GCTGACCAAG
1141  AACCAGGTGT CCCTGACCTG TCTGGTGAAA GGCTTCTACC CTTCCGATAT CGCCGTGGAA
1201  TGGGAGTCCA ACGGCCAGCC CGAGAACAAC TACAAGACCA CCCCCCCTGT GCTGGACTCC
1261  GACGGCTCAT TCTTCCTGTA CTCCAAGCTG ACAGTGGATA AGTCCCGGTG GCAGCAGGGC
1321  AACGTGTTCT CCTGCTCCGT GATGCACGAG GCCCTGCACA ACCACTACAC CCAGAAGTCC
1381  CTGTCCCTGA GCCCCGGCAA G
```

Figure 16G

SEQ ID NO. 48 CHO-optimized cDNA sequence coding for chimeric no. 32 human kappa chain

```
   1  ATGGAGTGGT  CCGGCGTGTT  CATGTTCCTG  CTGTCCGTGA  CCGCTGGCGT  GCACTCCGAC
  61  ATCCAGATGA  CCCAGACCCC  CCTGTCCCTG  CCCGTGTCTC  TGGGCGACCA  GGCCTCCATC
 121  TCCTGCCGGT  CCTCCCAGTC  CATCGTGCAC  TCCAACGGCA  ACACCTACCT  GGAATGGTAT
 181  CTGCAGAAGC  CCGGCCAGTC  CCCCAAGCTG  CTGATCTACA  AGGTGTCCAA  CCGGTTCTCC
 241  GGCGTGCCCG  ACAGATTCTC  CGGCTCCGGC  TCTGGCACCG  ACTTCACCCT  GAAGATCTCC
 301  CGGGTGGAAG  CCGAGGACCT  GGGCGTGTAC  TACTGTTTTC  AGGGCTCCCA  CGTGCCCTGG
 361  ACCTTCGGCG  GAGGCACCAA  GCTGGAAATC  AAGCGGACCG  TGGCCGCTCC  CTCCGTGTTC
 421  ATCTTCCCAC  CTCCGACGA   GCAGCTGAAG  TCCGGCACCG  CCTCCGTGGT  GTGCCTGCTG
 481  AACAACTTCT  ACCCCGCGA   GGCCAAGGTG  CAGTGGAAGG  TGGACAACGC  CCTGCAGTCC
 541  GGCAACTCCC  AGGAATCCGT  CACCGAGCAG  GACTCCAAGG  ACAGCACCTA  CTCCCTGTCC
 601  TCCACCCTGA  CCCTGTCCAA  GGCCGACTAC  GAGAAGCACA  AGGTGTACGC  CTGCGAAGTG
 661  ACCCACCAGG  GCCTGTCCAG  CCCCGTGACC  AAGTCCTTCA  ACCGGGGCGA  GTGC
```

SEQ ID NO. 49 cDNA sequence coding for chimeric no. 35 human IgG4 chain

```
   1  ATGGAATGGA  GCGGCGTGTT  CATGTTCCTG  CTGTCCGTGA  CCGCGGGAGT  GCACAGTCAG
  61  GTCCAGCTGC  AGCAGTCTGG  GGCAGAGCTT  GTGAGGTCAG  GGGCCTCAGT  CAAGTTGTCC
 121  TGCACAGCTT  CTGGCTTCAA  CATTAAAGAC  TACTATATGC  ACTGGGTGAA  GCAGAGGCCT
 181  GAACAGGGCC  TGGAGTGGAT  TGGATGGATT  GATCCTGAGA  ATGGTGATAC  TGAATATGCC
 241  CCGAAGTTCC  AGGGCAAGGC  CACTATGACT  GCAGACACGT  CCTCCAACAC  AGCCTACCTG
 301  CAGCTCAGCA  GCCTGACATC  TGAGGACACT  GCCGTCTATT  ACTGTAATTG  GAAAAATTC
 361  TATGCTATGG  ACGACTGGGG  TCAAGGAACC  TCAGTCACCG  TCTCCTCAGC  TAGCACCAAG
 421  GGCCCCTCCG  TGTTCCTCT   GGCCCCTTGC  TCCAGATCCA  CCTCCGAGTC  TACCGCCGCT
 481  CTGGGCTGCC  TCGTGAAGGA  CTACTTCCCC  GAGCCCGTGA  CAGTGTCTTG  GAACTCTGGC
 541  GCCCTGACCT  CCGGCGTGCA  CACATTTCCA  GCTGTGCTGC  AGTCCTCCGG  CCTGTACTCC
 601  CTGTCCTCCG  TCGTGACTGT  GCCTTCCTCT  AGCCTGGGCA  CCAAGACCTA  CACCTGTAAC
 661  GTGGACCACA  AGCCCTCCAA  CACCAAGGTG  GACAAGCGGG  TGGAATCTAA  GTACGGCCCT
 721  CCTTGCCCAC  CCTGCCCTGC  CCTGAATTT   CTGGGCGGAC  CTTCCGTGTT  CCTGTTTCCC
 781  CCAAAGCCCA  AGGACACCCT  GATGATCTCC  CGGACCCCCG  AAGTGACCTG  CGTGGTGGTG
 841  GATGTGTCCC  AGGAAGATCC  CGAGGTGCAG  TTCAATTGGT  ACGTGGACGG  CGTGGAAGTG
 901  CACAACGCCA  AGACCAAGCC  CAGAGAGGAA  CAGTTCAACT  CCACCTACCG  GGTGGTGTCC
 961  GTGCTGACCG  TGCTGCACCA  GGATTGGCTG  AACGGCAAAG  AGTACAAGTG  CAAGGTGTCC
1021  AACAAGGGCC  TGCCCTCCAG  CATCGAAAAG  ACCATCTCCA  AGGCCAAGGG  CCAGCCCCGG
1081  GAACCCCAGG  TGTACACACT  GCCTCCAAGC  CAGGAAGAGA  TGACCAAGAA  CCAGGTGTCC
1141  CTGACCTGTC  TCGTGAAAGG  CTTCTACCCC  TCCGATATCG  CCGTGGAATG  GGAGTCCAAC
1201  GGCCAGCCTG  AGAACAACTA  CAAGACCACC  CCCCCTGTGC  TGGACTCCGA  CGGCTCCTTC
1261  TTCCTGTACT  CTCGCCTGAC  CGTGGACAAG  TCCCGGTGGC  AGGAAGGCAA  CGTGTTCTCC
1321  TGCTCTGTGA  TGCACGAGGC  CCTGCACAAC  CACTACACCC  AGAAGTCCCT  GTCCCTGTCT
1381  CTGGGCAAG
```

SEQ ID NO. 50 cDNA sequence coding for chimeric no. 35 human kappa chain

```
   1  ATGGAATGGA  GCGGCGTGTT  CATGTTCCTG  CTGTCCGTGA  CCGCGGGAGT  GCACAGCGAC
  61  ATTGTGATGT  CACAGTCTCC  ATCCTCCCTA  GCTGTGTCAG  TTGGAGAGAA  GGTTACTATG
 121  AGCTGCAAGT  CCAGTCAGAG  CCTTTTATAT  AGTAGCAATC  AAAAGAACTA  CTTGGCCTGG
 181  TACCAGCAGA  AACCAGGGCA  GTCTCCTAAA  CTACTGATTT  ACTGGGCATC  CACTAGGGAA
 241  TCTGGGGTCC  CTGATCGCTT  CACAGGCAGT  GGATCTGGGA  CAGATTTCAC  TCTCACCATC
 301  AGCAGTGTGA  AGGCTGAAGA  CCTGGCAGTT  TATTACTGTC  AGCAATATTA  TAGCTATCCT
 361  CGGACGTTCG  GTGGAGGCAC  CAAGCTGGAA  ATCAAACGGA  CCGTAGCCGC  CCCTTCCGTG
 421  TTCATCTTTC  CACCCTCCGA  CGAGCAGCTG  AAGTCTGGCA  CCGCTTCCGT  CGTGTGCCTG
 481  CTGAACAACT  TCTACCCCCG  CGAGGCCAAG  GTGCAGTGGA  AGGTGGACAA  CGCCCTGCAG
 541  TCCGGCAACT  CCCAGGAAAG  CGTGACCGAG  CAGGACTCCA  AGGACAGCAC  CTACTCCCTG
 601  TCCTCCACCC  TGACCCTGTC  CAAGGCCGAC  TACGAGAAGC  ACAAGGTGTA  CGCCTGCGAA
```

Figure 16H

```
661  GTGACCCACC AGGGCCTGTC TAGCCCCGTG ACCAAGTCTT TCAACCGGGG CGAGTGC
```

SEQ ID NO. 51 cDNA sequence coding for chimeric no. 60 human IgG4 chain
```
   1  ATGGAATGGA GCGGCGTGTT CATGTTCCTG CTGTCCGTGA CCGCGGGAGT GCACAGCCAG
  61  GTGCAGCTGC AGCAGTCTGG CCCTGGGATT TTGCAGCCCT CCCAGACCCT CAGTCTGACT
 121  TGTTCTTTCT CTGGGTTTTC ACTGAGCACC TCTAATATGG GTGTAGGCTG GATTCGTCAG
 181  CCTTCAGGGA AGGGTCTGGA GTGGCTGGCA CACATTTGGT GGGATGATGA CAAGCGCTAT
 241  AATCCAGCCC TGAAGAGCCG ACTGACAATC TCCAAGGATA CCTCCAGCAA CCAGGTATTC
 301  CTCAAGATCG CCAGTGTGGA CACTGCAGAT ACTGCCACAT ACTTCTGTGC TCGAATAGGC
 361  CGACCTACTA TGATTACGAC GTGGTACCTC GATGTCTGGG GCGCAGGGAC CACGGTCACC
 421  GTCTCCTCAG CTAGCACCAA GGGCCCCTCC GTGTTTCCTC TGGCCCCTTG CTCCAGATCC
 481  ACCTCCGAGT CTACCGCCGC TCTGGGCTGC CTCGTGAAGG ACTACTTCCC CGAGCCCGTG
 541  ACAGTGTCTT GGAACTCTGG CGCCCTGACC TCCGGCGTGC ACACATTTCC AGCTGTGCTG
 601  CAGTCCTCCG GCCTGTACTC CCTGTCCTCC GTCGTGACTG TGCCTTCCTC TAGCCTGGGC
 661  ACCAAGACCT ACACCTGTAA CGTGGACCAC AAGCCCTCCA ACACCAAGGT GGACAAGCGG
 721  GTGGAATCTA AGTACGGCCC TCCTTGCCCA CCCTGCCCTG CCCCTGAATT TCTGGGCGGA
 781  CCTTCCGTGT TCCTGTTTCC CCCAAAGCCC AAGGACACCC TGATGATCTC CCGGACCCCC
 841  GAAGTGACCT GCGTGGTGGT GGATGTGTCC CAGGAAGATC CCGAGGTGCA GTTCAATTGG
 901  TACGTGGACG GCGTGGAAGT GCACAACGCC AAGACCAAGC CCAGAGAGGA ACAGTTCAAC
 961  TCCACCTACC GGGTGGTGTC CGTGCTGACC GTGCTGCACC AGGATTGGCT GAACGGCAAA
1021  GAGTACAAGT GCAAGGTGTC CAACAAGGGC CTGCCCTCCA GCATCGAAAA GACCATCTCC
1081  AAGGCCAAGG GCCAGCCCCG GGAACCCCAG GTGTACACAC TGCCTCCAAG CCAGGAAGAG
1141  ATGACCAAGA ACCAGGTGTC CCTGACCTGT CTCGTGAAAG GCTTCTACCC CTCCGATATC
1201  GCCGTGGAAT GGGAGTCCAA CGGCCAGCCT GAGAACAACT ACAAGACCAC CCCCCCTGTG
1261  CTGGACTCCG ACGGCTCCTT CTTCCTGTAC TCTCGCCTGA CCGTGGACAA GTCCCGGTGG
1321  CAGGAAGGCA ACGTGTTCTC CTGCTCTGTG ATGCACGAGG CCCTGCACAA CCACTACACC
1381  CAGAAGTCCC TGTCCCTGTC TCTGGGCAAG
```

SEQ ID NO. 52 cDNA sequence coding for chimeric no. 60 human kappa chain
```
   1  ATGGAATGGA GCGGCGTGTT CATGTTCCTG CTGTCCGTGA CCGCGGGAGT GCACAGCGAC
  61  ATCCAGATGA CTCAGTCTCC AGCCTCCCTA TCTGTATCTG TGGGAGAAAC TGTCACCATC
 121  ACATGTCGAG CAAGTGAGAA TATTTACAGT AATTTAGCAT GGTATCAGCA GAAACAGGGA
 181  AAATCTCCTC AGCTCCTGGT CTATGCTGCA ACAAAATTAG CAGATGGTGT GCCATCAAGG
 241  TTCAGTGGCA GCGGATCAGG CACACAGTAT TCCCTCAAGA TCAACAGCCT GCAGTCTGAA
 301  GATTTTGGGA CTATTACTG TCAACATTTT TGGAATACTC CGTACACGTT CGGAGGGGGG
 361  ACCAAGCTGG AAATAAAACG GACCGTAGCC GCCCCTTCCG TGTTCATCTT TCCACCCTCC
 421  GACGAGCAGC TGAAGTCTGG CACCGCTTCC GTCGTGTGCC TGCTGAACAA CTTCTACCCC
 481  CGCGAGGCCA AGGTGCAGTG GAAGGTGGAC AACGCCCTGC AGTCCGGCAA CTCCCAGGAA
 541  AGCGTGACCG AGCAGGACTC CAAGGACAGC ACCTACTCCC TGTCCTCCAC CCTGACCCTG
 601  TCCAAGGCCG ACTACGAGAA GCACAAGGTG TACGCCTGCG AAGTGACCCA CCAGGGCCTG
 661  TCTAGCCCCG TGACCAAGTC TTTCAACCGG GGCGAGTGC
```

SEQ ID NO. 53 Amino acid sequence of chimeric no. 5F2.4 human IgG4 chain
MEWSGVFMFLLSVTAGVHSEVQLQQSGAELVKPGASVKISCKASGYTFTD
YNMDWVKQSHGKSLEWIGDINPNYESTGYNQKFKGKATLTVDKSSSTAYM
ELRSLTSEDTAVYYCAREDDHDAFAYWGQGTLVTVSAASTKGPSVFPLAP
CSRSTSESTAALGCLVKDYFPEPVTVSWNSGALTSGVHTFPAVLQSSGLY
SLSSVVTVPSSSLGTKTYTCNVDHKPSNTKVDKRVESKYGPPCPPCPAPE
FLGGPSVFLFPPKPKDTLMISRTPEVTCVVVDVSQEDPEVQFNWYVDGVE
VHNAKTKPREEQFNSTYRVVSVLTVLHQDWLNGKEYKCKVSNKGLPSSIE
KTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALH

Figure 16I

NHYTQKSLSLSLGK

SEQ ID NO. 54 Amino acid sequence of chimeric no. 5F2.4 human kappa chain
MEWSGVFMFLLSVTAGVHSDIVLTQSPASVVVSLGQRATISCRASKSVRT
SGYNYMHWYQQKPGQPPKLLIYLASNLKSGVPARFSGSGSGTDFTLNIHP
VEEADAATYYCQHSRELPYTFGGGTKLEIKRTVAAPSVFIFPPSDEQLKS
GTASVVCLLNNFYPREAKVQWKVDNALQSGNSQESVTEQDSKDSTYSLSS
TLTLSKADYEKHKVYACEVTHQGLSSPVTKSFNRGEC SEQ ID NO. 55 Amino acid sequence of chimeric no.13 human IgG4 chain
MEWSGVFMFLLSVTAGVHSQVQLQQPGAELVKPGASVKLSCKASGYTFTI
YYMYWVKQRPGQGLEWIGEVDPSIGGISFNEKFKSKATLTVDRSSSTAYM
HLSSLTSEDSAVYYCTRGGTYYAMDYWGQGTSVTVSSASTKGPSVFPLAP
CSRSTSESTAALGCLVKDYFPEPVTVSWNSGALTSGVHTFPAVLQSSGLY
SLSSVVTVPSSSLGTKTYTCNVDHKPSNTKVDKRVESKYGPPCPPCPAPE
FLGGPSVFLFPPKPKDTLMISRTPEVTCVVVDVSQEDPEVQFNWYVDGVE
VHNAKTKPREEQFNSTYRVVSVLTVLHQDWLNGKEYKCKVSNKGLPSSIE
KTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALH
NHYTQKSLSLSLGK SEQ ID NO. 56 Amino acid sequence of chimeric no.13 human kappa chain
MEWSGVFMFLLSVTAGVHSDVLMTQTPLSLPVSLGDQASISCRAGQSIVH
SNGNTYLEWYLQKPGQSPKLLIYKVSNRFSGVPDRFSGSGSGTDFTLKIS
RVEAEDLGVYYCFQGSHVPWTFGGGTKLEIKRTVAAPSVFIFPPSDEQLK
SGTASVVCLLNNFYPREAKVQWKVDNALQSGNSQESVTEQDSKDSTYSLS
STLTLSKADYEKHKVYACEVTHQGLSSPVTKSFNRGEC SEQ ID NO. 57 Amino acid sequence of chimeric no. 32 human IgG4 chain
MEWSGVFMFLLSVTAGVHSQVQLQQSGAELVKPGASVKLSCKASGYTFTS
YDMYWVKQRPGQGLEWIGEINPSNGDTNFNEKFKSKATLTVDKSSSTAHM
QLSSLTSEDSAVYYCTRGGTFYAMDYWGQGTSVTVSSASTKGPSVFPLAP
CSRSTSESTAALGCLVKDYFPEPVTVSWNSGALTSGVHTFPAVLQSSGLY
SLSSVVTVPSSSLGTKTYTCNVDHKPSNTKVDKRVESKYGPPCPPCPAPE
FLGGPSVFLFPPKPKDTLMISRTPEVTCVVVDVSQEDPEVQFNWYVDGVE
VHNAKTKPREEQFNSTYRVVSVLTVLHQDWLNGKEYKCKVSNKGLPSSIE
KTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALH
NHYTQKSLSLSLGK SEQ ID NO. 58 Amino acid sequence of chimeric no. 32 human IgG1 chain
MEWSGVFMFLLSVTAGVHSQVQLQQSGAELVKPGASVKLSCKASGYTFTS
YDMYWVKQRPGQGLEWIGEINPSNGDTNFNEKFKSKATLTVDKSSSTAHM
QLSSLTSEDSAVYYCTRGGTFYAMDYWGQGTSVTVSSASTKGPSVFPLAP
SSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCP
APELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPA

Figure 16J

PIEKTISKAKGQPREPQVYTLPPSRDELTKNQVSLTCLVKGFYPSDIAVE
WESNGQPENNYKTTPPVLDSDGSFFLYSKLTVDKSRWQQGNVFSCSVMHE
ALHNHYTQKSLSLSPGK

SEQ ID NO. 59 Amino acid sequence of chimeric no. 32 human kappa chain
MEWSGVFMFLLSVTAGVHSDIQMTQTPLSLPVSLGDQASISCRSSQSIVH
SNGNTYLEWYLQKPGQSPKLLIYKVSNRFSGVPDRFSGSGSGTDFTLKIS
RVEAEDLGVYYCFQGSHVPWTFGGGTKLEIKRTVAAPSVFIFPPSDEQLK
SGTASVVCLLNNFYPREAKVQWKVDNALQSGNSQESVTEQDSKDSTYSLS
STLTLSKADYEKHKVYACEVTHQGLSSPVTKSFNRGEC SEQ ID NO. 60 Amino acid sequence of chimeric no. 35 human IgG4 chain
MEWSGVFMFLLSVTAGVHSQVQLQQSGAELVRSGASVKLSCTASGFNIKD
YYMHWVKQRPEQGLEWIGWIDPENGDTEYAPKFQGKATMTADTSSNTAYL
QLSSLTSEDTAVYYCNWEKFYAMDDWGQGTSVTVSSASTKGPSVFPLAPC
SRSTSESTAALGCLVKDYFPEPVTVSWNSGALTSGVHTFPAVLQSSGLYS
LSSVVTVPSSSLGTKTYTCNVDHKPSNTKVDKRVESKYGPPCPPCPAPEF
LGGPSVFLFPPKPKDTLMISRTPEVTCVVVDVSQEDPEVQFNWYVDGVEV
HNAKTKPREEQFNSTYRVVSVLTVLHQDWLNGKEYKCKVSNKGLPSSIEK
TISKAKGQPREPQVYTLPPSQEEMTKNQVSLTCLVKGFYPSDIAVEWESN
GQPENNYKTTPPVLDSDGSFFLYSRLTVDKSRWQEGNVFSCSVMHEALHN
HYTQKSLSLSLGK SEQ ID NO. 61 Amino acid sequence of chimeric no. 35 human kappa chain
MEWSGVFMFLLSVTAGVHSDIVMSQSPSSLAVSVGEKVTMSCKSSQSLLY
SSNQKNYLAWYQQKPGQSPKLLIYWASTRESGVPDRFTGSGSGTDFTLTI
SSVKAEDLAVYYCQQYYSYPRTFGGGTKLEIKRTVAAPSVFIFPPSDEQL
KSGTASVVCLLNNFYPREAKVQWKVDNALQSGNSQESVTEQDSKDSTYSL
SSTLTLSKADYEKHKVYACEVTHQGLSSPVTKSFNRGEC SEQ ID NO. 62 Amino acid sequence of chimeric no. 60 human IgG4 chain
MEWSGVFMFLLSVTAGVHSQVQLQQSGPGILQPSQTLSLTCSFSGFSLST
SNMGVGWIRQPSGKGLEWLAHIWWDDDKRYNPALKSRLTISKDTSSNQVF
LKIASVDTADTATYFCARIGRPTMITTWYLDVWGAGTTVTVSSASTKGPS
VFPLAPCSRSTSESTAALGCLVKDYFPEPVTVSWNSGALTSGVHTFPAVL
QSSGLYSLSSVVTVPSSSLGTKTYTCNVDHKPSNTKVDKRVESKYGPPCP
PCPAPEFLGGPSVFLFPPKPKDTLMISRTPEVTCVVVDVSQEDPEVQFNW
YVDGVEVHNAKTKPREEQFNSTYRVVSVLTVLHQDWLNGKEYKCKVSNKG
LPSSIEKTISKAKGQPREPQVYTLPPSQEEMTKNQVSLTCLVKGFYPSDI
AVEWESNGQPENNYKTTPPVLDSDGSFFLYSRLTVDKSRWQEGNVFSCSV
MHEALHNHYTQKSLSLSLGK SEQ ID NO. 63 Amino acid sequence of chimeric no. 60 human kappa chain
MEWSGVFMFLLSVTAGVHSDIQMTQSPASLSVSVGETVTITCRASENIYS
NLAWYQQKQGKSPQLLVYAATKLADGVPSRFSGSGSGTQYSLKINSLQSE
DFGNYYCQHFWNTPYTFGGGTKLEIKRTVAAPSVFIFPPSDEQLKSGTAS
VVCLLNNFYPREAKVQWKVDNALQSGNSQESVTEQDSKDSTYSLSSTLTL
SKADYEKHKVYACEVTHQGLSSPVTKSFNRGEC

Figure 16K

SEQ ID NO. 96  Consensus mouse amino acid sequence of no. 5F2.4 light chain variable region
```
  1  DNVLTQSPAS VVVSLGQRAT ISCRASKSVR TSGYNYMHWY QQKPGQPPKL LIYLASNLKS
 61  GVPARFSGSG SGTDFTLNIH PVEEADAATY YCQHSRELPY TFGGGTKLEI KR
```

SEQ ID NO. 97 Consensus mouse amino acid sequence of no. 35 heavy chain variable region
```
  1  EVQLQQSGAE LVRSGASVKL SCTASGFNIK DYYMHWVKQR PEQGLEWIGW IDPENGDTEY
 61  APKFQGKATM TADTSSNTAY LQLSSLTSED TAVYYCNEWK FYAMDDWGQG TSVTVSS
```

SEQ ID NO. 98 Consensus mouse amino acid sequence of no. 60 heavy chain variable region
```
  1  QVALKESGPG ILQPSQTLSL TCSFSGFSLS TSNMGVGWIR QPSGKGLEWL AHIWWDDDKR
 61  YNPALKSRLT ISKDTSSNQV FLKIASVDTA DTATYFCARI GRPTMITTWY LDVWGAGTTV
121  TVSS
```

SEQ ID NO. 99
Amino acid sequence of humanized light chain variable region VL1 anti-C2-5F2.4
```
DNVLTQSPDSLVVSLGERATISCRASKSVRTSGYNYMHWYQQKPGQPPKL
LIYLASNLKSGVPARFSGSGSGTDFTLTISSLQEEDAATYYCQHSRELPY
TFGQGTKLEIK
```

SEQ ID NO. 100
Amino acid sequence of humanized light chain variable region VL2 anti-C2-5F2.4
```
DNVLTQSPDSLAVSLGERATISCRASKSVRTSGYNYMHWYQQKPGQPPKL
LIYLASNLKSGVPARFSGSGSGTDFTLTISSLQAEDAATYYCQHSRELPY
TFGQGTKLEIK
```

SEQ ID NO. 101
Amino acid sequence of humanized light chain variable region VL3 anti-C2-5F2.4
```
DNVLTQSPDSLAVSLGERATISCRASKSVRTSGYNYMHWYQQKPGQPPKL
LIYLASNLKSGVPDRFSGSGSGTDFTLTISSLQAEDAATYYCQHSRELPY
TFGQGTKLEIK
```

SEQ ID NO. 102
Amino acid sequence of humanized light chain variable region VL4 anti-C2-5F2.4
```
DNVLTQSPDSLAVSLGERATINCRASKSVRTSGYNYMHWYQQKPGQPPKL
LIYLASNLKSGVPDRFSGSGSGTDFTLTISSLQAEDAATYYCQHSRELPY
TFGQGTKLEIK
```

SEQ ID NO. 103
Amino acid sequence of humanized heavy chain variable region VH1 anti-C2-5F2.4
```
EVQLVQSGAELKKPGASVKISCKASGYTFTDYNMDWVKQAHGQGLEWIGD
INPNYESTGYNQKFKGRATLTVDKSISTAYMELRSLTSEDTAVYYCARED
DHDAFAYWGQGTLVTVSS
```

Figure 16L

SEQ ID NO. 104
Amino acid sequence of humanized heavy chain variable region VH2 anti-C2-5F2.4
EVQLVQSGAEVKKPGASVKISCKASGYTFTDYNMDWVKQATGQGLEWIGD
INPNYESTGYNQKFKGRATLTVDKSISTAYMELSSLRSEDTAVYYCARED
DHDAFAYWGQGTLVTVSS SEQ ID NO. 105
Amino acid sequence of humanized heavy chain variable region VH3 anti-C2-5F2.4
EVQLVQSGAEVKKPGASVKISCKASGYTFTDYNMDWVRQATGQGLEWIGD
INPNYESTGYNQKFKGRATLTVNKSISTAYMELSSLRSEDTAVYYCARED
DHDAFAYWGQGTLVTVSS SEQ ID NO. 106
Amino acid sequence of humanized heavy chain variable region VH4 anti-C2-5F2.4
EVQLVQSGAEVKKPGASVKVSCKASGYTFTDYNMDWVRQATGQGLEWIGD
INPNYESTGYNQKFKGRATMTVNKSISTAYMELSSLRSEDTAVYYCARED
DHDAFAYWGQGTLVTVSS SEQ ID NO. 107
cDNA sequence coding for humanized light κ chain 5F2.4 containing humanized VL1
GACAACGTGCTGACCCAGTCCCCTGACTCCCTGGTGGTGTCTCTGGGCGAGAGAGCCACC
ATCTCTTGCCGGGCCTCTAAGTCCGTGCGGACCTCCGGCTACAACTACATGCACTGGTAT
CAGCAGAAGCCCGGCCAGCCCCCAAGCTGCTGATCTACCTGGCCTCCAACCTGAAGTCC
GGCGTGCCCGCCAGATTCTCCGGCTCTGGCTCTGGCACCGACTTTACCCTGACCATCAGC
TCCCTGCAGGAAGAGGACGCCGCCACCTACTACTGCCAGCACTCCAGAGAGCTGCCCTAC
ACCTTTGGCCAGGGCACCAAGCTGGAAATCAAGCGGACCGTGGCCGCTCCCTCCGTGTTC
ATCTTCCCACCTTCCGACGAGCAGCTGAAGTCTGGCACAGCCTCCGTCGTGTGCCTGCTG
AACAACTTCTACCCCCGCGAGGCCAAGGTGCAGTGGAAGGTGGACAACGCCCTGCAGTCC
GGCAACTCCCAGGAATCCGTGACCGAGCAGGACTCCAAGGACAGCACCTACTCCCTGTCC
TCCACCCTGACCCTGTCCAAGGCCGACTACGAGAAGCACAAGGTGTACGCCTGCGAAGTG
ACCCACCAGGGCCTGTCTAGCCCCGTGACCAAGTCTTTCAACCGGGGCGAGTGC SEQ ID NO. 108
cDNA sequence coding for humanized light κ chain 5F2.4 containing humanized VL2
GACAACGTGCTGACCCAGTCCCCTGACTCCCTGGCTGTGTCTCTGGGCGAGAGAGCCACC
ATCTCTTGCCGGGCCTCTAAGTCCGTGCGGACCTCCGGCTACAACTACATGCACTGGTAT
CAGCAGAAGCCCGGCCAGCCCCCAAGCTGCTGATCTACCTGGCCTCCAACCTGAAGTCC
GGCGTGCCCGCCAGATTCTCCGGCTCTGGCTCTGGCACCGACTTTACCCTGACCATCAGC
TCCCTGCAGGCCGAGGATGCCGCCACCTACTACTGCCAGCACTCCAGAGAGCTGCCCTAC
ACCTTTGGCCAGGGCACCAAGCTGGAAATCAAGCGGACCGTGGCCGCTCCCTCCGTGTTC
ATCTTCCCACCTTCCGACGAGCAGCTGAAGTCTGGCACAGCCTCCGTCGTGTGCCTGCTG
AACAACTTCTACCCCCGCGAGGCCAAGGTGCAGTGGAAGGTGGACAACGCCCTGCAGTCC
GGCAACTCCCAGGAATCCGTGACCGAGCAGGACTCCAAGGACAGCACCTACTCCCTGTCC

Figure 16M

```
TCCACCCTGACCCTGTCCAAGGCCGACTACGAGAAGCACAAGGTGTACGCCTGCGAAGTG
ACCCACCAGGGCCTGTCTAGCCCCGTGACCAAGTCTTTCAACCGGGGCGAGTGC
```

SEQ ID NO. 109 cDNA sequence coding for humanized light κ chain 5F2.4 containing humanized VL3

```
GACAACGTGCTGACCCAGTCCCCTGACTCCCTGGCTGTGTCTCTGGGCGAGAGAGCCACC
ATCTCTTGCCGGGCCTCTAAGTCCGTGCGGACCTCCGGCTACAACTACATGCACTGGTAT
CAGCAGAAGCCCGGCCAGCCCCCAAGCTGCTGATCTACCTGGCCTCCAACCTGAAGTCC
GGCGTGCCCGACAGATTCTCCGGCTCTGGCTCTGGCACCGACTTTACCCTGACCATCAGC
TCCCTGCAGGCCGAGGATGCCGCCACCTACTACTGCCAGCACTCCAGAGAGCTGCCCTAC
ACCTTTGGCCAGGGCACCAAGCTGGAAATCAAGCGGACCGTGGCCGCTCCCTCCGTGTTC
ATCTTCCCACCTTCCGACGAGCAGCTGAAGTCTGGCACAGCCTCCGTCGTGTGCCTGCTG
AACAACTTCTACCCCCGCGAGGCCAAGGTGCAGTGGAAGGTGGACAACGCCCTGCAGTCC
GGCAACTCCCAGGAATCCGTGACCGAGCAGGACTCCAAGGACAGCACCTACTCCCTGTCC
TCCACCCTGACCCTGTCCAAGGCCGACTACGAGAAGCACAAGGTGTACGCCTGCGAAGTG
ACCCACCAGGGCCTGTCTAGCCCCGTGACCAAGTCTTTCAACCGGGGCGAGTGC
```

SEQ ID NO. 110 cDNA sequence coding for humanized light κ chain 5F2.4 containing humanized VL4

```
GACAACGTGCTGACCCAGTCCCCTGACTCCCTGGCTGTGTCTCTGGGCGAGAGAGCCACC
ATCAACTGCCGGGCCTCTAAGTCCGTGCGGACCTCCGGCTACAACTACATGCACTGGTAT
CAGCAGAAGCCCGGCCAGCCCCCAAGCTGCTGATCTACCTGGCCTCCAACCTGAAGTCC
GGCGTGCCCGACAGATTCTCCGGCTCTGGCTCTGGCACCGACTTTACCCTGACCATCAGC
TCCCTGCAGGCCGAGGATGCCGCCACCTACTACTGCCAGCACTCCAGAGAGCTGCCCTAC
ACCTTTGGCCAGGGCACCAAGCTGGAAATCAAGCGGACCGTGGCCGCTCCCTCCGTGTTC
ATCTTCCCACCTTCCGACGAGCAGCTGAAGTCTGGCACAGCCTCCGTCGTGTGCCTGCTG
AACAACTTCTACCCCCGCGAGGCCAAGGTGCAGTGGAAGGTGGACAACGCCCTGCAGTCC
GGCAACTCCCAGGAATCCGTGACCGAGCAGGACTCCAAGGACAGCACCTACTCCCTGTCC
TCCACCCTGACCCTGTCCAAGGCCGACTACGAGAAGCACAAGGTGTACGCCTGCGAAGTG
ACCCACCAGGGCCTGTCTAGCCCCGTGACCAAGTCTTTCAACCGGGGCGAGTGC
```

SEQ ID NO. 111 cDNA sequence coding for humanized IgG4 chain 5F2.4 containing humanized VH1

```
GAAGTGCAGCTGGTGCAGTCTGGCGCCGAGCTGAAGAAACCTGGCGCCTCCGTGAAGATC
TCCTGCAAGGCCTCCGGCTACACCTTCACCGACTACAACATGGACTGGGTCAAGCAGGCC
CACGGCCAGGGCCTGGAATGGATCGGCGACATCAACCCCAACTACGAGTCCACCGGCTAC
AACCAGAAGTTCAAGGGCAGAGCCACCCTGACCGTGGACAAGTCCATCTCCACCGCCTAC
ATGGAACTGCGGTCCCTGACCTCTGAGGACACCGCCGTGTACTACTGCGCCAGAGAGGAC
GACCACGACGCCTTTGCTTATTGGGGCCAGGGCACCCTCGTGACCGTGTCCTCTGCTTCT
ACCAAGGGCCCCTCCGTGTTCCCTCTGGCCCCTTGCTCCAGATCCACCTCCGAGTCTACC
```

Figure 16N

GCCGCTCTGGGCTGCCTCGTGAAGGACTACTTCCCCGAGCCCGTGACAGTGTCTTGGAAC
TCTGGCGCTCTGACCTCCGGCGTGCACACCTTTCCAGCTGTGCTGCAGTCCTCCGGCCTG
TACTCCCTGTCCTCCGTCGTGACTGTGCCCTCCAGCTCTCTGGGCACCAAGACCTACACC
TGTAACGTGGACCACAAGCCCTCCAACACCAAGGTGGACAAGCGGGTGGAATCTAAGTAC
GGCCCTCCCTGCCCTCCTTGCCCAGCCCCTGAATTTCTGGGCGGACCCAGCGTGTTCCTG
TTCCCCCCAAAGCCCAAGGACACCCTGATGATCTCCCGGACCCCCGAAGTGACCTGCGTG
GTGGTGGATGTGTCCCAGGAAGATCCCGAGGTGCAGTTCAATTGGTACGTGGACGGCGTG
GAAGTGCACAACGCCAAGACCAAGCCTAGAGAGGAACAGTTCAACTCCACCTACCGGGTG
GTGTCCGTGCTGACCGTGCTGCACCAGGATTGGCTGAACGGCAAAGAGTACAAGTGCAAG
GTGTCCAACAAGGGCCTGCCTTCCAGCATCGAAAAGACCATCTCCAAGGCCAAGGGCCAG
CCCCGGGAACCCCAGGTGTACACACTGCCTCCAAGCCAGGAAGAGATGACCAAGAACCAG
GTGTCCCTGACATGCCTCGTGAAAGGCTTCTACCCCTCCGATATCGCCGTGGAATGGGAG
TCCAACGGCCAGCCTGAGAACAACTACAAGACCACCCCCCCTGTGCTGGACTCCGACGGC
TCCTTCTTCCTGTACTCTCGGCTGACAGTGGATAAGAGCCGGTGGCAGGAAGGCAACGTG
TTCTCCTGCTCCGTGATGCACGAGGCCCTGCACAACCACTATACCCAGAAGTCCCTGTCC
CTGAGCCTGGGCAAG

SEQ ID NO. 112
cDNA sequence coding for humanized IgG4 chain 5F2.4 containing humanized VH2
GAAGTGCAGCTGGTGCAGTCTGGCGCCGAAGTGAAGAAACCTGGCGCCTCCGTGAAGATC
TCCTGCAAGGCCTCCGGCTACACCTTCACCGACTACAACATGGACTGGGTCAAGCAGGCC
ACCGGCCAGGGCCTGGAATGGATCGGCGACATCAACCCCAACTACGAGTCCACCGGCTAC
AACCAGAAGTTCAAGGGCAGAGCCACCCTGACCGTGGACAAGTCCATCTCCACCGCCTAC
ATGGAACTGTCCTCCCTGCGGAGCGAGGACACCGCCGTGTACTACTGCGCCAGAGAGGAC
GACCACGACGCCTTTGCTTATTGGGGCCAGGGCACCCTCGTGACCGTGTCCTCTGCTTCT
ACCAAGGGCCCCTCCGTGTTCCCTCTGGCCCCTTGCTCCAGATCCACCTCCGAGTCTACC
GCCGCTCTGGGCTGCCTCGTGAAGGACTACTTCCCCGAGCCCGTGACAGTGTCTTGGAAC
TCTGGCGCCCTGACCTCCGGCGTGCACACCTTTCCAGCTGTGCTGCAGTCCTCCGGCCTG
TACTCCCTGTCCTCCGTCGTGACTGTGCCCTCCAGCTCTCTGGGCACCAAGACCTACACC
TGTAACGTGGACCACAAGCCCTCCAACACCAAGGTGGACAAGCGGGTGGAATCTAAGTAC
GGCCCTCCCTGCCCTCCTTGCCCAGCCCCTGAATTTCTGGGCGGACCCAGCGTGTTCCTG
TTCCCCCCAAAGCCCAAGGACACCCTGATGATCTCCCGGACCCCCGAAGTGACCTGCGTG
GTGGTGGATGTGTCCCAGGAAGATCCCGAGGTGCAGTTCAATTGGTACGTGGACGGCGTG
GAAGTGCACAACGCCAAGACCAAGCCTAGAGAGGAACAGTTCAACTCCACCTACCGGGTG
GTGTCCGTGCTGACCGTGCTGCACCAGGATTGGCTGAACGGCAAAGAGTACAAGTGCAAG
GTGTCCAACAAGGGCCTGCCTTCCAGCATCGAAAAGACCATCTCCAAGGCCAAGGGCCAG
CCCCGGGAACCCCAGGTGTACACACTGCCTCCAAGCCAGGAAGAGATGACCAAGAACCAG
GTGTCCCTGACCTGTCTCGTGAAAGGCTTCTACCCCTCCGATATCGCCGTGGAATGGGAG
TCCAACGGCCAGCCTGAGAACAACTACAAGACCACCCCCCCTGTGCTGGACTCCGACGGC
TCCTTCTTCCTGTACTCTCGGCTGACAGTGGATAAGAGCCGGTGGCAGGAAGGCAACGTG
TTCTCCTGCTCCGTGATGCACGAGGCCCTGCACAACCACTATACCCAGAAGTCCCTGTCC

Figure 16O

CTGTCTCTGGGAAAG

SEQ ID NO. 113
cDNA sequence coding for humanized IgG4 chain 5F2.4 containing humanized VH3
GAAGTGCAGCTGGTGCAGTCTGGCGCCGAAGTGAAGAAACCTGGCGCCTCCGTGAAGATC
TCCTGCAAGGCCTCCGGCTACACCTTCACCGACTACAACATGGACTGGGTGCGACAGGCT
ACCGGCCAGGGCCTGGAATGGATCGGCGACATCAACCCCAACTACGAGTCCACCGGCTAC
AACCAGAAGTTCAAGGGCAGAGCCACCCTGACCGTGAACAAGTCCATCTCCACCGCCTAC
ATGGAACTGTCCTCCCTGCGGAGCGAGGACACCGCCGTGTACTACTGCGCCAGAGAGGAC
GACCACGACGCCTTTGCTTATTGGGGCCAGGGCACCCTCGTGACCGTGTCCTCTGCTTCT
ACCAAGGGCCCCTCCGTGTTCCCTCTGGCCCCTTGCTCCAGATCCACCTCCGAGTCTACC
GCCGCTCTGGGCTGCCTCGTGAAGGACTACTTCCCCGAGCCCGTGACAGTGTCTTGGAAC
TCTGGCGCCCTGACCTCCGGCGTGCACACCTTTCCAGCTGTGCTGCAGTCCTCCGGCCTG
TACTCCCTGTCCTCCGTCGTGACTGTGCCCTCCAGCTCTCTGGGCACCAAGACCTACACC
TGTAACGTGGACCACAAGCCCTCCAACACCAAGGTGGACAAGCGGGTGGAATCTAAGTAC
GGCCCTCCCTGCCCTCCTTGCCCAGCCCCTGAATTTCTGGGCGGACCCAGCGTGTTCCTG
TTCCCCCCAAAGCCCAAGGACACCCTGATGATCTCCCGGACCCCCGAAGTGACCTGCGTG
GTGGTGGATGTGTCCCAGGAAGATCCCGAGGTGCAGTTCAATTGGTACGTGGACGGCGTG
GAAGTGCACAACGCCAAGACCAAGCCTAGAGAGGAACAGTTCAACTCCACCTACCGGGTG
GTGTCCGTGCTGACCGTGCTGCACCAGGATTGGCTGAACGGCAAAGAGTACAAGTGCAAG
GTGTCCAACAAGGGCCTGCCTTCCAGCATCGAAAAGACCATCTCCAAGGCCAAGGGCCAG
CCCCGGGAACCCCAGGTGTACACACTGCCTCCAAGCCAGGAAGAGATGACCAAGAACCAG
GTGTCCCTGACCTGTCTCGTGAAAGGCTTCTACCCCTCCGATATCGCCGTGGAATGGGAG
TCCAACGGCCAGCCTGAGAACAACTACAAGACCACCCCCCCTGTGCTGGACTCCGACGGC
TCCTTCTTCCTGTACTCTCGGCTGACAGTGGACAAGAGCCGGTGGCAGGAAGGCAACGTG
TTCTCCTGCTCCGTGATGCACGAGGCCCTGCACAACCACTATACCCAGAAGTCCCTGTCC
CTGTCTCTGGGAAAG SEQ ID NO. 114
cDNA sequence coding for humanized IgG4 chain 5F2.4 containing humanized VH4
GAAGTGCAGCTGGTGCAGTCTGGCGCCGAAGTGAAGAAACCTGGCGCCTCCGTGAAGGTG
TCCTGCAAGGCTTCCGGCTACACCTTTACCGACTACAACATGGACTGGGTGCGACAGGCT
ACCGGCCAGGGCCTGGAATGGATCGGCGACATCAACCCCAACTACGAGTCCACCGGCTAC
AACCAGAAGTTCAAGGGCAGAGCCACCATGACCGTGAACAAGTCCATCTCCACCGCCTAC
ATGGAACTGTCCTCCCTGCGGAGCGAGGACACCGCCGTGTACTACTGCGCCAGAGAGGAC
GACCACGACGCCTTTGCTTATTGGGGCCAGGGCACCCTCGTGACCGTGTCCTCTGCTTCT
ACCAAGGGCCCCTCCGTGTTCCCTCTGGCCCCTTGCTCCAGATCCACCTCCGAGTCTACC
GCCGCTCTGGGCTGCCTCGTGAAGGACTACTTCCCCGAGCCCGTGACAGTGTCTTGGAAC
TCTGGCGCCCTGACCTCCGGCGTGCACACCTTTCCAGCTGTGCTGCAGTCCTCCGGCCTG
TACTCCCTGTCCTCCGTCGTGACTGTGCCCTCCAGCTCTCTGGGCACCAAGACCTACACC

Figure 16P

```
TGTAACGTGGACCACAAGCCCTCCAACACCAAGGTGGACAAGCGGGTGGAATCTAAGTAC
GGCCCTCCCTGCCCTCCTTGCCCAGCCCCTGAATTTCTGGGCGGACCCAGCGTGTTCCTG
TTCCCCCCAAAGCCCAAGGACACCCTGATGATCTCCCGGACCCCCGAAGTGACCTGCGTG
GTGGTGGATGTGTCCCAGGAAGATCCCGAGGTGCAGTTCAATTGGTACGTGGACGGCGTG
GAAGTGCACAACGCCAAGACCAAGCCTAGAGAGGAACAGTTCAACTCCACCTACCGGGTG
GTGTCCGTGCTGACCGTGCTGCACCAGGATTGGCTGAACGGCAAAGAGTACAAGTGCAAG
GTGTCCAACAAGGGCCTGCCTTCCAGCATCGAAAAGACCATCTCCAAGGCCAAGGGCCAG
CCCCGGGAACCCCAGGTGTACACACTGCCTCCAAGCCAGGAAGAGATGACCAAGAACCAG
GTGTCCCTGACCTGTCTCGTGAAAGGCTTCTACCCCTCCGATATCGCCGTGGAATGGGAG
TCCAACGGCCAGCCTGAGAACAACTACAAGACCACCCCCCCTGTGCTGGACTCCGACGGC
TCCTTCTTCCTGTACTCTCGCCTGACCGTGGATAAGTCCCGGTGGCAGGAAGGCAACGTG
TTCTCCTGCTCCGTGATGCACGAGGCCCTGCACAACCACTATACCCAGAAGTCCCTGTCC
CTGTCTCTGGGAAAG
```

SEQ ID NO. 115

Amino acid sequence coding for humanized light κ chain 5F2.4 containing humanized VL1

DNVLTQSPDSLVVSLGERATISCRASKSVRTSGYNYMHWYQQKPGQPPKLLIYLASNLKSGVPARFSGSGSGTD
FTLTISSLQEEDAATYYCQHSRELPYTFGQGTKLEIKRTVAAPSVFIFPPSDEQLKSGTASVVCLLNNFYPREA
KVQWKVDNALQSGNSQESVTEQDSKDSTYSLSSTLTLSKADYEKHKVYACEVTHQGLSSPVTKSFNRGEC

SEQ ID NO. 116

Amino acid sequence coding for humanized light κ chain 5F2.4 containing humanized VL2

DNVLTQSPDSLAVSLGERATISCRASKSVRTSGYNYMHWYQQKPGQPPKLLIYLASNLKSGVPARFSGSGSGTD
FTLTISSLQAEDAATYYCQHSRELPYTFGQGTKLEIKRTVAAPSVFIFPPSDEQLKSGTASVVCLLNNFYPREA
KVQWKVDNALQSGNSQESVTEQDSKDSTYSLSSTLTLSKADYEKHKVYACEVTHQGLSSPVTKSFNRGEC

SEQ ID NO. 117

Amino acid sequence coding for humanized light κ chain 5F2.4 containing humanized VL3

DNVLTQSPDSLAVSLGERATISCRASKSVRTSGYNYMHWYQQKPGQPPKLLIYLASNLKSGVPDRFSGSGSGTD
FTLTISSLQAEDAATYYCQHSRELPYTFGQGTKLEIKRTVAAPSVFIFPPSDEQLKSGTASVVCLLNNFYPREA
KVQWKVDNALQSGNSQESVTEQDSKDSTYSLSSTLTLSKADYEKHKVYACEVTHQGLSSPVTKSFNRGEC

SEQ ID NO. 118

Amino acid sequence coding for humanized light κ chain 5F2.4 containing humanized VL4

DNVLTQSPDSLAVSLGERATINCRASKSVRTSGYNYMHWYQQKPGQPPKLLIYLASNLKSGVPDRFSGSGSGTD
FTLTISSLQAEDAATYYCQHSRELPYTFGQGTKLEIKRTVAAPSVFIFPPSDEQLKSGTASVVCLLNNFYPREA
KVQWKVDNALQSGNSQESVTEQDSKDSTYSLSSTLTLSKADYEKHKVYACEVTHQGLSSPVTKSFNRGEC

SEQ ID NO. 119

Amino acid sequence coding for humanized IgG4 chain 5F2.4 containing humanized VH1

EVQLVQSGAELKKPGASVKISCKASGYTFTDYNMDWVKQAHGQGLEWIGDINPNYESTGYNQKFKGRATLTVDK
SISTAYMELRSLTSEDTAVYYCAREDDHDAFAYWGQGTLVTVSSASTKGPSVFPLAPCSRSTSESTAALGCLVK
DYFPEPVTVSWNSGALTSGVHTFPAVLQSSGLYSLSSVVTVPSSSLGTKTYTCNVDHKPSNTKVDKRVESKYGP
PCPPCPAPEFLGGPSVFLFPPKPKDTLMISRTPEVTCVVVDVSQEDPEVQFNWYVDGVEVHNAKTKPREEQFNS

Figure 16Q

TYRVVSVLTVLHQDWLNGKEYKCKVSNKGLPSSIEKTISKAKGQPREPQVYTLPPSQEEMTKNQVSLTCLVKGF
YPSDIAVEWESNGQPENNYKTTPPVLDSDGSFFLYSRLTVDKSRWQEGNVFSCSVMHEALHNHYTQKSLSLSLG
K

SEQ ID NO. 120

Amino acid sequence coding for humanized IgG4 chain 5F2.4 containing humanized VH2

EVQLVQSGAEVKKPGASVKISCKASGYTFTDYNMDWVKQATGQGLEWIGDINPNYESTGYNQKFKGRATLTVDK
SISTAYMELSSLRSEDTAVYYCAREDDHDAFAYWGQGTLVTVSSASTKGPSVFPLAPCSRSTSESTAALGCLVK
DYFPEPVTVSWNSGALTSGVHTFPAVLQSSGLYSLSSVVTVPSSSLGTKTYTCNVDHKPSNTKVDKRVESKYGP
PCPPCPAPEFLGGPSVFLFPPKPKDTLMISRTPEVTCVVVDVSQEDPEVQFNWYVDGVEVHNAKTKPREEQFNS
TYRVVSVLTVLHQDWLNGKEYKCKVSNKGLPSSIEKTISKAKGQPREPQVYTLPPSQEEMTKNQVSLTCLVKGF
YPSDIAVEWESNGQPENNYKTTPPVLDSDGSFFLYSRLTVDKSRWQEGNVFSCSVMHEALHNHYTQKSLSLSLG
K

SEQ ID NO. 121

Amino acid sequence coding for humanized IgG4 chain 5F2.4 containing humanized VH3

EVQLVQSGAEVKKPGASVKISCKASGYTFTDYNMDWVRQATGQGLEWIGDINPNYESTGYNQKFKGRATLTVNK
SISTAYMELSSLRSEDTAVYYCAREDDHDAFAYWGQGTLVTVSSASTKGPSVFPLAPCSRSTSESTAALGCLVK
DYFPEPVTVSWNSGALTSGVHTFPAVLQSSGLYSLSSVVTVPSSSLGTKTYTCNVDHKPSNTKVDKRVESKYGP
PCPPCPAPEFLGGPSVFLFPPKPKDTLMISRTPEVTCVVVDVSQEDPEVQFNWYVDGVEVHNAKTKPREEQFNS
TYRVVSVLTVLHQDWLNGKEYKCKVSNKGLPSSIEKTISKAKGQPREPQVYTLPPSQEEMTKNQVSLTCLVKGF
YPSDIAVEWESNGQPENNYKTTPPVLDSDGSFFLYSRLTVDKSRWQEGNVFSCSVMHEALHNHYTQKSLSLSLG
K

SEQ ID NO. 122

Amino acid sequence coding for humanized IgG4 chain 5F2.4 containing humanized VH4

EVQLVQSGAEVKKPGASVKVSCKASGYTFTDYNMDWVRQATGQGLEWIGDINPNYESTGYNQKFKGRATMTVNK
SISTAYMELSSLRSEDTAVYYCAREDDHDAFAYWGQGTLVTVSSASTKGPSVFPLAPCSRSTSESTAALGCLVK
DYFPEPVTVSWNSGALTSGVHTFPAVLQSSGLYSLSSVVTVPSSSLGTKTYTCNVDHKPSNTKVDKRVESKYGP
PCPPCPAPEFLGGPSVFLFPPKPKDTLMISRTPEVTCVVVDVSQEDPEVQFNWYVDGVEVHNAKTKPREEQFNS
TYRVVSVLTVLHQDWLNGKEYKCKVSNKGLPSSIEKTISKAKGQPREPQVYTLPPSQEEMTKNQVSLTCLVKGF
YPSDIAVEWESNGQPENNYKTTPPVLDSDGSFFLYSRLTVDKSRWQEGNVFSCSVMHEALHNHYTQKSLSLSLG
K

Figure 20

*Binding characteristics of mAb anti-C2-5F2.4*

| Target in ELISA | 5F2.4 binding |
|---|---|
| BSA (583 aa) | - |
| C2 (732 aa) | + |
| deglycosylated C2 | + |
| C1s-cleaved C2 | + |
| C2a (509 aa) | - |
| denatured C2 | + |
| reduced C2 | - |

|  | C2b | C2a |
|---|---|---|
| Intra S-S bonds | 6x | 2x |
| N-linked glycans | 2x | 6x |

BINDING MOLECULES THAT BIND HUMAN COMPLEMENT FACTOR C2 AND USES THEREOF

The invention relates to the field of immunology/biochemistry. The invention relates to means and methods for inhibiting the activation of the classical and lectin pathways of the complement system and use thereof in the treatment of human conditions. The invention relates to inhibitors of complement factors and uses thereof. The invention in particular relates to binding molecules that bind to human complement factor C2 and uses thereof in the treatment or prevention complement activation mediated diseases or disorders, such as antibody-mediated inflammatory diseases and ischemia-reperfusion (I/R) injury in ischemic conditions.

The complement system involves proteins that circulate in the blood. The complement factors circulate as inactive precursor proteins. Activation of the system leads to an activation cascade where one factor activates the subsequent one by specific proteolysis of complement protein further downstream in the cascade. The complement system belongs to the so-called plasma cascade systems. The complement system is among others involved in the host defence against invading micro-organisms.

Activation of the complement system can occur via three pathways, the classical, the lectin pathway, and the alternative pathway. Each pathway activates a central component, C3 or the third complement factor, which results in the activation of a common terminal pathway leading to the formation of the membrane-attack complex (Muller-Eberhard, Annu Rev Biochem 1988, 57:321). During complement activation, several inflammatory peptides like the anaphyla-toxins C3a and C5a are generated as well as the membrane attack complex, C5b-9. These activation products elicit pleiotropic biological effects such as chemotaxis of leukocytes, degranulation of phagocytic cells, mast cells and basophils, smooth muscle contraction, the increase of vascular permeability and the lysis of cells (Hugli, Complement 1986, 3:111). Complement activation products also induce the generation of toxic oxygen radicals and the synthesis and release of arachidonic acid metabolites and cytokines, in particular by phagocytes, which further amplifies the inflammatory response.

Although complement is an important line of defence against pathogenic organisms, its activation can also confer damage to otherwise healthy host cells. Complement-mediated tissue damage plays a role in many inflammatory diseases including sepsis, immune complex diseases as rheumatoid arthritis, systemic lupus erythematosus and vasculitis, multiple trauma, several neurologic diseases such as multifocal motor neuropathy ischemia-reperfusion (I/R) injury such as during myocardial infarction, etc. The pathogenic role of complement activation in these conditions is the result of one or more of the aforementioned biological effects of its activation products. Inhibition of complement activation is therefore beneficial in these conditions.

Activation of complement can be inhibited by natural inhibitors which control activation at several levels of the cascade. These inhibitors include C1-inhibitor, which inhibits the early steps of activation of the classical and lectin pathways, factor H and C4 binding protein which dissociate C3- and C4-convertases, respectively, and act as cofactors for factor I which degrades C4b and C3b, the regulatory membrane proteins CR1, DAF and MCP that exert similar functions as H, and the plasma proteins vitronectin and clusterin and the membrane protein CD59 which inhibit MAC (Sahu et al., Immunol Res 1998, 17:109; Campbell et al., Annu Rev Immunol 1988, 6:161).

Inhibition of complement activation is an attractive therapeutic option. Indeed several endogenous soluble complement inhibitors (C1-inhibitor; soluble complement receptor 1 or sCR1) have been produced as a recombinant protein and evaluated in clinical studies. Also, the administration of antibodies that inhibit key proteins of the cascade reaction such as C5 (Thomas et al., Mol Immunol 1996, 33:1389) has been evaluated. One such antibody, Soliris® or eculizumab, is an anti-05 antibody. The antibody is presently approved for use in the treatment of paroxysmal nocturnal hemoglobinuria and atypical haemolytic uremic syndrome.

A role of complement is to facilitate the phagocytosis of invading microorganisms. Hence, inhibition of complement in inflammatory diseases has the inherent disadvantage that it increases the risk for infections. Both the lectin and the alternative pathways of complement activation can be directly activated by micro-organisms, whereas the classical pathway is activated by IgG or IgM antibodies bound to antigens such microorganisms.

The present invention provides a binding molecule that binds to human complement factor C2. In one embodiment the binding molecule comprises an immunoglobulin heavy chain variable region and an immunoglobulin light chain variable region (a) comprising the amino acid sequences of SEQ ID NO: 2 and SEQ ID NO: 3 resp.; SEQ ID NO: 2 and SEQ ID NO: 96 resp.; SEQ ID NO: 10 and SEQ ID NO: 11 resp.; SEQ ID NO: 18 and SEQ ID NO: 19 resp.; SEQ ID NO: 26 and SEQ ID NO: 27 resp.; SEQ ID NO: 97 and SEQ ID NO: 27 resp.; SEQ ID NO: 34 and SEQ ID NO: 35 resp.; or SEQ ID NO: 98 and SEQ ID NO: 35 resp.; or (b) comprising the amino acid sequences of SEQ ID NO: 99 and SEQ ID NO: 103 resp.; SEQ ID NO: 99 and SEQ ID NO: 104 resp.; SEQ ID NO: 99 and SEQ ID NO: 105 resp.; SEQ ID NO: 99 and SEQ ID NO: 106 resp.; SEQ ID NO: 100 and SEQ ID NO: 103 resp.; SEQ ID NO: 100 and SEQ ID NO: 104 resp.; SEQ ID NO: 100 and SEQ ID NO: 105 resp.; SEQ ID NO: 100 and SEQ ID NO: 106 resp.; SEQ ID NO: 101 and SEQ ID NO: 103 resp.; SEQ ID NO: 101 and SEQ ID NO: 104 resp.; SEQ ID NO: 101 and SEQ ID NO: 105 resp.; SEQ ID NO: 101 and SEQ ID NO: 106 resp.; SEQ ID NO: 102 and SEQ ID NO: 103 resp.; SEQ ID NO: 102 and SEQ ID NO: 104 resp.; SEQ ID NO: 102 and SEQ ID NO: 105 resp.; or SEQ ID NO: 102 and SEQ ID NO: 106 resp.; or (c) comprising the amino acid sequences specified under (a) and/or (b) but wherein one or both of said sequences comprise 1-5 amino acid substitutions.

Olglesby et al. (J Immunol 1988, 2: 926) describe a C2 specific antibody. The antibody was identified upon immunization of mice with deglycosylated and denatured C2. Immunization with native glycosylated C2 did not yield suitable C2 specific antibodies. A C2 specific antibody is also described in US2001/0026928. The antibody developed therein is directed towards the C2a subcomponent of C2. Further details on the epitope recognized by the antibody are not disclosed therein.

A binding molecule of the invention differs in the epitope that is bound on C2. Prior to the invention it was not known that there were more inactivating epitopes on C2.

Binding molecules of the invention inhibit complement activation and can be used in the treatment of a variety of diseases. The invention provides a method for the prevention or treatment of a disease mediated by complement activation, said method comprising administering to the individual in need thereof a binding molecule of the invention. The invention further provides a binding molecule of the invention for use in the prevention or treatment of a disease or disorder mediated by complement activation via the classical and/or lectin pathway.

Examples of such diseases are inflammatory disease, neurological disease or ischemia-reperfusion (I/R) injury. A preferred neurological diseases in the context of the invention is neuro-inflammatory disease. A binding molecule of the invention does not completely inhibit complement. It leaves at least some of the capacity of the complement system to defend against micro-organisms intact. A binding molecule of the invention leaves at least the alternative complement activation pathway essentially intact. This feature of the binding molecules of the invention greatly improves the therapeutic applicability of the complement inhibitors of the invention in general, and antibody based complement inhibitors in particular. Preferred examples of treatments according to the invention are antibody-mediated rejection of kidney allografts, idiopathic membranous nephropathy, immune haemolytic anemia, immune complex diseases, ischemia-reperfusion conditions such as ischemia-reperfusion injury. The binding molecules of the invention are attractive options for use in a variety of therapeutic interventions because they are effective in the limitation of the consequences of the activity of the complement system in the body while reducing the risk of side effects due to susceptibility to micro-organism infection and/or multiplication.

In one embodiment a binding molecule of the invention binds to an epitope of the C2a domain. The C2a binding molecules of the invention are effective in inhibiting C2. Such binding molecules are surprisingly effective in spite of the fact that they do not completely inhibit cleavage by C1s. A C2a binding molecule of the invention leaves the binding of C2b to C4b intact. C2 activity is nevertheless significantly inhibited by a C2a binding molecule of the invention.

In one embodiment a binding molecule of the invention binds to an epitope of the C2b domain. Such binding molecules are effective in spite of the fact that they do not completely inhibit cleavage by C1s. A C2b binding molecule of the invention leaves the binding of C2a to C4b intact. C2 activity is nevertheless significantly inhibited by a C2b binding molecule of the invention.

In a preferred embodiment a binding molecule of the invention binds to an epitope that is partly present on the C2a domain and partly present on the C2b domain. The binding molecule of the invention binds detectably to the individual C2a and C2b domains. Such a C2a/C2b binding molecule of the invention is surprisingly effective in spite of the fact that it does not completely inhibit cleavage by C1s. C2 activity is nevertheless significantly inhibited by a C2a/C2b binding molecule of the invention.

A binding molecule of the invention is preferably a Fab fragment, a single chain Fv (scFv) fragment, or an antibody or an antigen binding fragment thereof.

As used herein, the term "binding molecule comprising a heavy chain variable region and a light chain variable region" encompasses, but is not limited to, an antibody and an antigen binding fragment thereof. A preferred fragment is a Fab fragment, an scFv fragment, a unibody, a diabody, a triabody etc.

A binding molecule of the invention binds to human C2. The amino acid sequence of a preferred human C2 is given in SEQ ID: NO 1. The binding molecule preferably specifically binds to human C2. This means that, in a natural human sample, preferably a sample of human plasma, the binding molecule binds for more than 95%, preferably more than 99% to human C2, when compared to other human proteins in plasma, and has an affinity of 20 nM or less for C2.

Activation of C2 involves proteolytic cleavage into smaller fragments. These fragments are usually referred to as the C2a and the C2b fragment. The terminology used in this invention is that the C2a fragment is the larger about 70 kDa fragment. The C2a fragment forms a complex with C4b to form a C3-convertase C4bC2a. This complex is typically surface bound. The smaller about 30 kDa N-terminal C2b fragment releases into the fluid phase.

The term "C2 activity" or the like as used herein refers to the role of the C2 protein in the complement activation cascade. The C2 protein is "active" when it has switched from an inactive precursor enzyme into an active serine protease upon activation by proteolytic cleavage by C1s. Active C2 with C4b as cofactor can activate C3, and with C4b and C3b as cofactors can activate C5.

The term "C2 inhibition" or the like, as used herein also refers to its role in the complement activation cascade. The C2 protein is "inhibited" when it does not perform its role in the cascade to activate complement when the C2 activation signal (i.e. C1s) is present in its environment.

The term "antibody" refers to monoclonal and polyclonal antibodies. The antibody can be prepared from the blood of an animal. Presently, it is more common to have the antibody prepared by a cell that expresses the antibody from nucleic acid in the cell. Various cells and cell lines are available. Hybridoma cell lines were commonly used for the production of murine monoclonal antibodies. With the advent of recombinant DNA approaches it is nowadays common to use cell lines. Preferred cell lines are the PER.C6 cell line, the CHO cell line and the NS0 cell line. The antibody can be a monovalent antibody, a tetravalent or other multivalent antibody. Typically the antibody is a monovalent antibody comprising the C2 antigen binding site as indicated herein above.

In one embodiment an antibody of the invention is a multi-specific antibody. The prototype multispecific antibody is the bi-specific antibody. A multi-specific antibody comprises two or more different antigen binding sites. In such a multi-specific antibody, at least one of the antigen binding sites is provided by a binding molecule of the invention. At least one other antigen binding site is an antigen binding site directed towards a different epitope on C2, or preferably, directed towards an epitope on a different molecule. The other antigen binding site is preferably an antibody variable region. A bi-specific antibody of the invention comprises a binding molecule of the invention and at least one other antibody variable region (heavy and light chain) specific for another epitope on C2 or an epitope on a different molecule.

The fragment antigen-binding (Fab fragment) is a fragment of an antibody that binds to antigens. It is composed of one constant and one variable domain of each of the heavy and the light chain. These domains shape the antigen-binding site. The two variable domains bind the epitope on their specific antigens. Fab fragments can be generated in the laboratory. Various enzymes are presently available to cut the fragment from an antibody. In the present invention, the term Fab fragment relates to single variable domain Fab fragments and F(ab')2 fragment containing two variable domains. The term Fab fragment is used to reflect the fragment when split of an antibody, and to a similar fragment but produced directly as such from one or more a coding regions, expressed by a cell.

As used herein, the term "single chain Fv", also termed scFv, refers to engineered antibodies prepared by isolating the binding domains (both heavy and light chains) of a binding antibody, and supplying a linking moiety which permits preservation of the binding function. This forms, in essence, a radically abbreviated antibody, having only that part of the hyper-variable domain necessary for binding the antigen. Determination and construction of single chain antibodies are described in e.g. U.S. Pat. No. 4,946,778 to Ladner et al.

The term "$K_D$" (M), as used herein, is intended to refer to the dissociation equilibrium constant of a particular antibody-antigen interaction.

The heavy and light chain variable regions as specified SEQ ID NO: 2 and SEQ ID NO: 3; resp. are the heavy and light chain variable regions of the 5F2.4 antibody. The heavy and light chain variable regions as specified SEQ ID NO: 10 and SEQ ID NO: 11; resp. are the heavy and light chain variable regions of antibody 13. The heavy and light chain variable regions as specified SEQ ID NO: 18 and SEQ ID NO: 19; resp. are the heavy and light chain variable regions of the antibody 32. The heavy and light chain variable regions as specified SEQ ID NO: 26 and SEQ ID NO: 27; resp. are the heavy and light chain variable regions of the antibody 35. The heavy and light chain variable regions as specified SEQ ID NO: 34 and SEQ ID NO: 35; resp. are the heavy and light chain variable regions of the antibody 60. The light chain variable region as specified SEQ ID NO: 96 is a consensus mouse amino acid sequence of the light chain variable region of the antibody 5F2.4. The heavy chain variable region as specified SEQ ID NO: 97 is the consensus mouse amino acid sequence of the heavy chain variable region of the antibody 35. The heavy chain variable region as specified SEQ ID NO: 98 is the consensus mouse amino acid sequence of the heavy chain variable region of the antibody 60. SEQ ID NO: 99-102 are amino acid sequences of humanized light chain variable regions VL1-4 of 5F2.4. SEQ ID NO: 103-106 are amino acid sequences of humanized heavy chain variable regions VH1-4 of 5F2.4. SEQ ID NO: 107-110 are cDNA sequences coding for humanized light κ chain 5F2.4 containing humanized VL1-VL4. SEQ ID NO: 111-114 are cDNA sequences coding for humanized IgG4 chain 5F2.4 containing humanized VH1-VH4. SEQ ID NO: 115-118 are amino acid sequences coding for humanized light κ chain 5F2.4 containing humanized VL1-VL4. SEQ ID NO: 119-122 amino acid sequence coding for humanized IgG4 chain 5F2.4 containing humanized VH1-VH4.

An immunoglobulin light or heavy variable region in the binding molecule of the invention can have the amino acid sequence of SEQ ID NO: 2; 3; 10; 11; 18; 19; 26; 27; 34; 35; 96-106 and 115-122 with 1-5 amino acid substitutions. A binding molecule of the invention with such substituted heavy chain variable region, substituted light chain variable region or both has the same C2 antigen binding characteristics in kind, not necessarily in amount. The binding molecule binds to the same epitope as the original binding molecule. The 1-5 amino acid substitutions allow among others for the generation of deImmunized version of the binding molecule. Deimmunization for use in human subjects can typically be achieved by modifying the heavy chain at a maximum of 5 places, the light chain at a maximum of 5 places or both. Deimmunization of a murine variable region is an established technology and always yields a binding molecule with a decreased probability of inducing an immune response in a human. The number of amino acid substitutions that are required to achieve this result is typically less than 5 in each chain. Often the substitution of 1, 2 or 3 amino acids in each chain is sufficient for obtaining a binding molecule of the invention with a decreased probability of inducing an immune response in a human when compared to the unmodified sequence(s).

In a preferred embodiment the antibody of the invention is a human or humanized antibody. As used herein, the term "human antibody" is intended to include antibodies having variable and constant regions derived from human germline immunoglobulin sequences. The human antibodies may include amino acids residues not encoded by human germline immunoglobulin sequences, e.g. mutations introduced by random or site-specific mutagenesis in vitro or by somatic mutation in vivo.

As used herein, the term "humanized antibody" means that at least a portion of the framework regions of an immunoglobulin or engineered antibody construct is derived from human immunoglobulin sequences. It should be clear that any method to humanise antibodies or antibody constructs, as for example by variable domain resurfacing (Roguska et al., Proc Natl Acad Sci USA 1994, 91: 969) or CDR grafting or reshaping (Hurle et al., Curr Opin Biotechnol 1994, 5: 428), can be used. The humanised antibody preferably comprises the CDR regions of antibody 5F2.4, 13, 32, 35 or 60 in the context of an otherwise human antibody framework. The invention thus also provides a human antibody comprising a human heavy chain variable region with the CDR1-3 sequence of SEQ ID NO: 4-6 and a human light chain variable region with the CDR1-3 sequence of SEQ ID NO: 7-9. The grafted CDR sequences are of course appropriately positioned, i.e. the CDR1 region of the heavy chain variable region of SEQ ID NO: 4 takes the place of the CDR1 region of the heavy chain variable region of the human antibody used for the grafting process. The CDR2 region of SEQ ID NO: 5 takes the place of the CDR2 region of the heavy chain variable region of said human antibody and so on. The invention also provides a human antibody comprising a human heavy chain variable region with the CDR1-3 sequence of SEQ ID NO: 12-14 and a human light chain variable region with the CDR1-3 sequence of SEQ ID NO: 15-17. The CDR regions are again appropriately positioned. The invention also provides a human antibody comprising a human heavy chain variable region with the CDR1-3 sequence of SEQ ID NO: 20-22 and a human light chain variable region with the CDR1-3 sequence of SEQ ID NO: 23-25. The CDR regions are again appropriately positioned. The invention also provides a human antibody comprising a human heavy chain variable region with the CDR1-3 sequence of SEQ ID NO: 28-30 and a human light chain variable region with the CDR1-3 sequence of SEQ ID NO: 31-33. The CDR regions are again appropriately positioned. The invention also provides a human antibody comprising a human heavy chain variable region with the CDR1-3 sequence of SEQ ID NO: 36-38 and a human light chain variable region with the CDR1-3 sequence of SEQ ID NO: 39-41. The CDR regions are again appropriately positioned.

In a preferred embodiment the humanized light chain variable region in a human antibody comprising antibody 5F2.4 CDRs comprises the sequence of SEQ ID NO: 99, 100, 101 or 102 optionally with 1-5 amino acid substitutions. In a preferred embodiment the humanized heavy chain variable region in a human antibody comprising antibody 5F2.4 CDRs comprises the sequence of SEQ ID NO: 103, 104, 105 or 106 optionally with 1-5 amino acid substitutions. The amino acid substitutions, if any, are not in a CDR region.

In a preferred embodiment the human antibody comprising the CDRs of antibody 5F2.4 comprises a humanized light κ chain of SEQ ID NO: 115, 116, 117 or 118 optionally with 1-5 amino acid substitutions. The amino acid substitutions, if any, are not in a CDR region. In a preferred embodiment the human antibody comprising the CDRs of antibody 5F2.4 comprises a humanized IgG4 chain of SEQ ID NO: 119, 120, 121 or 122 optionally with 1-5 amino acid substitutions. The amino acid substitutions, if any, are not in a CDR region.

As used herein, the term "chimeric antibody" refers to an engineered antibody construct comprising of variable domains of one species (such as mouse, rat, goat, sheep, cow, lama or camel variable domains), which may be deimmunized, humanised or not, and constant domains of another species (such as non-human primate or human constant domains) (for review see Hurle et al., Curr Opin Biotechnol 1994, 5: 428). It should be clear that any method known in the art to develop chimeric antibodies or antibody constructs can be used.

As used herein, the term "Deimmunized" or "deimmunization" refers to the identification and subsequent removal of a T-cell epitope in a binding molecule of the invention. Typically, though not necessarily this is done in the variable region of an antibody of the invention. Again often, but not always necessary, this is done in a framework region and thus outside the CDR regions. Removal of a T-cell epitope is typically achieved by substituting one or more amino acids encoding the T-cell epitope. The sequence is thereby changed into a sequence different from a T-cell epitope. A deimmunized variable region typically contains 1-5 amino acid substitutions. The substituted amino acids are selected such that the tertiary structure of the variable region is not significantly altered. The substituted amino acid is therefore typically selected from the same group of amino acids (i.e. neutral, charged positive, charged negative, lipophilic). When available in the same group an amino acid is substituted for an amino acid that in a structurally close human antibody is at the same or similar position in the variable region.

The binding molecule of the invention is preferably a humanized or Deimmunized antibody.

An antibody of the invention is preferably an IgG, IgA, IgD, IgE or IgM antibody, such as IgG1, IgG2, IgG3 or IgG4 antibody.

In a preferred embodiment the constant regions of an antibody of the invention are the constant regions of an IgG, IgA, IgD, IgE or IgM antibody, such as IgG1, IgG2, IgG3 or IgG4 antibody. The constant regions may comprise modifications such as amino acid substitutions to confer specific properties to the constant regions. For instance, mutation of the IgG4 hinge region to render the antibody more stable towards the exchange of half-molecules. Other modifications affect half-life of the antibody, add or remove a glycosylation site, improve production, improve the homogeneity of the antibody product produced in large scale fermenters etc.

The entire constant part of an antibody light or heavy chain may comprise 0-5 amino acid substitutions when compared to a naturally occurring antibody. In some embodiments the constant part of a heavy or light chain contains 1-3 amino acid substitutions. An amino acid substitution in a constant region is preferably not with an amino acid of the same group (i.e. neutral, charged positive, charged negative, lipophilic).

In a preferred embodiment the constant regions of the antibody are the constant regions of a human antibody. In a preferred embodiment the antibody of the invention comprises the amino acid sequences of SEQ ID NO: 53 and SEQ ID NO: 54; SEQ ID NO: 55 and SEQ ID NO: 56; SEQ ID NO: 57 and SEQ ID NO: 58; SEQ ID NO: 57 and SEQ ID NO: 59; SEQ ID NO: 60 and SEQ ID NO: 61; or SEQ ID NO: 62 and SEQ ID NO: 63; wherein one or both of said sequences comprises 0-5 and when substituted preferably 1, 2 or 3 amino acid substitutions. The amino acid substitutions are preferably in the constant regions or the framework regions of the variable regions as indicated elsewhere herein.

In a preferred embodiment the antibody is a human or humanized antibody. In a preferred embodiment the antibody of the invention comprises the amino acid sequences of SEQ ID NO: 99 and one of amino acid sequence with SEQ ID NO: 103, 104, 105 or 106 wherein one or both of said sequences comprises 0-5 and preferably 1, 2 or 3 amino acid substitutions;

SEQ ID NO: 100 and one of amino acid sequence with SEQ ID NO: 103, 104, 105 or 106 wherein one or both of said sequences comprises 0-5 and preferably 1, 2 or 3 amino acid substitutions;

SEQ ID NO: 101 and one of amino acid sequence with SEQ ID NO: 103, 104, 105 or 106 wherein one or both of said sequences comprises 0-5 and when substituted preferably 1, 2 or 3 amino acid substitutions; or SEQ ID NO: 102 and one of amino acid sequence with SEQ ID NO: 103, 104, 105 or 106 wherein one or both of said sequences comprises 0-5 and when substituted preferably 1, 2 or 3 amino acid substitutions. The amino acid substitutions, if any, are not in the CDRs.

In a preferred embodiment the antibody of the invention comprises the amino acid sequences of SEQ ID NO: 115 and one of amino acid sequence with SEQ ID NO: 119, 120, 121 or 122 wherein one or both of said sequences comprises 0-5 and when substituted preferably 1, 2 or 3 amino acid substitutions;

SEQ ID NO: 116 and one of amino acid sequence with SEQ ID NO: 119, 120, 121 or 122 wherein one or both of said sequences comprises 0-5 and when substituted preferably 1, 2 or 3 amino acid substitutions;

SEQ ID NO: 117 and one of amino acid sequence with SEQ ID NO: 119, 120, 121 or 122 wherein one or both of said sequences comprises 0-5 and when substituted preferably 1, 2 or 3 amino acid substitutions; or SEQ ID NO: 118 and one of amino acid sequence with SEQ ID NO: 119, 120, 121 or 122 wherein one or both of said sequences comprises 0-5 and when substituted preferably 1, 2 or 3 amino acid substitutions. The amino acid substitutions, if any, are not in the CDRs. The amino acid substitutions are preferably in the constant regions or the framework regions of the variable regions as indicated elsewhere herein.

The invention further provides an antibody comprising the amino acid sequence of (b) SEQ ID NO: 115 and SEQ ID NO: 119; SEQ ID NO: 115 and SEQ ID NO: 120; SEQ ID NO: 115 and SEQ ID NO: 121; SEQ ID NO: 115 and SEQ ID NO: 122;

SEQ ID NO: 116 and SEQ ID NO: 119; SEQ ID NO: 116 and SEQ ID NO: 120; SEQ ID NO: 116 and SEQ ID NO: 121; SEQ ID NO: 116 and SEQ ID NO: 122;

SEQ ID NO: 117 and SEQ ID NO: 119; SEQ ID NO: 117 and SEQ ID NO: 120; SEQ ID NO: 117 and SEQ ID NO: 121; SEQ ID NO: 117 and SEQ ID NO: 122;

SEQ ID NO: 118 and SEQ ID NO: 119; SEQ ID NO: 118 and SEQ ID NO: 120; SEQ ID NO: 118 and SEQ ID NO: 121; or SEQ ID NO: 118 and SEQ ID NO: 122; or the amino acid sequences specified under (b) but wherein one or both of said sequences comprise 1-5 amino acid substitutions. The amino acid substitutions (if any) are not in the CDRs.

An antibody of the invention is preferably a murine IgG1 or IgG2a, a human IgG1 mutated in the constant region to reduce or prevent complement activation or Fc receptor interactions, or a human IgG4, or a human IgG4 mutated to prevent the exchange of half-molecules with other IgG4 molecules and/or mutated in the constant region to reduce or prevent Fc receptor interactions.

In some embodiments the antibody of the invention comprises two non-identical heavy chain constant regions and or non-identical light chain constant regions. Typically, though not necessarily, the non-identical constant regions differ from each other at no more than 5, preferably no more than 1-3 amino acid position. This is property is used in the field to produce for instance bi-specific antibodies and/or to provide further properties to the antibody.

The constant regions of an antibody of the invention are preferably human constant regions, preferably of one naturally occurring human antibody.

The invention further provides a nucleic acid molecule encoding a binding molecule or an antibody according to the invention. The invention further provides a nucleic acid encoding a CDR of the invention. Preferably encoding all of the CDRs of a variable light or variable heavy chain of antibody 5F2.4; antibody 13, antibody 32, antibody 35 or antibody 60. The nucleic acid preferably comprises the nucleic acid sequence of SEQ ID NO: 42; SEQ ID NO: 43; SEQ ID NO: 44; SEQ ID NO: 45; SEQ ID NO: 46; SEQ ID NO: 47; SEQ ID NO: 48; SEQ ID NO: 49; SEQ ID NO: 50; SEQ ID NO: 51; SEQ ID NO: 52; SEQ ID NO:107; SEQ ID NO:108; SEQ ID NO:109; SEQ ID NO:110; SEQ ID NO:111; SEQ ID NO:112; SEQ ID NO:113; or SEQ ID NO:114. The nucleic acid molecule can be used to produce a binding molecule of the invention. Cell lines provided with the nucleic acid can produce the binding molecule/antibody in the laboratory or production plant. Alternatively, the nucleic acid is transferred to a cell in the body of an animal in need thereof and the binding molecule/antibody is produced in vivo by the transformed cell. The nucleic acid molecule of the invention is typically provided with regulatory sequences to the express the binding molecule in the cell. However, present day homologous recombination techniques have become much more efficient. These techniques involve for instance double stranded break assisted homologous recombination, using site specific double stranded break inducing nucleases such as TALEN. Such or analogous homologous recombination systems can insert the nucleic acid molecule into a region that provides one or more of the in cis required regulatory sequences.

The invention further provides a gene delivery vehicle or vector comprising a nucleic acid molecule according to the invention. The gene delivery vehicle or vector can be a plasmid or other bacterially replicated nucleic acid. Such a gene delivery vehicle or vector can be easily transferred to, for instance, producer cells. The gene delivery vehicle can also be a viral vector. Preferred viral vectors are adenoviral vectors, lentiviral vectors, adeno-associated viral vectors and retroviral vectors.

The invention further provides an isolated or recombinant cell, or in vitro cell culture cell comprising a nucleic acid molecule or vector according to the invention. The invention further provides an isolated or recombinant cell, or in vitro cell culture cell comprising a binding molecule and preferably an antibody according to the invention. Preferably said cell produces said binding molecule or antibody. In a preferred embodiment said cell is a hybridoma cell, a Chinese hamster ovary (CHO) cell, an NS0 cell or a PER-C6™ cell. In a particularly preferred embodiment said cell is a CHO cell. Further provided is a cell culture comprising a cell according to the invention. Various institutions and companies have developed cell lines for the large scale production of antibodies, for instance for clinical use. Non-limiting examples of such cell lines are CHO cells, NS0 cells or PER.C6™ cells. These cells are also used for other purposes such as the production of proteins. Cell lines developed for industrial scale production of proteins and antibodies are herein further referred to as industrial cell lines. The invention provides an industrial cell line comprising a nucleic acid molecule, a binding molecule and/or antibody according to the invention. The invention also provides a cell line developed for the large scale production of protein and/or antibody comprising a binding molecule or antibody of the invention. The invention also provides the use a cell line developed for the large scale production of a binding molecule and/or antibody of the invention.

The invention further provides a method for producing a binding molecule or an antibody of the invention comprising culturing a cell of the invention and harvesting said antibody from said culture. Preferably said cell is cultured in a serum free medium. Preferably said cell is adapted for suspension growth. Further provided is an antibody obtainable by a method for producing an antibody according to the invention. The antibody is preferably purified from the medium of the culture. Preferably said antibody is affinity purified.

A cell of the invention is for instance a hybridoma cell line, a CHO cell, an NS0 cell or another cell type known for its suitability for antibody production for clinical purposes. In a particularly preferred embodiment said cell is a human cell. Preferably a cell that is transformed by an adenovirus E1 region or a functional equivalent thereof. A preferred example of such a cell line is the PER.C6™ cell line or equivalent thereof. In a particularly preferred embodiment said cell is a CHO cell or a variant thereof. Preferably a variant that makes use of a Glutamine synthetase (GS) vector system for expression of an antibody.

The invention thus further provides a method for producing a binding molecule characterised in that a binding molecule according to invention or an antibody according to the invention is produced. Preferably the method further comprises comprising collecting said binding molecule and/or said antibody.

The invention further provides a binding molecule or antibody according the invention for use in the treatment of an individual suffering from excessive or over-active complement activity. The treatment results in alleviation of at least one of the symptoms associated with excessive or over-active complement activity in said individual.

When used herein the term "individual" refers to an animal, preferably a mammal. In a preferred embodiment the individual is a primate, more preferably the individual is a human.

The invention further provides a binding molecule or antibody of the invention for use in the treatment of an individual suffering from or at risk of suffering from an inflammatory disease, a neuro-inflammatory disease or ischemia-reperfusion (I/R) injury. The treatment results in alleviation of at least one of the symptoms associated with the inflammation, the neuro-inflammatory disease or ischemia-reperfusion injury, such as renal or myocardial dysfunction, hemolytic crisis and muscle weakness.

The invention further provides a binding molecule or antibody according for use according to the invention, wherein said individual is suffering from an antibody-mediated inflammation or ischemia-reperfusion injury such as acute myocardial infarction, stroke, sepsis, immune complex diseases as rheumatoid arthritis, systemic lupus erythematosus, vasculitis, multiple trauma, multifocal motor neuropathy, antibody-mediated rejection of a renal allograft, (auto)immune haemolytic anemia, cardiopulmonary bypass and other vascular surgery, idiopathic membranous nephropathy, Goodpasture's syndrome, and other.

The invention also provides a pharmaceutical composition comprising a binding molecule according or antibody according to the invention and a pharmaceutically acceptable carrier.

DETAILED DESCRIPTION OF THE INVENTION

The second component of human complement (C2) is a 90-100 kDa glycoprotein which participates in the classical and lectin pathways of complement activation. C2 can be activated by C1s of the classical pathway or by activated MASP2 of the lectin pathway. C2 binds to surface-bound C4b (in the presence of Mg2+) to form a C4bC2 complex, which then is cleaved by activated C1s or MASP2 into two fragments: a larger 70 kDa fragment C2a, which remains attached to C4b to form a C3-convertase C4bC2a, and a smaller 30 kDa N-terminal fragment C2b, which is released into the fluid phase. Once activated and bound to C4b, C2a constitutes the catalytic subunit of the C3/C5 convertases being able to cleave C3 and C5, respectively.

As many other plasma proteins, C2 has a modular structure. Starting from its N-terminus, C2 consists of three complement control protein (CCP1-3) modules (also known as short consensus repeats (SCR) or sushi-domain repeats), a von Willebrand factor type A (vWFA) domain containing a metal-ion-dependent adhesion site, and a serine protease (SP) domain (Arlaud et al., Adv Immunol 1998, 69: 249). Electron microscopy studies revealed that C2 consists of three domains. The three CCP modules (CCP1-3) together form the N-terminal domain, which corresponds to C2b. The vWFA domain constitutes the second domain and the SP domain makes up the third domain. The second and third domains together constitute the larger C2a portion of the molecule.

CCP modules are common structural motifs that occur in a number of proteins. These globular units consist of approximately 60 amino acid residues and are folded into a compact six- to eight-stranded β-sheet structure built around four invariant disulfide-bonded cysteine residues (Norman et al., J Mol Biol 1991, 219: 717). Neighboring CCP modules are covalently attached by poorly conserved linkers.

The initial binding of C2 to surface-bound C4b is mediated by two low-affinity sites, one on C2b (Xu & Volanakis, J Immunol 1997, 158: 5958) and the other on the vWFA domain of C2a (Horiuchi et al., J Immunol 1991, 47: 584). Though the crystal structure of C2b and C2a have been determined to 1.8 Å resolution (Milder et al., Structure 2006, 14: 1587; Krishnan et al., J Mol Biol 2007, 367: 224; Krishnan et al., Acta Cristallogr D Biol Crystallogr 2009, D65: 266), the exact topology and structure of the amino acid residues constituting the contact site(s) for C4 and C3 on C2 are unknown. Thus the amino acid residues of C2 involved in the interaction with C4 remain to be established (Krishnan et al., Acta Cristallogr D Biol Crystallogr 2009, D65: 266).

A monoclonal antibody, 3A3.3 against an epitope located on C2b, inhibited the binding of C2 to C4b (Oglesby et al., J Immunol 1988, 2: 926), indicating the presence of a C4b-binding site(s) on C2b. MAbs against the C2a part of C2 that inhibit the activity of C2 have been disclosed in US2011/0165169A1. The amino acid sequences of the epitopes for these mAbs have not been reported in the public domain. Hence, the amino acid sequences of human C2 involved in the binding of C2 to C4b remain to be identified.

The present invention discloses binding molecules capable of inhibiting complement activation via the classical pathway and/or lectin pathway by blocking the activity of C2. Said binding molecules are preferably human or humanized mAbs or binding fragments thereof that specifically binds to specific epitopes on C2. In a preferred embodiment the epitope is a functional epitope. A binding molecule of the invention prevents the generation of C3a, C3b and other complement activation products downstream of C2. A binding molecule of the invention inhibits the formation of membrane attack complex of complement induced by antibodies, and thereby protects cells sensitized with these antibodies from complement-mediated damage such as lysis. A binding molecule of the invention is therefore suited to treat individuals in which a complement activation mediated effect of an administered antibody, or an auto-antibody needs to be countered. An auto-antibody in this context is an antibody generated and produced by the individual itself.

A binding molecule of the invention inhibits the activation of classical pathway by (auto)antibodies by at least 50%. Preferably the activation of the classical pathway is inhibited by 70%, more preferably by 90%, more preferably by at least 95%. For the calculation of the activity of the classical pathway, reference is made to complement activity assays as described in Palarasay et al., Clin Exp Immunol 2011, 164: 388 or to measurements as the determination the CH50 titer. The activity of the classical pathway in the absence of a binding molecule of the invention is arbitrarily set to 100%.

A binding molecule of the invention inhibits the activation of complement by CRP or other molecules that recognize damage associated molecular patterns by at least 50%. Preferably the activation of the lectin pathway is inhibited by 70%, more preferably by 90%, more preferably by at least 95%. For the calculation of the activity of the lectin pathway, reference is made to Palarasay et al., Clin Exp Immunol 2011, 164: 388. The activity of the lectin pathway in the absence of a binding molecule of the invention is arbitrarily set to 100%.

A binding molecule of the invention does not significantly inhibit the activation of the alternative pathway of complement activation. For the calculation of the activity of the alternative pathway, reference is made to an activity assay as described in Palarasay et al., Clin Exp Immunol 2011, 164: 388 or to the determination of AP50 activity. The activity of the alternative pathway in the absence of a binding molecule of the invention is arbitrarily set to 100%. A C2 binding molecule does not significantly or does not essentially inhibit the alternative pathway if the activity of the pathway is reduced by not more than 20% in the presence of otherwise saturating amounts of binding molecule.

Now that the invention has shown the advantageous properties of a binding molecule of the invention, it is possible for the skilled person to develop other binding molecules that bind the same epitope. The invention thus also provides a binding molecule that binds to C2 and that blocks the binding of an antibody comprising an immunoglobulin heavy chain variable region and an immunoglobulin light chain variable region comprising the amino acid sequences of SEQ ID NO: 2 and SEQ ID NO: 3 resp.; SEQ ID NO: 2 and SEQ ID NO: 96 resp.; SEQ ID NO: 10 and SEQ ID NO: 11 resp.; SEQ ID NO: 18 and SEQ ID NO: 19 resp.; SEQ ID NO: 26 and SEQ ID NO: 27 resp.; SEQ ID NO: 97 and SEQ ID NO: 27 resp.; SEQ ID NO: 34 and SEQ ID NO: 35 resp.; or SEQ ID NO: 98 and SEQ ID NO: 35 resp. The invention further provides the use of a binding molecule of the invention, preferably an antibody comprising an immunoglobulin heavy chain variable region and an immunoglobulin light chain variable region comprising the amino acid sequences of SEQ ID NO: 2 and SEQ ID NO: 3 resp.; SEQ ID NO: 2 and SEQ ID NO: 96 resp.; SEQ ID NO: 10 and SEQ ID NO: 11 resp.; SEQ ID NO: 18 and SEQ ID NO: 19 resp.; SEQ ID NO: 26 and SEQ ID NO: 27 resp.; SEQ ID NO: 97 and SEQ ID NO: 27 resp.; SEQ ID NO: 34 and SEQ ID NO: 35 resp.; or SEQ ID NO: 98 and SEQ ID NO: 35 resp. for identifying a binding molecule of the invention in a collection of binding molecules. An identified binding molecule is preferably characterised in that the sequence is determined of the binding molecule and/or the nucleic acid sequence encoding the binding molecule. This allows among others the production and further use of the binding molecule.

The invention also provides a method for identifying a binding molecule according to the invention comprising the step of testing the capability of a test binding molecule comprising a heavy chain and a light chain variable region to bind to C2 in the presence and absence of a known binding molecule of the invention. A test binding molecule is identified to be a binding molecule of the invention when the test binding molecule binds C2 in the absence of the known binding molecule of the invention and binds at least 50% or less to C2 when C2 is pre-incubated with the known binding molecule of the invention.

The invention further provides a binding molecule that binds C2 and that recognizes an epitope on C2a and an epitope on C2b. The antibody preferably comprises identical antigen binding variable regions. The invention further provides a binding molecule that binds C2 and that binds C2a and C2b individually. For the purpose of the this embodiment a size fraction by gel-electrophoresis of C1s digested C2 is considered to render the two fragments sufficiently separated from each other to consider the bands in the lane, individual representations of the C2a and C2b fragments.

A binding molecule and preferably a bi-valent monoclonal antibody of the invention binds C2 with a dissociation constant (RD) of less than 10e-7 M, preferably less than 10e-8 M, preferably less than 10e-9 M, more preferably less than 10e-10 M and more preferably less than 10e-11 M.

A binding molecule of the invention can be used for inhibiting the activation of the classical and/or lectin pathways. This in turn inhibits the generation of the biologically active, complement-derived peptides such as C4a and C4b, C3a, C3b, C5a and others in plasma or the body of an individual or otherwise complement functional system. The binding molecule prevents at least in part damaging effects of these complement-derived peptides on cells and tissues. A binding molecule of the present invention can be used for the preparation of a medicament for attenuating clinical signs and symptoms of human diseases by inhibiting complement activation in vivo. The mAbs molecules can be used alone or in combination with another drug for the treatment of complement mediated disease or symptoms.

Diseases that can be treated or prevented by a method or binding molecule of the invention are preferably autoimmune diseases such as experimental allergic neuritis, type II collagen-induced arthritis, myasthenia gravis, haemolytic anaemia, glomerulonephritis, idiopathic membranous nephropathy, rheumatoid arthritis, systemic lupus erythematosus, immune complex-induced vasculitis, adult respiratory distress syndrome, stroke, xenotransplantation, multiple sclerosis, burn injuries, extracorporeal dialysis and blood oxygenation, inflammatory disorders, including sepsis and septic shock, toxicity induced by the in vivo administration of cytokines or mAbs, antibody-mediated rejection of allografts such as kidney allografts, multiple trauma, ischemia-reperfusion injuries, myocardial infarction.

Individuals suffering from a disease involving complement-mediated damage or at risk of developing such complement-mediated damage can be treated by administering a binding molecule of the invention to an individual in need thereof. Thereby the biologically active complement-derived peptides are reduced in the individual and the lytic and other damaging effects of complement on cells and tissues is attenuated or prevented. By "effective amount" is meant an amount of binding molecule of the invention that is capable of inhibiting complement activation in the individual.

Treatment (prophylactic or therapeutic) will generally consist of administering the binding molecule of the invention parenterally together with a pharmaceutical carrier, preferably intravenously or subcutaneously. The dose and administration regimen of the binding molecule of the invention will depend on the extent of inhibition of complement activation aimed at. Typically, for binding molecules of the invention that are antibodies, the amount will be in the range of 2 to 20 mg per kg of body weight. For parenteral administration, the binding molecule will be formulated in an injectable form combined with a pharmaceutically acceptable parenteral vehicle. Such vehicles are well-known in the art and examples include saline, dextrose solution, Ringer's solution and solutions containing small amounts of human serum albumin.

Typically, the binding molecule of the invention will be formulated at a concentration of from about 20 mg to about 100 mg per ml. In one embodiment of this invention the binding molecule is administered by intravenous injection.

It should be understood that intended to come within the scope of this invention is virtually every method of administering mAbs or fragments thereof as described by the present invention, to yield sufficiently high levels either in the circulation or locally.

A pharmaceutical composition of the invention may be formulated with pharmaceutically acceptable carriers or diluents as well as any other known adjuvants and excipients in accordance with conventional techniques such as those disclosed in (Remington: The Science and Practice of Pharmacy, 19th Edition, Gennaro, Ed., Mack Publishing Co., Easton, Pa., 1995).

The term "pharmaceutically acceptable carrier" relates to carriers or excipients, which are inherently non-toxic. Examples of such excipients are, but are not limited to, saline, Ringer's solution, dextrose solution and Hank's solution. Non-aqueous excipients such as fixed oils and ethyl oleate may also be used.

The pharmaceutical composition is preferably administered parenterally, preferably by intra-venous or subcutaneous injection or infusion.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intra-peritoneal, transtracheal, subcutaneous, subcuticular, intraarticular, subcapsular, subarachnoid, intraspinal, epidural and intrasternal injection and infusion.

Pharmaceutical compositions typically must be sterile and stable under the conditions of manufacture and storage. The composition can be formulated as a solution, micro-emulsion, liposome, or other ordered structure suitable to high drug concentration. Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The pharmaceutical compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol, sorbic acid, and the like. It may also be desirable to include isotonicity agents, such as sugars, polyalcohols such as mannitol, sorbitol, glycerol or sodium chloride in the compositions. Pharmaceutically-acceptable antioxidants may also be included, for example (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Sterile injectable solutions can be prepared by incorporating the mAb in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Prolonged absorption of the injectable anti-C2 mAbs or fragments thereof can be brought about by including in the composition an agent that delays absorption, for example, monostearate salts and gelatin.

The mAbs of fragments thereof can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such formulations are generally known to those skilled in the art. See, e.g., Sustained and Controlled Release Drug Delivery Systems, J. R. Robinson, ed., Marcel Dekker, Inc., New York, 1978.

The pharmaceutical compositions can be administered with medical devices known in the art.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation.

Actual dosage levels of the mAbs or fragments thereof in the pharmaceutical compositions of the present invention may be varied so as to obtain an amount of the active ingredient which is effective to achieve the desired therapeutic response for a particular patient without being toxic to the patient.

In one embodiment, the binding molecules, in particular antibodies, according to the invention can be administered by infusion in a weekly dosage of from 10 to 500 $mg/m^2$, such as of from 200 to 400 $mg/m^2$. Such administration can be repeated, e.g., 1 to 8 times, such as 3 to 5 times. The administration may be performed by continuous infusion over a period of from 2 to 24 hours, such as of from 2 to 12 hours.

In yet another embodiment, the mAbs or fragments thereof or any other binding molecules disclosed in this invention, can be administered by maintenance therapy, such as, e.g., once a week for a period of 6 months or more.

The present invention will now be illustrated with reference to the following examples, which set forth particularly advantageous embodiments. However, it should be noted that these embodiments are illustrative and are not to be construed as restricting the invention in any way.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1. Non-reducing SDS-PAGE of wild-type (lane 1) and deglycosylated (lane 2) recombinant human C2, C1s-cleaved C2 (lane 3), and deglycosylated C1s-cleaved C2 (lane 4). C1s cleavage was performed at C1s-to-C2 ratio of 1:25. Untreated and treated C2 was visualized with Coomassie brilliant blue. Identity of glycosylated C2 (≈100 kDa), glycosylated C2a (≈70 kDa) and glycosylated C2b (≈30 kDa) is indicated with arrowheads. Position of MW markers is also shown. * indicates PNGase enzyme.

FIG. 2. Principle of the ELISA to screen for inhibitory activity of the anti-C2 mAbs. Note that an inhibiting mAb will have no effect on C4 binding and will decrease C3 binding to aggregated IgG on the solid phase.

FIG. 3A. Example of screening results for inhibitory activity of anti-C2 hybridoma supernatants. Positive control is diluted serum without hybridoma supernatant. Negative control is diluted serum with EDTA and without hybridoma supernatant. Numbers on the X-axis refer to hybridoma number. Arrows indicate hybridoma supernatants that were negative in the anti-C2 ELISA and that were tested as controls.

FIG. 3B. Example of screening results for inhibitory activity of anti-C2 hybridoma supernatants.

FIG. 4. Binding of mouse anti-human complement C2 antibodies against recombinant human complement C2 at low (25 ng/well; grey symbols) or at high (200 ng/well; black symbols) coating. Results (absorption at 450 nm) are mean±SD, n=2.

Figure 5:
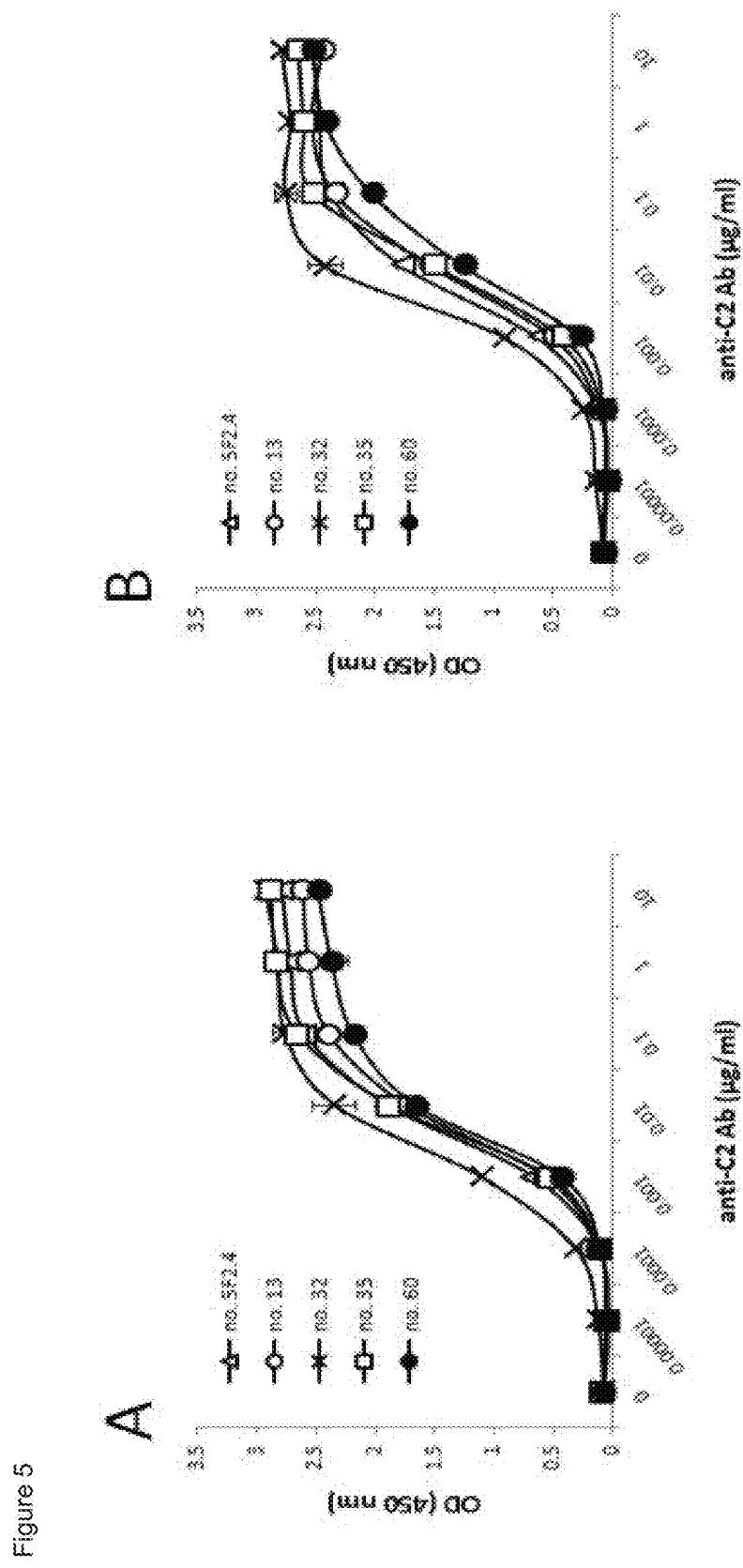

FIG. 5. Binding of mouse anti-C2 mAbs to wild-type (A) or C1s-cleaved recombinant human C2 (B). The protein mixtures were coated onto ELISA plates and incubated with various concentrations of anti-C2 mAbs. Results (absorption at 450 nm) are mean±SD, n=2.

Figure 6:
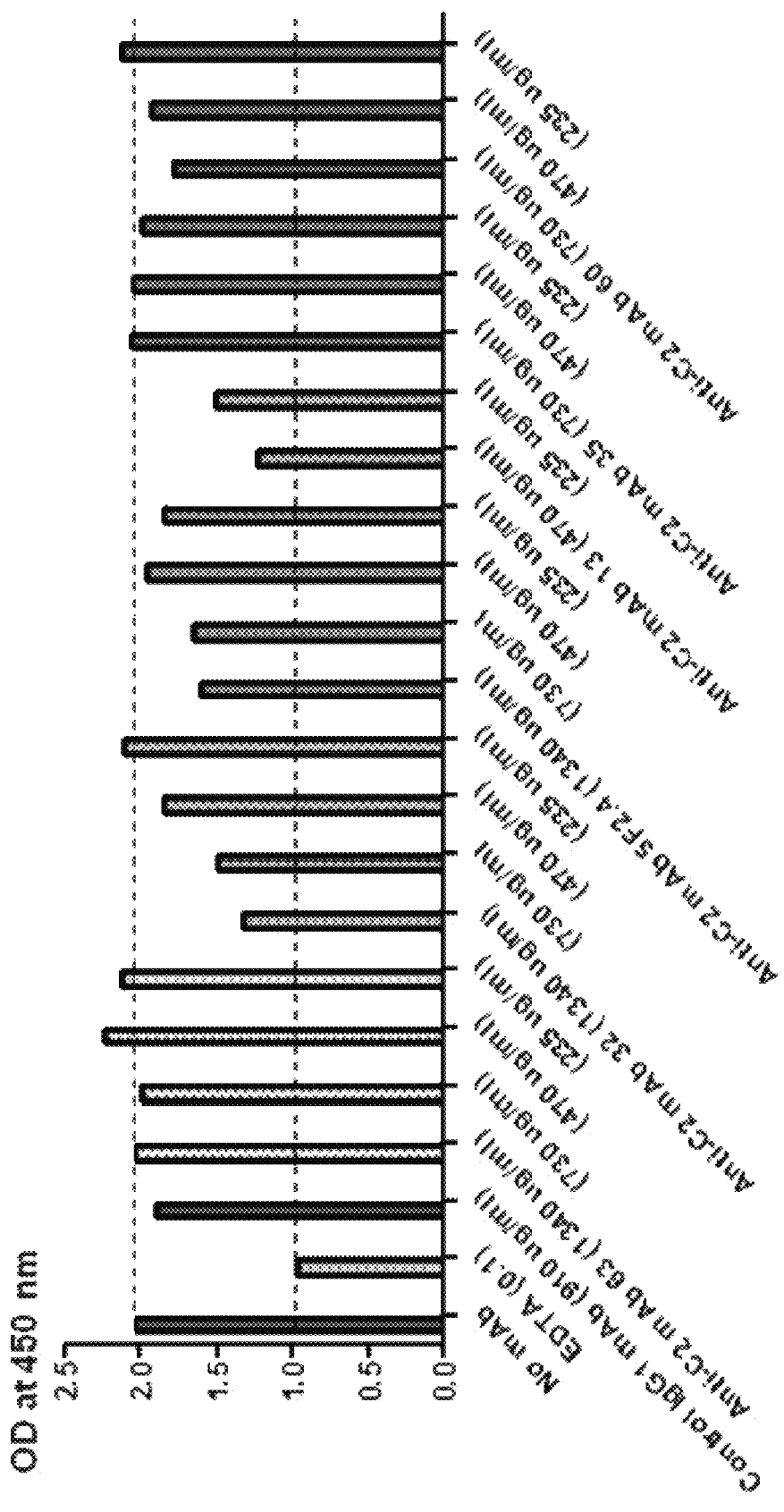

FIG. 6. Inhibition of C3 fixation to solid phase aggregated IgG by purified mouse anti-C2 mAbs. One volume of fresh human serum was incubated with one volume of mAb at the concentration indicated, diluted and tested. The dotted lines indicate fixation level in the absence of a mAb (upper line) and in the presence of EDTA (lower line).

Figure 7:
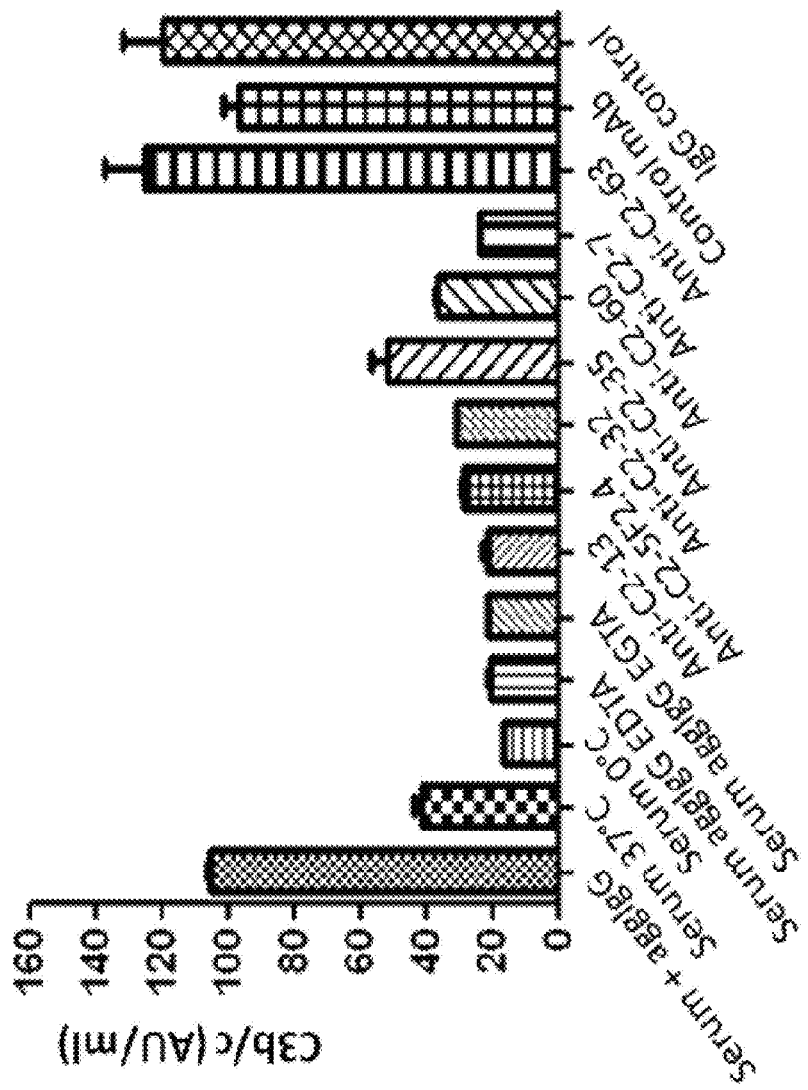

FIG. 7. Effect of anti-C2 mAbs on the activation of C3 by aggregated IgG in human serum. One volume of serum was mixed with one volume of mAb (0.48 mg/ml) and incubated with aggregated IgG at 1 mg per ml. Activated C3 was measured with ELISA as described in methods. Results are expressed as Arbitrary Units (AU) per ml.

Figure 8:
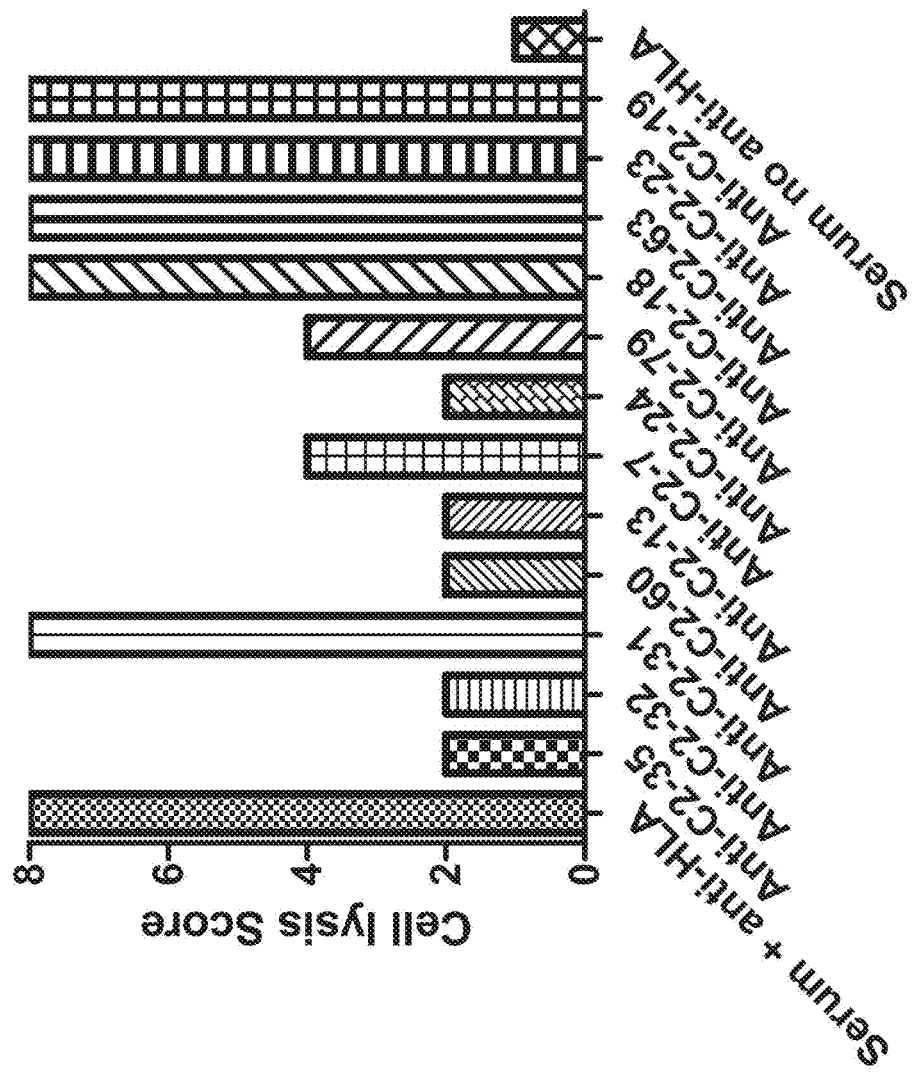

FIG. 8. Effect of anti-C2 mAbs on complement-dependent cytotoxicity of anti-HLA antibodies in a human ex vivo model for allograft rejection. One µl of serum with anti-HLA antibodies were incubated with 1 µl PBMC suspension ($2-5\times10^6$ cells/ml) for 1 hour at RT. Meanwhile 5 µl fresh normal serum were incubated with 15 µl VB and 5 µl VB containing anti-C2 mAb for 20 minutes at RT. Ten µl of each sample were incubated with the PBMC mixtures two hours at RT. Cytotoxicity was measured with Fluoroquench and assessed by microscopy. A cytotoxicity score of "0" means no lysis of the cells, whereas a score of 8 was given when >80% of the cells were lysed. Fresh serum without anti-C2 mAb was used as a positive control, EDTA as a negative control. MAb 5F2.4 is not shown in this figure though it also has an inhibitory effect in this assay. MAB anti-C2-79 also reduces cytotoxicity in this assay but has no inhibitory effect in other assays.

Figure 9A:
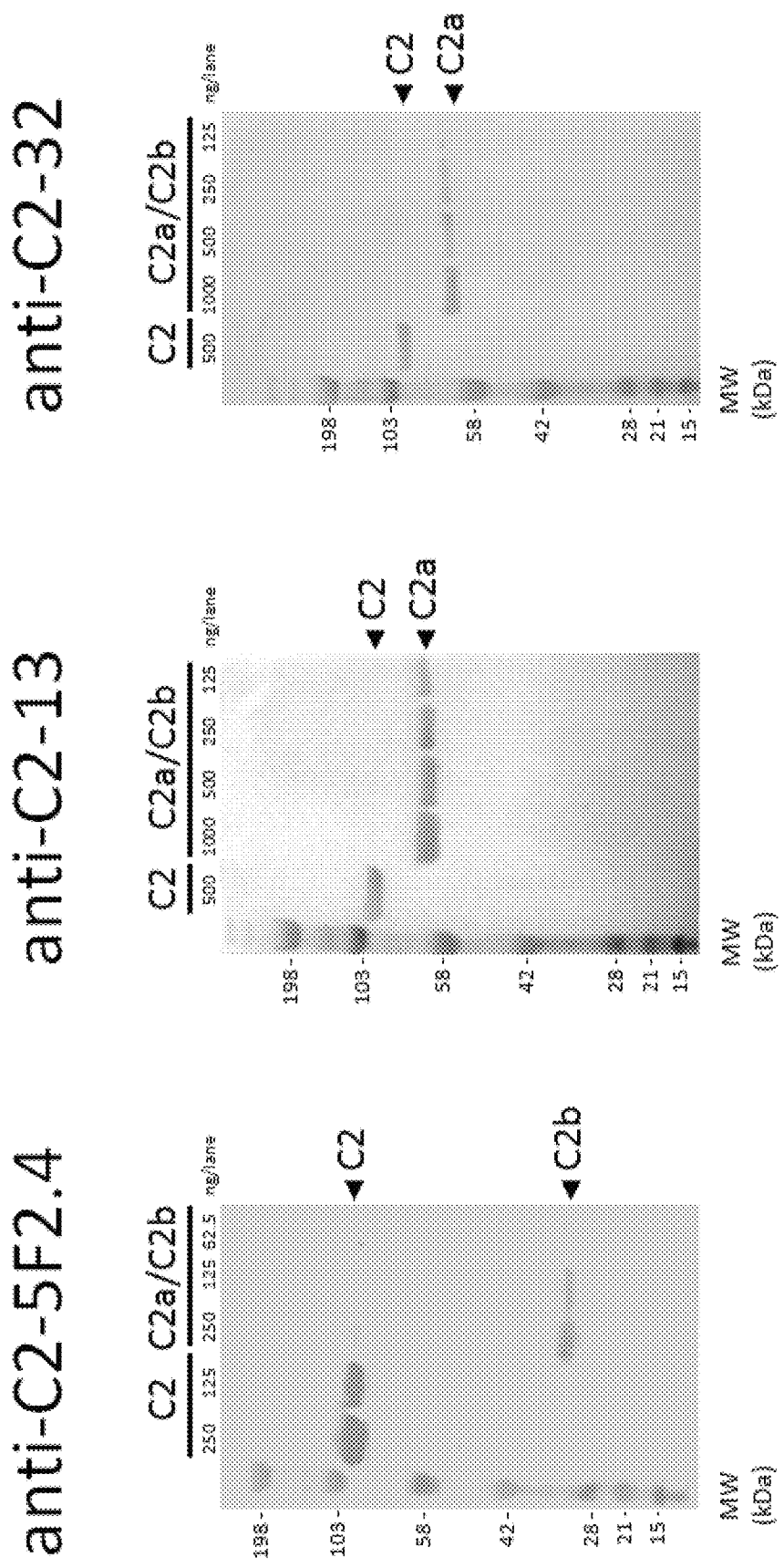

FIG. 9A. Location of epitopes on C2a or C2b recognized by anti-C2 mAbs using Western blotting of wild-type and C1s-cleaved recombinant human C2. Identity of C2 ($\approx$100 kDa), C2a ($\approx$70 kDa) and C2b ($\approx$30 kDa) is indicated with arrowheads. Detection was done with 100 ng/ml (anti-C2-5F2.4 and -35) or 200 ng/mL (anti-C2-13, -32 and -60) anti-C2 mAbs.

Figure 9B:
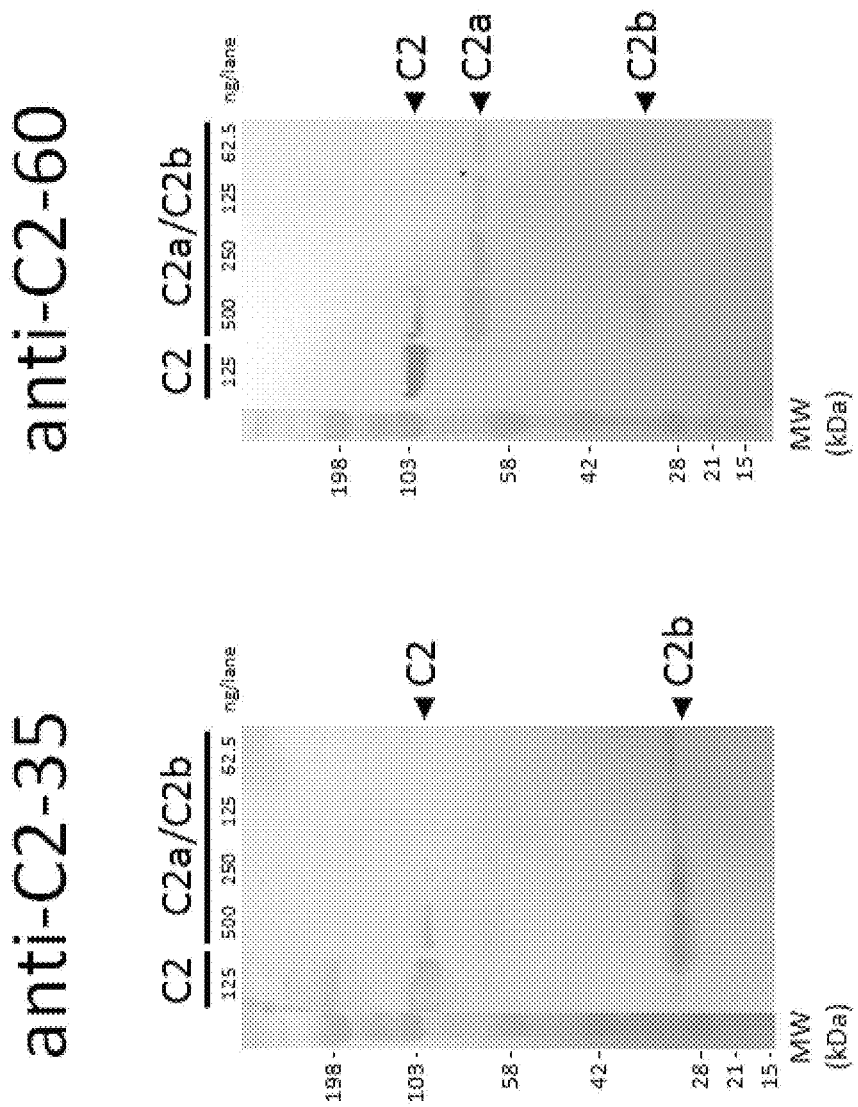

FIG. 9B. Location of epitopes on C2a or C2b recognized by anti-C2 mAbs using Western blotting of wild-type and C1s-cleaved recombinant human C2. Identity of C2 ($\approx$100 kDa), C2a ($\approx$70 kDa) and C2b ($\approx$30 kDa) is indicated with arrowheads. Detection was done with 100 ng/ml (anti-C2-35) or 200 ng/mL (anti-C2-60) anti-C2 mAbs.

Figure 10A:
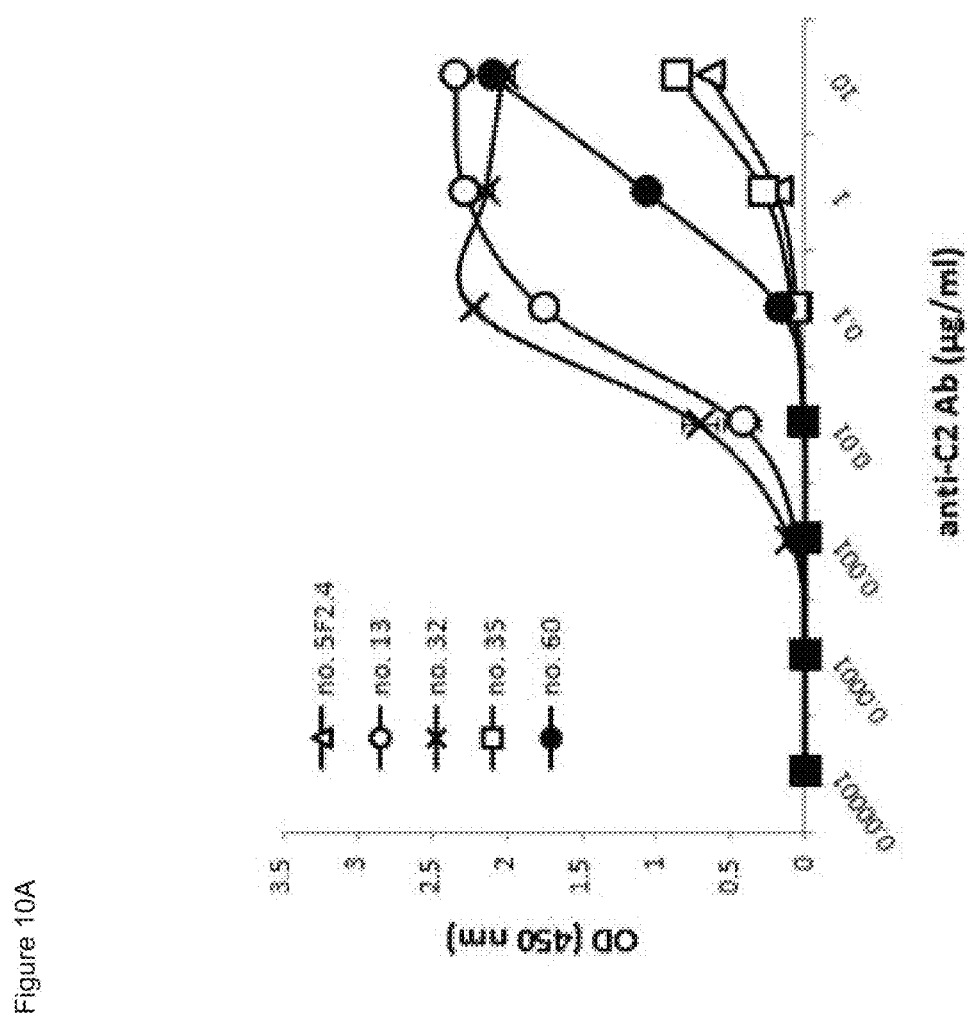

FIG. 10A. Binding of anti-C2 mAbs to recombinant human C2a purified with size-exclusion chromatography (A), and binding of anti-C2 mAb 5F2.4 to deglycosylated (non-denatured/non-reduced) recombinant human C2 (B), to denatured (non-reduced) or reduced (denatured) recombinant human C2 (C) as assessed in ELISA. Results (absorption at 450 nm) are mean±SD, n=2.

Figure 10B:
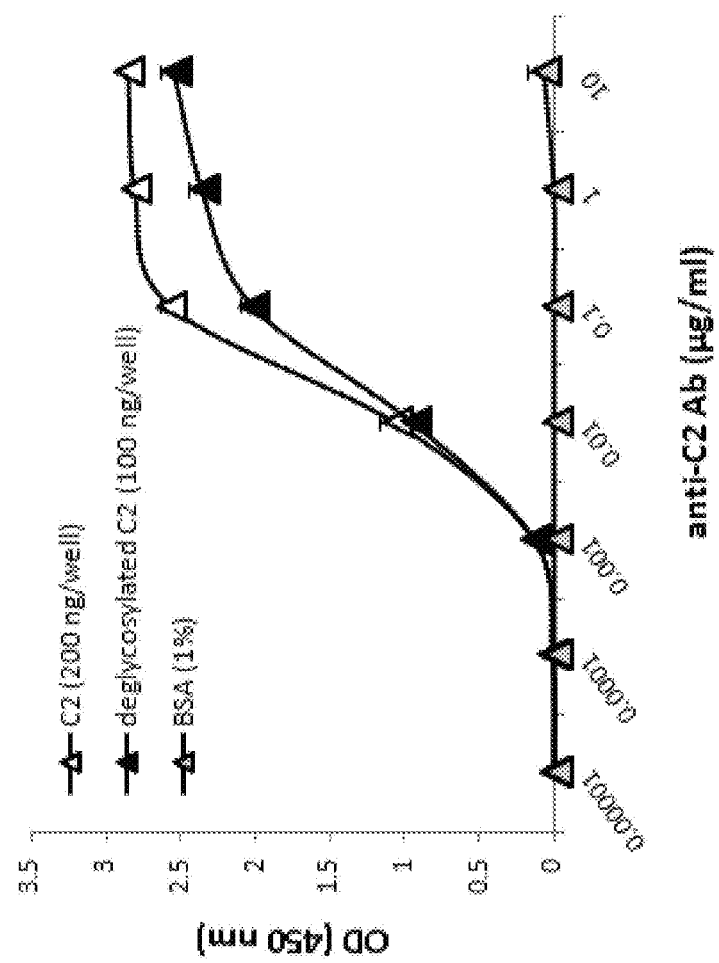

FIG. 10B. Binding of anti-C2 mAbs to recombinant human C2a purified with size-exclusion chromatography (A), and binding of anti-C2 mAb 5F2.4 to deglycosylated (non-denatured/non-reduced) recombinant human C2 (B), to denatured (non-reduced) or reduced (denatured) recombinant human C2 (C) as assessed in ELISA. Results (absorption at 450 nm) are mean±SD, n=2.

Figure 10C:
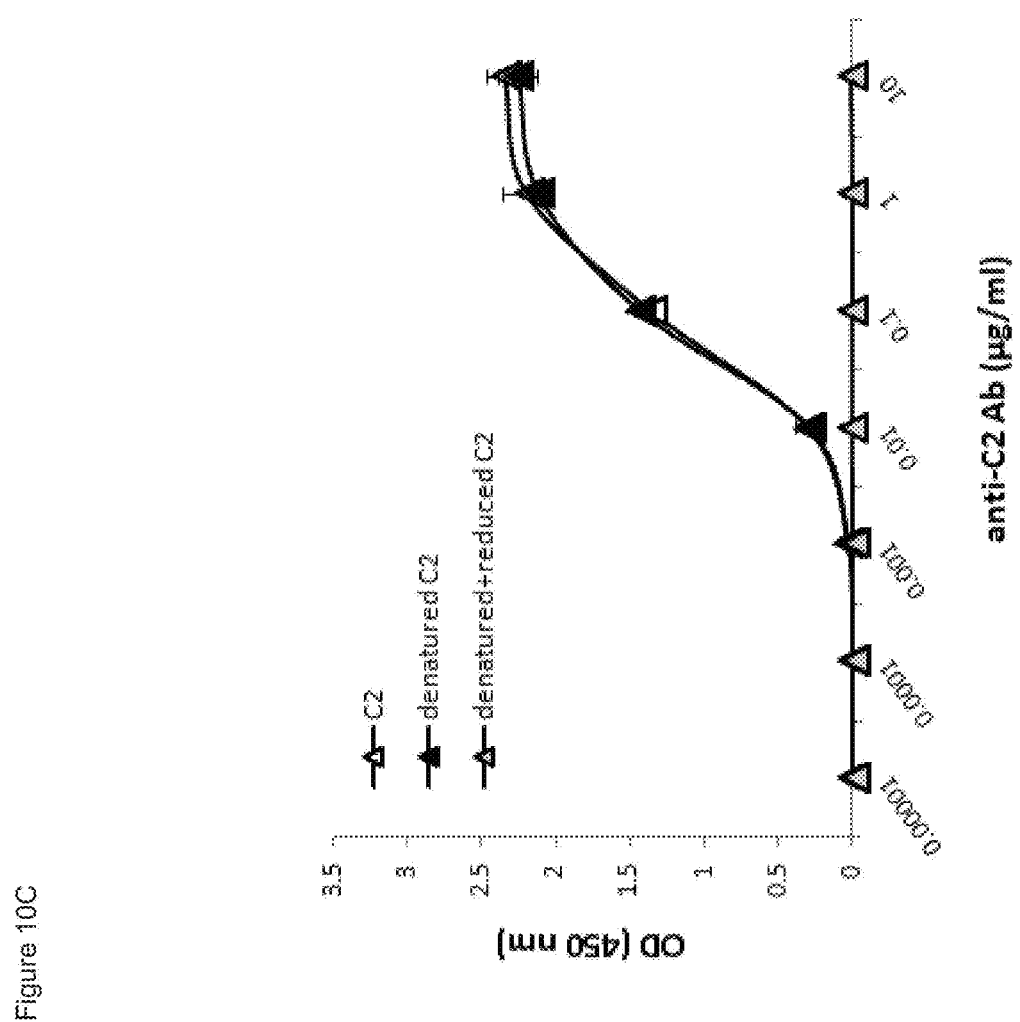

FIG. 10C. Binding of anti-C2 mAbs to recombinant human C2a purified with size-exclusion chromatography (A), and binding of anti-C2 mAb 5F2.4 to deglycosylated (non-denatured/non-reduced) recombinant human C2 (B), to denatured (non-reduced) or reduced (denatured) recombinant human C2 (C) as assessed in ELISA. Results (absorption at 450 nm) are mean±SD, n=2.

Figure 11:
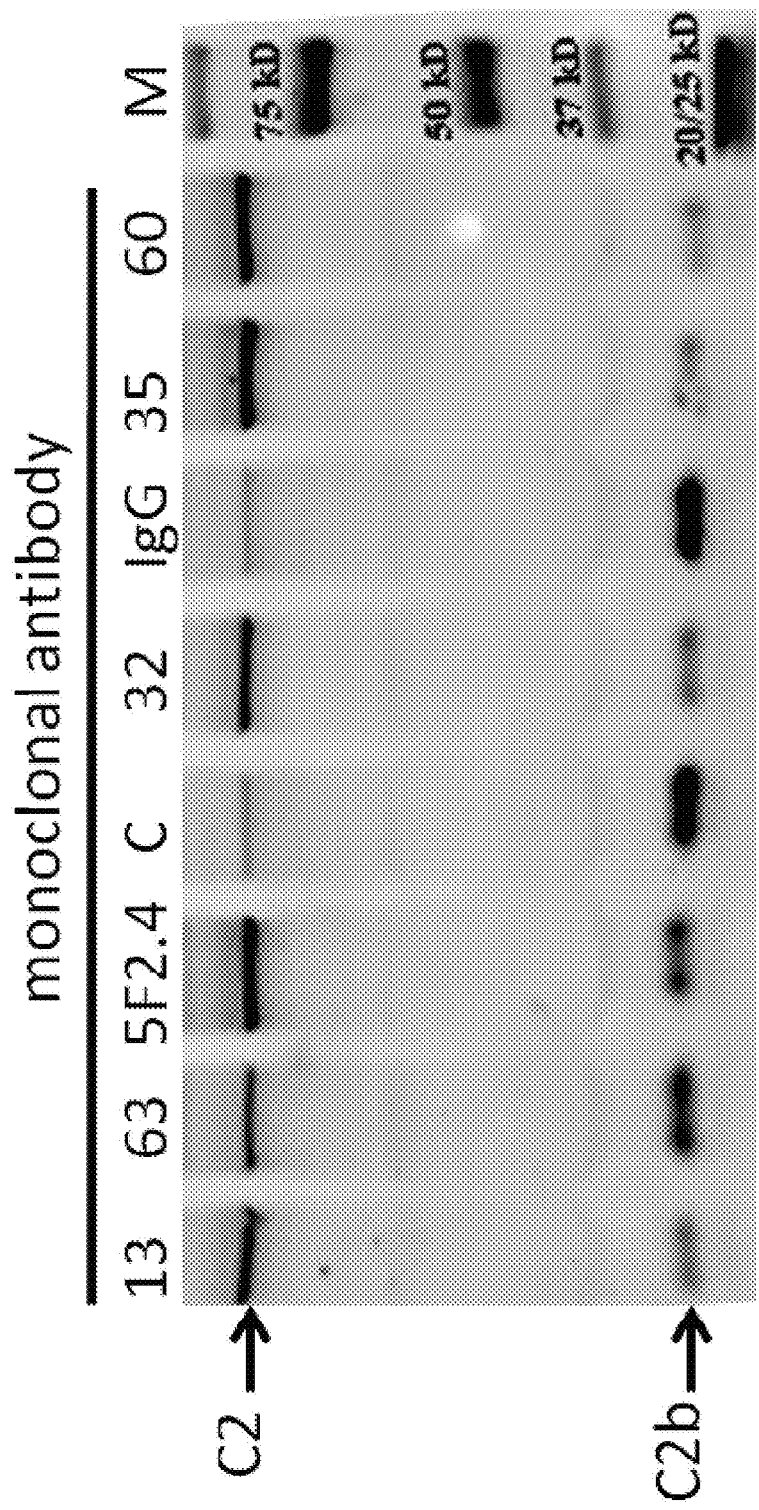

FIG. 11. Inhibitory anti-C2 mAbs prevent the cleavage of C2 during complement activation. 10 µl of serum with 10 µl of anti-C2 mAb (0.48 mg/ml) were incubated with 10 µl of aggregated IgG (1 mg/ml), and separated on 7.5% SDS-PAGE. Samples were blotted and incubated with biotinylated anti-C2-5F2.4 (binds to native C2 and to C2b) to assess cleavage of C2. Positions of the molecular weight markers (M) are indicated. Arrows indicate the positions of C2 and C2b as visualized by mAb anti-C2 5F2.4. C indicates serum incubated with aggregated IgG without anti-C2 added. IgG indicates serum incubated with aggregated IgG in the presence of polyclonal human IgG (0.48 mg/ml).

Figure 12:
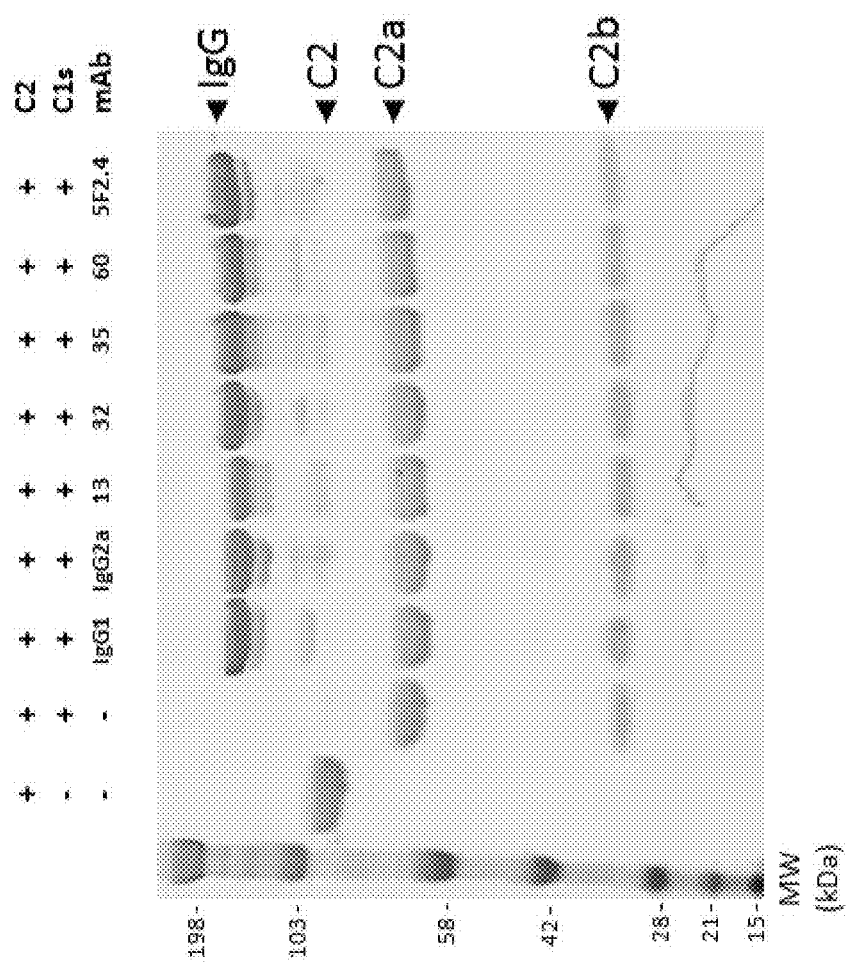

FIG. 12. Inhibitory anti-2 mAbs do not prevent the cleavage of fluid-phase wild-type recombinant human C2 by C1s. C2 was incubated with C1s in the presence of anti-C2 mAbs. Mixtures were analyzed with non-reducing SDS-PAGE and visualized with Coomassie brilliant blue. Identity of mouse IgG ($\approx$150 kDa), C2 ($\approx$100 kDa), C2a ($\approx$70 kDa) and C2b ($\approx$30 kDa) is indicated with arrowheads.

Figure 13:
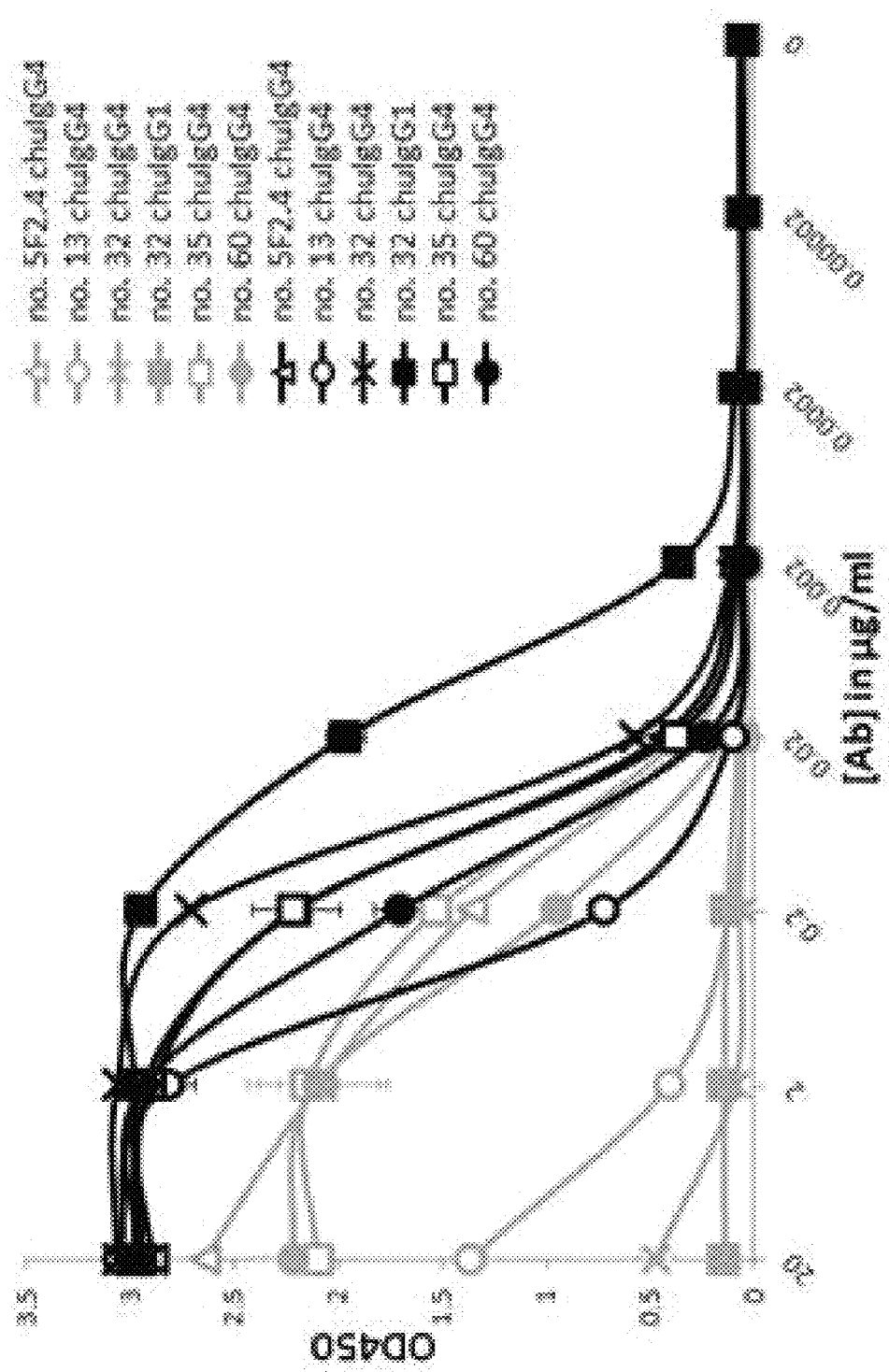

FIG. 13. Binding of chimeric mouse-human anti-human complement C2 antibodies against recombinant human complement C2 at low (25 ng/well; grey symbols) or at high (200 ng/well; black symbols) coating. Results (absorption at 450 nm) are mean±SD, n=2.

Figure 14:
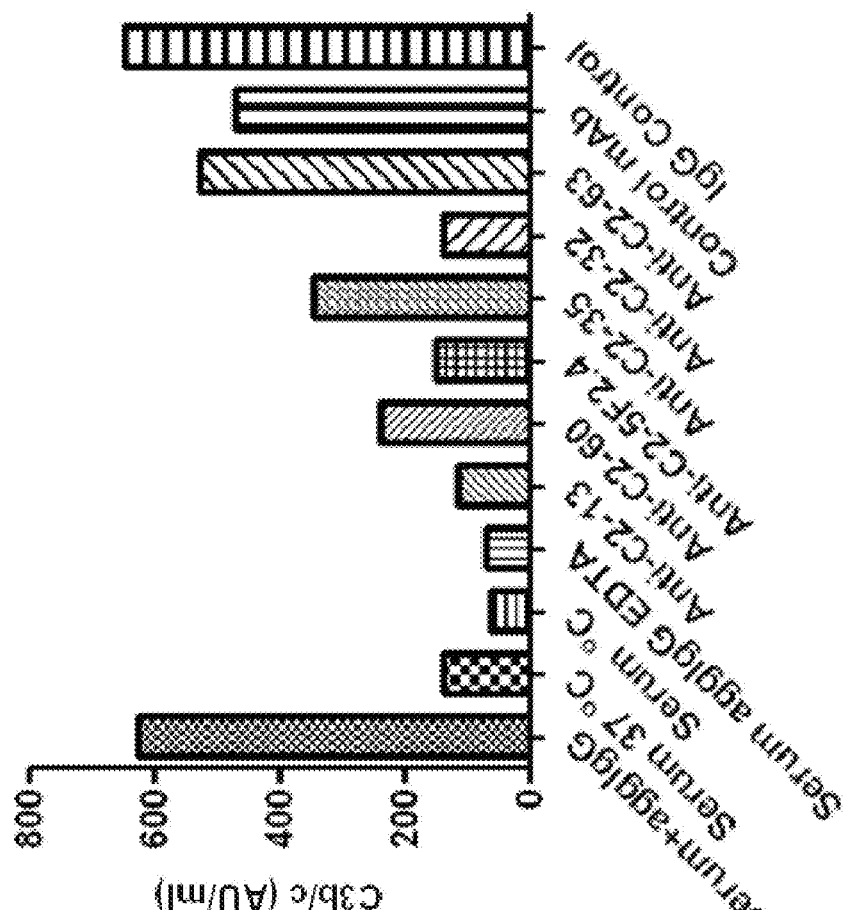

FIG. 14. Effect of mouse-human IgG4 chimeric anti-C2 mAbs on the activation of C3 by aggregated IgG in human serum. The experimental design is the same as in FIG. 6, except that the recombinant mouse-human IgG4 format of the anti-C2 mAbs were added to human serum instead of the murine format of the mAbs. Anti-C2-63 is a murine non-inhibitory mAb against human C2 that was tested as a control. Control mAb is a mAb against human factor XI. Control IgG is human IgG tested as control.

Figure 15:
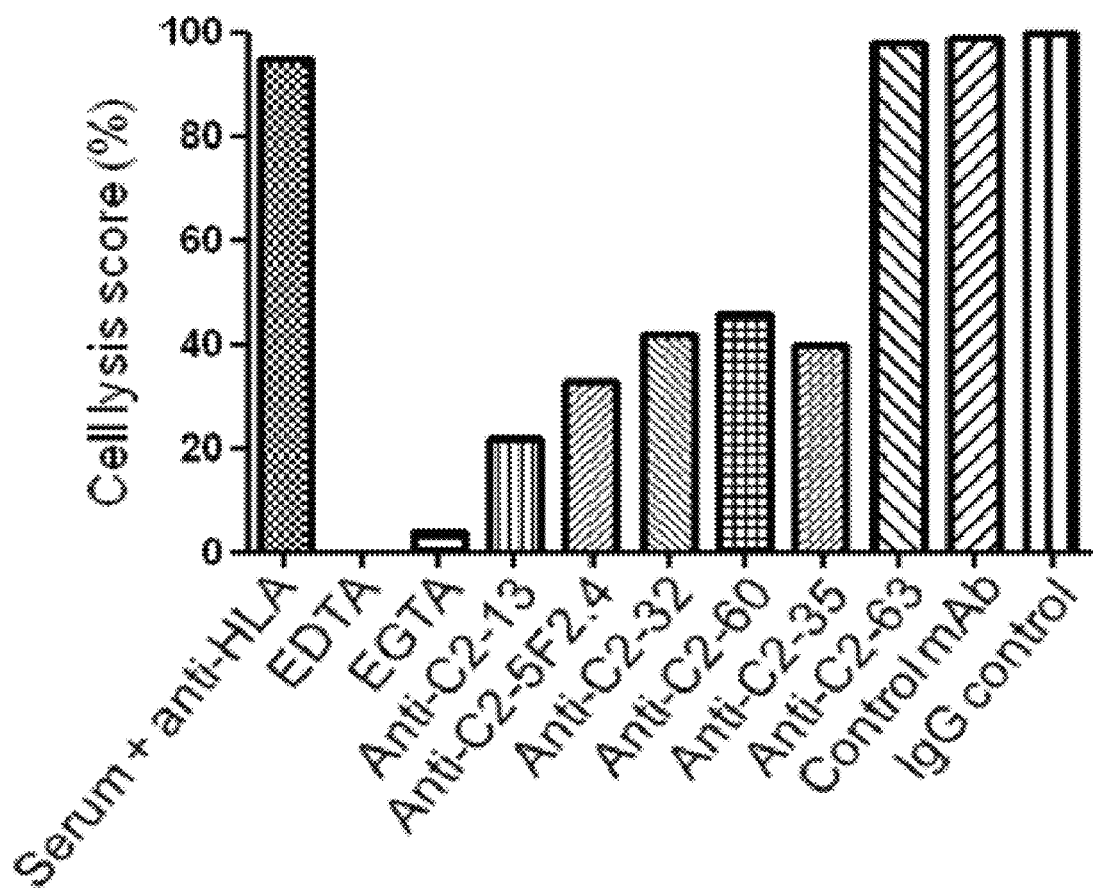

FIG. 15. Effect of the mouse-human IgG4 chimeric anti-C2 mAbs on complement-dependent cytotoxicity of anti-HLA antibodies in a human ex vivo model for allograft rejection. The experimental design is the same as in FIG. 8, except that the recombinant mouse-human IgG4 format of the anti-C2 mAbs were added to human serum instead of the murine format of the mAbs. Cytotoxicity was analysed with the program "Leica Q WIN" and expressed as % lysis. Anti-C2-63 is a murine non-inhibitory mAb against human C2 that was tested as a control. Control mAb is a mAb against human factor XI. Control IgG is human IgG tested as control.

FIGS. 16A-16Q. List of sequences.

Figure 17:
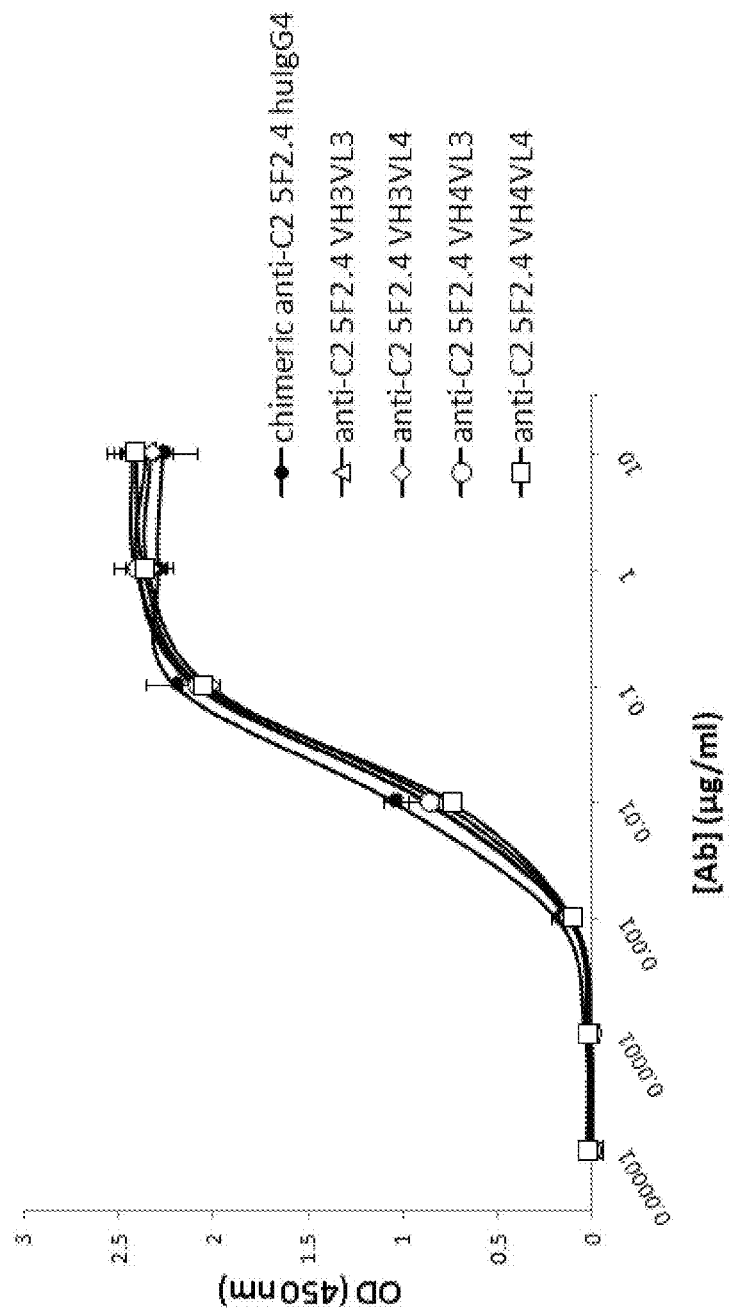

FIG. 17. Binding of humanized anti-human complement C2 antibodies against recombinant human complement C2 using ELISA. Results (absorption at 450 nm) are mean±SD, n=2.

Figure 18:
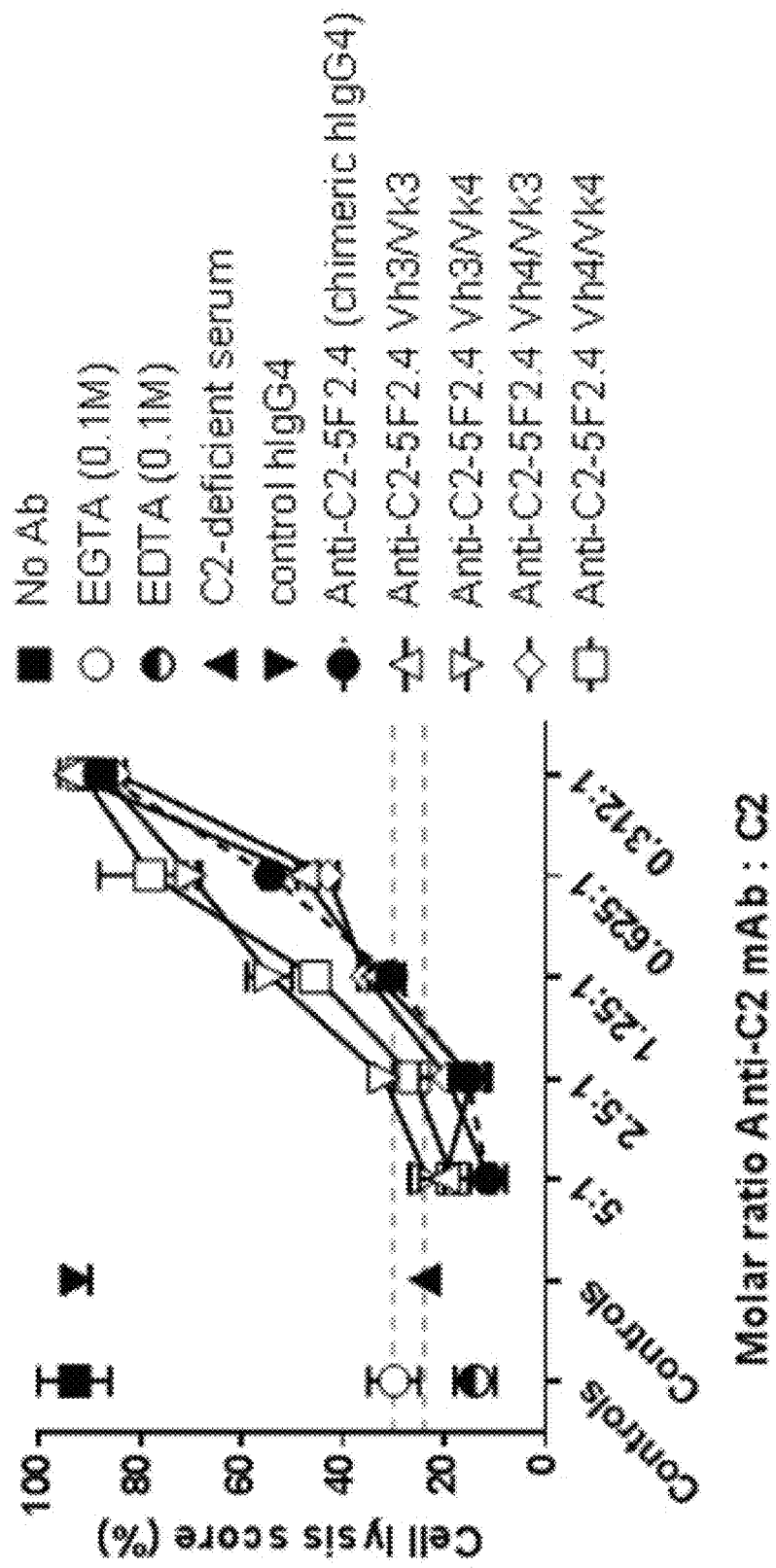

FIG. 18. Effect of humanized anti-C2 mAbs on complement-dependent cytotoxicity of anti-human HLA-A, B, C (clone: W6/32) antibody in a human ex vivo model for allograft rejection. One µl of W6/32 antibody solution (31.25 µg/ml) was incubated with 1 µl PBMC suspension ($5\times10^6$ cells/ml) for 30 min at 37° C. Meanwhile 10 µl fresh normal serum was incubated with 10 µl VB containing anti-C2 mAb for 30 minutes at RT. Five µl of each sample were incubated with the PBMC mixtures 1 hour at 37° C. Five µl Fluoroquench was added to each well, and samples were incubated for 30 minutes in the dark. Thereafter, cytotoxicity was measured by automated microscopy (Leica Micro Systems). The percentage lysis was calculated by Leica Q WIN software. Fresh serum without anti-C2 mAb was used as a positive control, EDTA and EGTA as negative controls. Further controls were an irrelevant human IgG4 mAb and C2-deficient serum. Results are mean±SEM, n=2.

Figure 19:
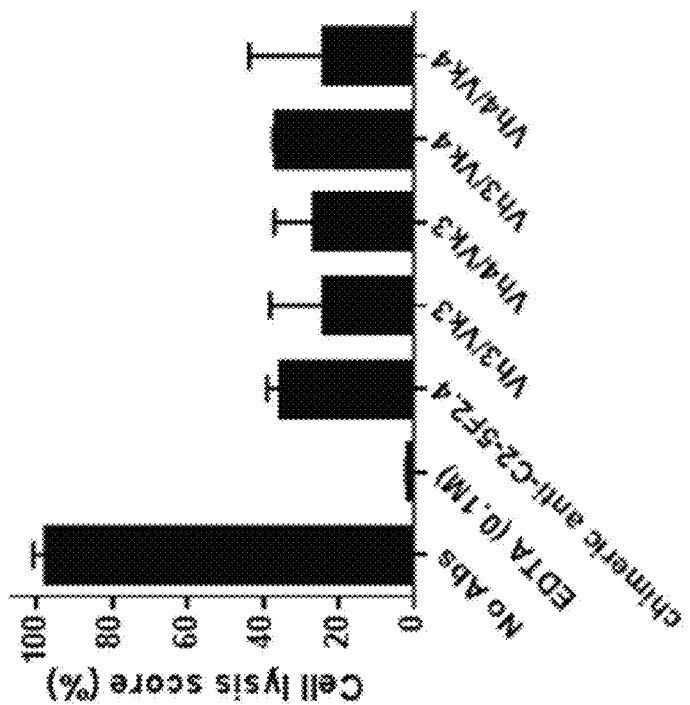

FIG. 19. Effect of humanized anti-C2 mAbs on complement-dependent cytotoxicity of serum anti-HLA antibodies in a human ex vivo model for allograft rejection. One μl of serum anti-HLA antibodies was incubated with 1 μl PBMC suspension (5×10$^6$ cells/ml) for 30 min at 37° C. Meanwhile 10 μl fresh normal serum was incubated with 10 μl VB containing anti-C2 mAb for 30 minutes at RT. Five μl of each sample were incubated with the PBMC mixtures 1 hour at 37° C. Five μl Fluoroquench was added to each well, and samples were incubated for 30 minutes in the dark. Thereafter, cytotoxicity was measured by automated microscopy (Leica Micro Systems). The percentage lysis was calculated by Leica Q WIN software. Fresh serum without anti-C2 mAb was used as a positive control, EDTA as a negative control. Results are mean±SD, n=2.

FIG. 20 shows binding characteristics of mAb anti-C2-5F2.4.

EXAMPLES

Those skilled in the art will recognize or be able to ascertain, using routine experimentation, many equivalents of the specific embodiments of the invention described herein. Such equivalents are intended to be encompassed by the following claims. Any combination of the embodiments disclosed in the dependent claims is also contemplated to be within the scope of the invention.

All patents, patent applications and scientific publications referred to herein that discuss various aspects of the materials and methods used to realise the invention are hereby incorporated in their entirety by reference.

Materials:

Aggregated IgG (aggIgG) was prepared by heating purified human IgG (Gammaquin, Sanquin, Amsterdam, The Netherlands) at 80 mg per ml in PBS for 20 minutes at 63° C. The preparation was then diluted to 10 mg per ml, and stored at −80° C. until used.

Fresh human serum was obtained from human volunteers by venous puncture and stored in aliquots at −80° C. Normal aged serum was prepared by incubating normal fresh serum for one week at 37° C. Serum deficient for C2 was purchased from Sigma-Aldrich.

Affinity purified chicken polyclonal anti-C3 and goat anti-C4 antibodies were purchased from Mybiosource.com and Thermo Scientific, respectively. The antibodies were bioninylated by using EZ-Link Sulfo-NHS-LC-Biotin (Thermo Scientific) according the manufacturers protocol. Briefly, a 20 M fold excess of biotin was added to the antibody and incubated for 30 minutes at room temperature. Next, the antibody was dialyzed overnight against PBS and stored at 4° C. until further use.

Peripheral blood mononuclear cells (PBMCs) were isolated from heparin blood by Ficoll-Paque (buoyant density 1.077 g/mL; GE Healthcare) centrifugation. Isolated cells were washed with phosphate buffered saline (PBS) at room temperature and kept in RPMI medium at 4° C. until further use.

Example 1: Generation of Mouse Anti-Human Complement C2 Antibodies (a). Generation of Recombinant Human Complement C2

Recombinant human complement protein C2 with a N-terminal his-tag was generated by U-Protein Express, Utrecht, The Netherlands. Briefly, cDNA encoding for human complement protein C2 (GenBank Sequence: NM_000063; see SEQ ID NO. 1) was cloned, and subsequently expressed in HEK293 cells. C2 was purified by affinity chromatography, and analyzed with SDS-PAGE using the pre-cast gel NuPage® Novex® system (Invitrogen). Proteins were stained with Coomassie brilliant blue.

As shown in FIG. 1 (lane 1), the C2 preparation showed >95% purity, i.e., one band was observed with a molecular mass of z 100 kDa, consistent with the predicted mass of glycosylated human C2.

(b). Biochemical Characterization of Recombinant Human Complement C2

Recombinant C2a and C2b were generated by incubation of C2 (100 μL of a 400 μg/mL solution) with plasma-derived activated C1s (100 μL of a 16 μg/mL solution; Calbiochem) for 1 hour at 37° C. in PBS (C1s-to-C2 ratio of 1:25). To determine the presence of N-linked glycans on C2, 1.8 μg uncleaved or C1s-cleaved recombinant C2 was treated with Peptide-N-Glycosidase F (PNGase F; New England Biolabs) for 1 hour at 37° C. in reaction buffer according to manufacturer's instructions (New England Biolabs). Proteins were analyzed by SDS-PAGE using the pre-cast gel NuPage® Novex® system (Invitrogen), and stained with Coomassie brilliant blue.

As shown in FIG. 1 (lane 1 vs lane 3), C1s cleaved recombinant C2 into subcomponents C2a (≈70 kDa) and C2b (≈30 kDa), consistent with the predicted mass of C2a and C2b, respectively. Wild-type recombinant C2, and both C1s-cleaved recombinant C2a and C2b, carried N-linked glycans, which was evident from the lower apparent molecular masses after incubation with PNGase F (see lane 1 vs lane 2, and lane 3 vs lane 4 in FIG. 1). These results agree with the notion that human C2a and C2b have 6 and 2 putative N-linked glycosylation sites, respectively, (Martini et al., BMC Immunol 2010, 11: 43; Krishnan et al., J Mol Biol 2007, 367: 224; Krishnan et al., Acta Cristallogr D Biol Crystallogr 2009, D65: 266).

(c). Immunization and Generation of Antibodies Against Glycosylated Human Complement C2

According to prior art, inhibitory antibodies against glycosylated human C2 can only obtained by immunization of mice with deglycosylated purified human C2 (Oglesby et al., J Immunol 1988, 2: 926) or with purified human subcomponent C2a (US 2001/0026928 A1), and not with intact glycosylated purified human C2.

In contrast to Oglesby's immunization approach (see above; J Immunol 1988, 2: 926), BALB/c mice (females, 6-8 weeks of age; Charles River Laboratories) were subcutaneously injected with ≈500 μL glycosylated recombinant human complement C2 in Complete Freund's adjuvant (each mouse with 25 μg glycosylated recombinant human complement C2 in 250 μL PBS-5 mM benzamidin HCl (U-Protein Express) mixed with 250 μL Complete Freund's adjuvant (Sigma)) on Day 0. Antibody responses in mice were then boosted by subcutaneous injections of glycosylated recombinant C2 in Incomplete Freund's adjuvant (each mouse with 25 μg glycosylated recombinant human complement C2 in 250 μL PBS-5 mM benzamidin HCl mixed with 250 μL Incomplete Freund's adjuvant (Sigma)) on Day 21 and Day 42, and intraperitoneal injections with glycosylated recombinant C2 without adjuvant (each mouse with 25 µg recombinant C2 in 250 µL PBS-5 mM benzamidin HCL) on Day 63 and on Day 64. On day 67, splenocytes from immunized mice were fused with SP2/0-Ag14 myeloma cells (DSMZ) using standard hybridoma technology originally described by Köhler and Milstein (Nature 1975, 256: 495). Briefly, immunized mice were sacrificed. Splenocytes were teased from spleens, and washed in serum-free opti-MEM® I with GlutaMax medium (SF medium; Invitrogen). Logarithmically growing SP2/0-Ag14 myeloma cells were washed in SF medium, and added to the splenocytes yielding a 5:1 ratio of splenocytes-to-myeloma cells. The cells were then pelleted, and the supernatant was removed. One ml of a 37% (v/v) solution of polyethylene glycol 4000 (Merck) was then added dropwise over a 60 sec period, after which the cells were incubated for another 60 sec at 37° C. Eight ml SF medium, followed by 5 ml opti-MEM® I with GlutaMax/10% (v/v) fetal calf serum (FCS; Bodinco), was then slowly added with gentle agitation. After 30 minutes at RT, the cells were pelleted, washed in opti-MEM® I with GlutaMax/10% FCS to remove residual polyethylene glycol, and finally plated at a concentration of $10^5$ cells/200 µl per well in aminopterin selection medium, i.e., opti-MEM® I with GlutaMax/10% FCS that was supplemented with 50× Hybri-Max™ aminopterin (a de novo DNA synthesis inhibitor (Sigma)). From Day 7, aminopterin selection medium was replenished every 2-3 days, and on Day 13, aminopterin selection medium was replaced by opti-MEM I with GlutaMax/10% FCS.

From Day 13 after fusion, supernatants from hybridomas were screened for anti-C2 antibody production using an ELISA with glycosylated recombinant human C2 (U-Protein Express) coated on 96-wells plates. The screening ELISA was performed as follows. Glycosylated human recombinant C2 was used for coating (250 ng/ml in PBS; 25 ng/100 µl/well). After extensive washing with PBS/0.05%, w/v, Tween 20, plates were blocked with PBS/0.05% Tween 20/1%, w/v, bovine serum albumin (BSA) (Roche) for 1 hour at room temperature (RT). Subsequently, plates were incubated with 100 µl undiluted hybridoma supernatant/well for 1 hour at RT. After extensive washing in PBS/0.05% Tween 20, binding of antibodies was determined with 1:5000 diluted horseradish peroxidase-conjugated goat anti-mouse Fcγ-specific antibodies (Jackson ImmunoResearch) for 1 hour at RT, followed by a ready-to-use solution of TMB substrate (Invitrogen) for colorimetric detection. After adding 1 M $H_2SO_4$, optical densities were measured at a wavelength of 450 nm (reference wavelength of 655 nm) using a microplate reader (BioRad). Hybridomas positive in this ELISA were expanded and cryopreserved.

Several fusion experiments yielded 36 hybridomas that produced antibodies against glycosylated human C2 as measured with the screening ELISA just described. Supernatants of these hybridomas were tested for inhibitory activity towards glycosylated C2 as is described in the next examples.

Figure 2:
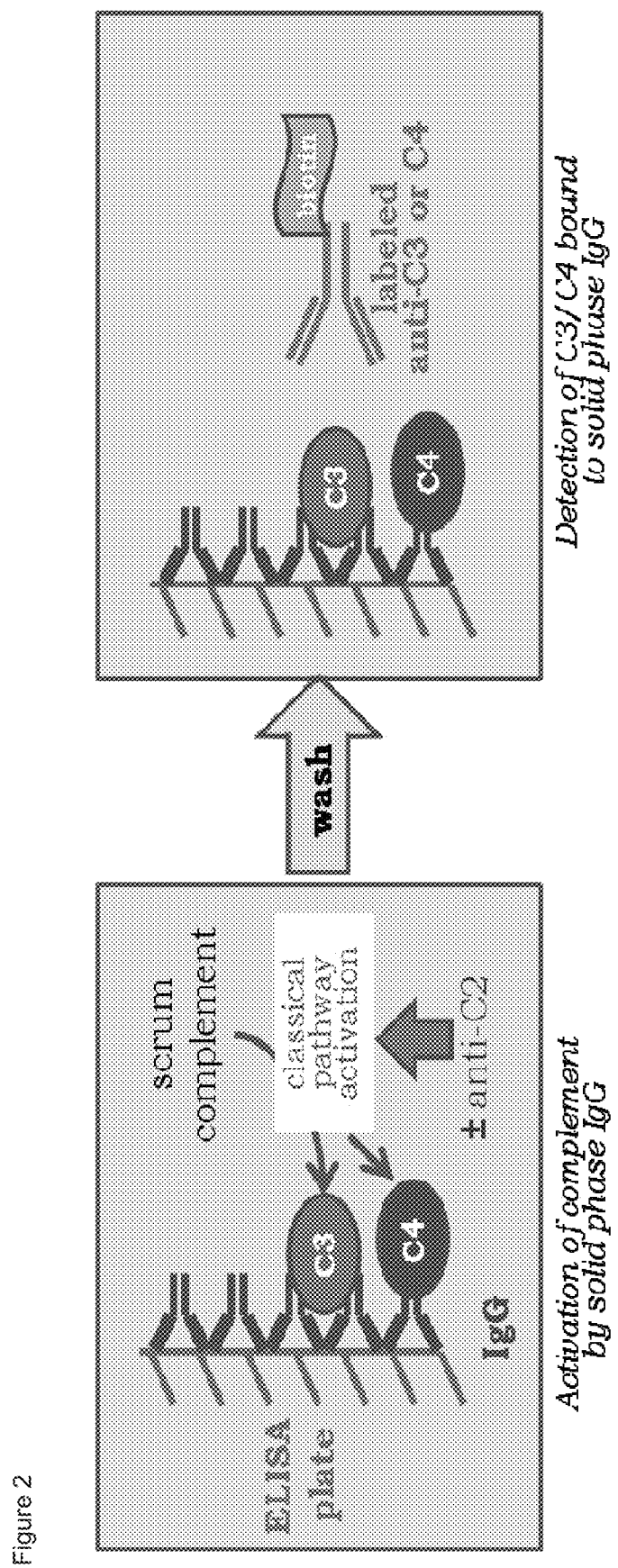

Example 2: ELISA to Screen Inhibitory Activity of Anti-C2 Hybridoma Supernatants Culture supernatants of the anti-C2 antibodies producing hybridoma were initially screened for inhibitory effects on C2 in an ELISA system (FIG. 2). In this ELISA aggregated human IgG was coated onto microtitre plates (Greiner-Bio-One), and then incubated with diluted fresh serum either or not pre-incubated with anti-C2 containing hybridoma supernatant. Fixation of C4 and C3 onto the plate, indicative for complement activation, was then measured with biotinylated polyclonal affinity purified anti-C3 and anti-C4 antibodies. Anti-C3 and anti-C4 binding to the plate was then measured with streptavidin-HRP, which in its turn was visualized with 3',5'-tetratmethylbenzidine. Briefly, ELISA plates (Greiner-Bio-One) were coated overnight at room temperature with 100 µl per well of 10 µg/ml aggregated IgG in PBS. Final volume of this and all subsequent steps in the ELISA was 100 µl. Prior to use the plates were washed 5 times with MilliQ. The samples to be tested were prepared as follows. Fresh human serum was diluted 1 to 100 in veronal buffered saline, pH 7.4 (Lonza), containing 1 mM $MgCl_2$, 0.15 mM $CaCl_2$ and 0.1% (w/v) Tween 20 (VB-T). One volume of diluted serum was incubated with 1 volume of hybridoma supernatant and one volume of VB-T for 30 min at room temperature. Negative control sample was prepared by mixing 100 µl of diluted fresh normal serum with 100 µl EDTA (0.1 M) and 100 ul of VB-T. As a positive control, the mixture was prepared with diluted serum and VB-T instead of culture supernatant. Hundred µl of these mixtures were then incubated in the aggregated IgG-coated plates for 30 minutes at 37° C. The plates were washed and incubated with biotinylated antibodies against human C4 and C3 diluted 1 to 50 in PBST. Bound anti-C4 or anti-C3 murine antibodies were detected by incubation with 100 streptavidin-HRP (BioLegend) 1:7500 diluted in PBS-T for 1 hour at room temperature. Finally, the plates were washed 5 times with distilled water and developed with 3,5,3',5'-tetramethyl benzidine (TMB substrate, Invitrogen). The reaction was stopped by addition of 100 µl of 2 M $H_2SO_4$ to each well. The absorbance of each well was then read at 450 nm on a Multiskan EX plate reader (Thermo Scientific). Data were analyzed using Graphpad Prism 5.

Figure 3B:
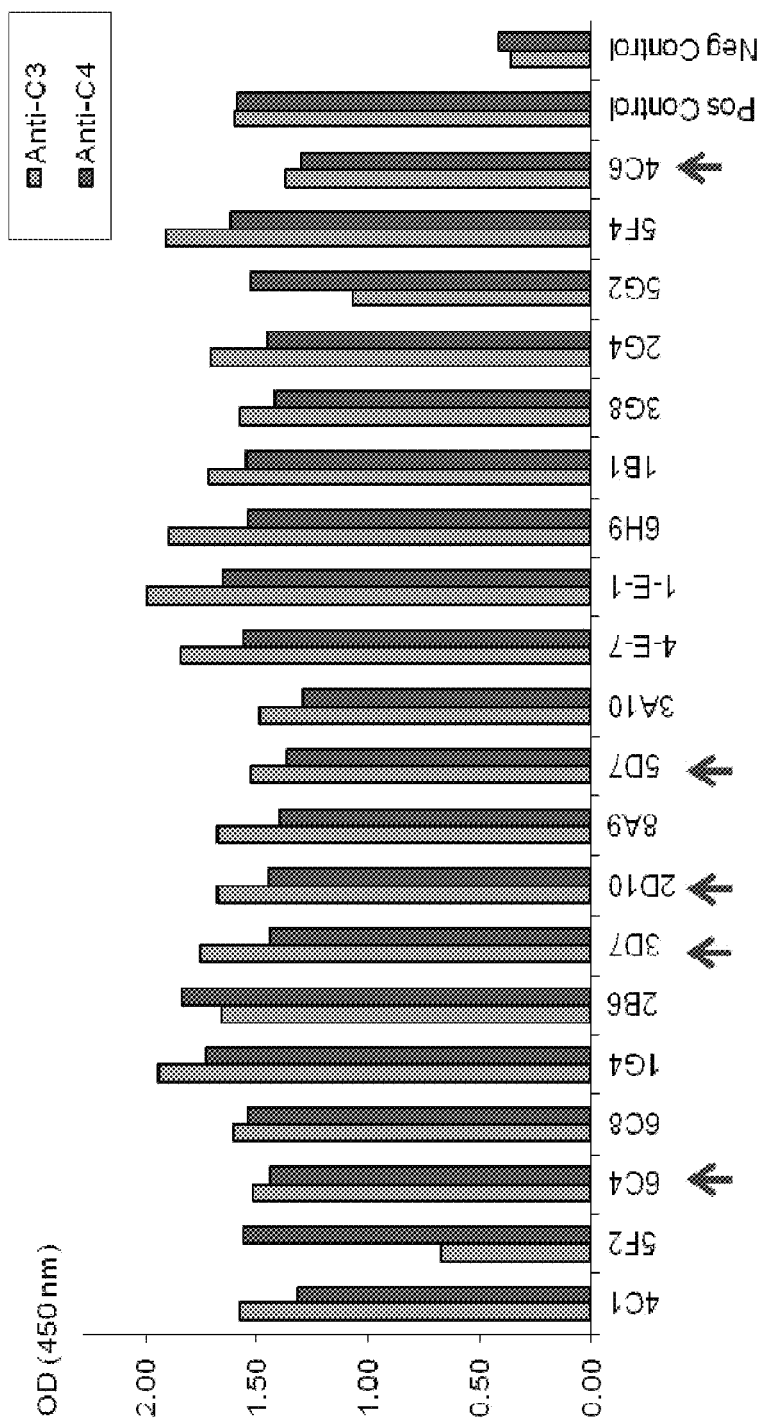

Nine hybridomas from several fusion experiments showed substantial inhibitory activity of C3 binding whereas they did not affect C4 fixation (FIGS. 3A and B), ruling out that their effect on C3 activation was due to aspecific activation and consumption of complement during processing of the samples. The numbers of these hybridomas are: anti-C2-7, anti-C2-13, anti-C2-23, anti-C2-24, anti-C2-26, anti-C2-27, anti-C2-32, anti-C2-5F2 and anti-C2-5G2. In addition a few borderline inhibiting hybridomas were identified (hybridoma 19, 35, 60 and 65). Sequencing of the heavy and light chain variable regions revealed that mAbs anti-C2-24 and anti-C2-32 were identical, as were mAbs anti-C2-5F4 and anti-C2-5G2.

Example 3: Binding Characterization of Purified Murine Anti-C2 Antibodies 13, 32, 35, 60 and 5F2.4

(a). Binding of mAbs Anti-C2-13, -32, -35, -60 and -5F2.4 to Glycosylated Recombinant Human C2

Inhibitory and non-inhibitory anti-C2 mAbs were purified with protein G affinity chromatography (GE Healthcare). Heavy and light chains were typed for isotype class using the IsoQuick™ Kit for Mouse Monoclonal Isotyping (Sigma) (Table 1).

TABLE 1

Antibody class of some murine mAbs against human C2

| Murine mAb | Inhibiting in screening assay (y/n) | Murine antibody class |
|---|---|---|
| Anti-C2-7 | Y | IgG1κ |
| Anti-C2-13 | Y | IgG1κ |
| Anti-C2-18 | N | IgG1κ |
| Anti-C2-19 | N | IgG1κ |

TABLE 1-continued

Antibody class of some murine mAbs against human C2

| Murine mAb | Inhibiting in screening assay (y/n) | Murine antibody class |
|---|---|---|
| Anti-C2-23 | Y | IgG1κ |
| Anti-C2-24 | Y | IgG1κ |
| Anti-C2-26 | Y | IgG1κ |
| Anti-C2-27 | Y | IgG1κ |
| Anti-C2-31 | N | IgG1/M/κ/λ |
| Anti-C2-32 | Y | IgG1κ |
| Anti-C2-35 | Y/N | IgG1κ/IgG2bκ (2b weak signal) |
| Anti-C2-60 | Y/N | IgG1κ |
| Anti-C2-63 | N | IgG1κ |
| Anti-C2-79 | N | IgG1κ/IgG2bκ (2b weak signal) |
| Anti-C2-5F2.4 | Y | IgG2aκ |

Purified mAbs anti-C2-5F2.4, anti-C2-13, anti-C2-32, anti-C2-35 and anti-C2-60 were further characterized by assessing binding to high (200 ng per well) and low (25 ng per well) amounts of glycosylated recombinant C2 (U-protein Express) using the procedure described above in Example 1 (c).

Figure 4:
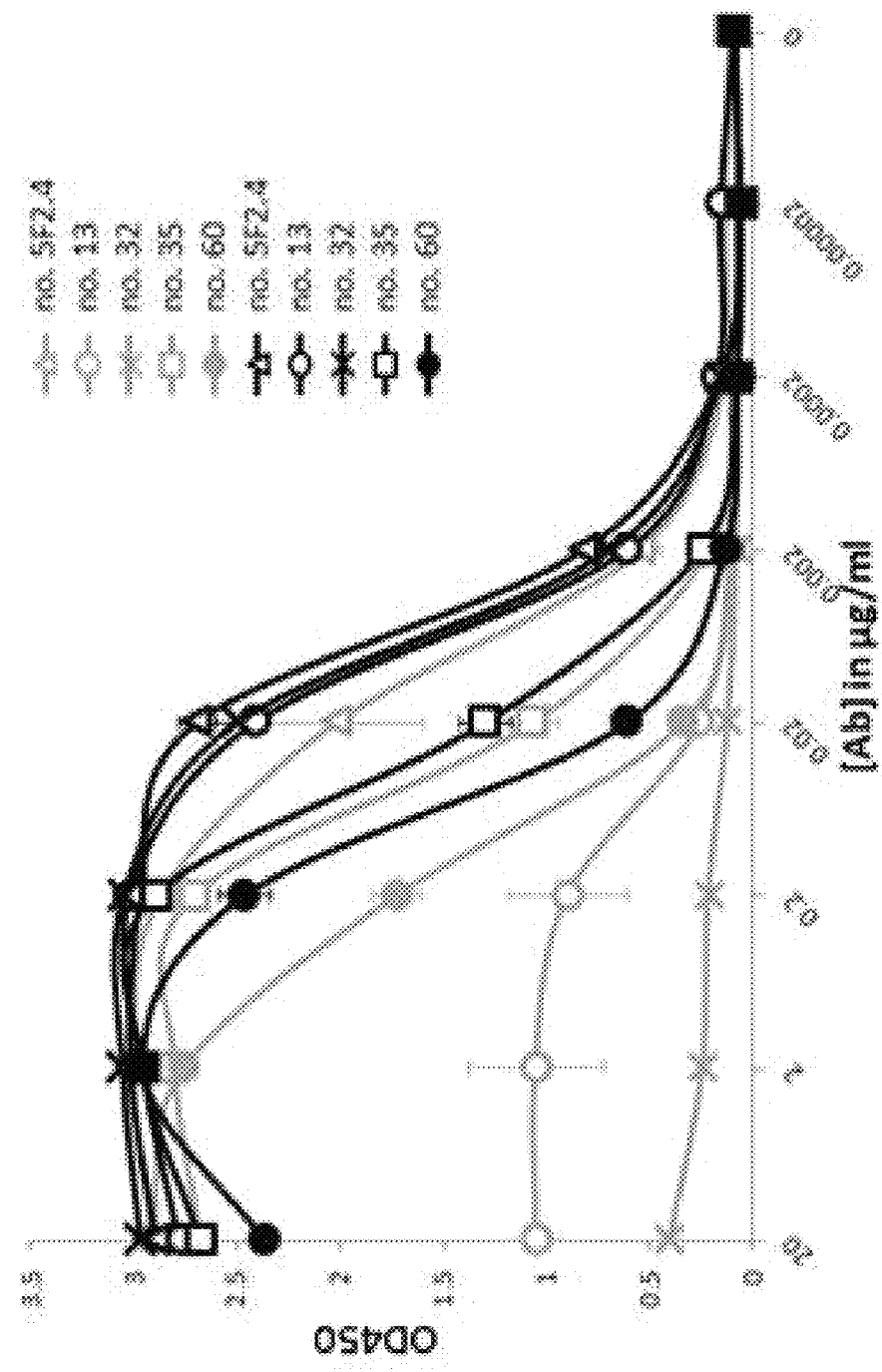

As shown in FIG. 4, antibodies anti-C2-5F2.4, anti-C2-13, anti-C2-32, anti-C2-35 and anti-C2-60 dose-dependently bound to glycosylated recombinant human complement C2. Binding of antibodies anti-C2-5F2.4, anti-C2-35 and anti-C2-60 showed only slight differences regarding binding to C2 coated at 25 ng/well and at 200 ng/well, whereas binding of the antibodies anti-C2-13 and anti-C2-32 was significantly decreased to C2 coated at 25 ng/well in comparison to C2 coated at 200 ng/well (FIG. 4). Hence, (relative) affinity of mouse anti-human complement C2-13 (mIgG1κ) and anti-C2-32 (mIgG1κ) was lower than that of the antibodies anti-C2-5F2.4 (mIgG2aκ), anti-C2-35 (mIgG1κ) and anti-C2-60 (mIgG1κ).

(b). Binding of mAbs Anti-C2-13, -32, -35, -60 and -5F2.4 to C1s-Cleaved Glycosylated Recombinant Human C2

Binding of purified mAbs anti-C2-5F2.4, anti-C2-13, anti-C2-32, anti-C2-35 and anti-C2-60 to glycosylated recombinant C2 (200 ng per well; U-protein Express) or to C1s-cleaved glycosylated recombinant C2 (200 ng per well), was assessed using the procedure described above in Example 1(c).

Antibodies anti-C2-5F2.4, anti-C2-13, anti-C2-32, anti-C2-35 and anti-C2-60 dose-dependently bound to glycosylated recombinant C2 (FIG. 5A) and to C1s-cleaved glycosylated recombinant C2 (FIG. 5B). The latter observation demonstrated that antibodies anti-C2-5F2.4, anti-C2-13, anti-C2-32, anti-C2-35 and anti-C2-60 did not recognize an epitope on the C1s cleavage site (i.e., $Arg^{243}$–|–$Lys^{244}$ bond; http://www.uniprot.org/uniprot/P09871) of glycosylated recombinant human complement C2.

Example 4: Inhibitory Activity of Purified Murine Anti-C2 mAbs on Fixation of C3 to Solid-Phase Aggregated IgG To confirm the inhibitory activity of the anti-C2 mAbs the same assay as described in Example 2 was used except that the samples to be tested were prepared differently to enhance robustness of the assay. Samples were prepared by mixing 10 μl of normal fresh serum with 10 μl of the purified anti-C2 mAb in PBS. Positive control sample was prepared by mixing 10 μl normal fresh serum with 10 μl VB. As a negative control sample 10 μl normal fresh serum was mixed with 10 μl EDTA (0.1 M). All samples were incubated for 30 minutes at room temperature. Next, all samples were diluted 1 to 100 in PBS/0.1% Tween 20 and then the same protocol was performed according to the protocol described in the previous example. AS shown in FIG. 6, neither a control mAb nor the non-inhibiting mAb anti-C2-63 affected the fixation of C3 to the solid-phase IgG. In contrast The anti-C2 antibodies 32, 5F2.4 and 13 inhibited fixation of C3 to the plates, whereas anti-C2 mAbs 35 and 60 displayed no significant activity in this assay.

Example 5: Inhibitory Activity of Purified Murine Anti-C2 mAbs on the Activation of C3 in Fresh Serum by Fluid-Phase Aggregated IgG The effect of the anti-C2 mAbs-13, 32, 35, 60 and 5F2 on fluid phase C3 activation was measured in an assay in which fresh human serum pre-incubated with anti-C2 mAb, was incubated with aggregated IgG. Activation of C3 was then measured in the samples with an ELISA previously described (Wolbink G J et al., J Immunol Methods 1993, 63: 67). The samples were prepared by mixing 30 μl normal fresh serum with 30 μl VB containing the anti-C2 mAb and incubated for 20 minutes at RT. Next, 30 μl of aggregated IgG (1 mg/ml) in VB was added to all samples to activate complement except to the negative controls, which were supplemented with 30 μl VB. Samples were subsequently incubated for 30 minutes at 37° C. Complement activation was then stopped by adding 60 μl EDTA (0.1 M) to all samples. After 15 minutes at RT, all samples were diluted with PBS/0.1% Tween 20 supplemented with 10 mM EDTA (final dilution of serum was 1 to 4000), and tested in the ELISA for activated C3. As a positive control fresh human serum was pre-incubated with 30 μl VB containing no mAb. As a negative control, fresh serum was incubated with VB only, and not with mAb or aggregated IgG. This control was made twice, one of which was kept on melting ice during all incubations. Results were expressed as Arbitrary Units of activated C3, which were calculated by comparison with a standard curve consisting of serial dilutions of normal serum aged. As the assay for activated C3 does not discriminate between C3b, C3bi or C3c, activated C3 was denoted as C3b/c. FIG. 7 shows that upon addition of aggregated IgG to human serum C3b/c was generated (positive control in FIG. 7). Addition of IgG (Gamma-Quin IgG in the figure), an irrelevant control mAb ((anti-FXI) in FIG. 6) or the non-inhibiting anti-C2 mAb-63 had no effect on the generation of C3b/c in serum by aggregated IgG. In contrast, anti-C2 mAbs 7, 13, 32, 35, 60 and 5F2.4 all inhibited the generation of C3b/c by aggregated IgG (FIG. 7).

Example 6: Effects of Purified Murine Anti-C2 mAbs on Cytotoxicity of Anti-HLA Antibodies As an ex vivo model for antibody-mediated rejection of human transplants, the diagnostic cross match test which tests for the presence of complement-dependent antibodies in candidate transplant recipients, was modified. In the normal test donor cells or cells with the same HLA molecules as the donor are mixed with heat inactivated serum of the recipient in the presence of rabbit complement. In case the recipient has antibodies against the HLA molecules of the donor, cells will be lysed. This is assessed by microscope and expressed as a cytotoxicity score (from 1—no lysis—to 8—>80% lysis). To test the effects of the anti-C2 mAbs this assay was modified by substituting the rabbit serum for fresh human serum. Moreover, serum of a patient with high titers of anti-HLA antibodies against multiple HLA molecules was used.

The modified cross match test was performed as follows. Wells of a Terasaki tray (Greiner) were filled with 1 µl highly immunized serum with HLA-antibodies and 1 µl PBMC suspension (2-5×10$^6$ cells/ml) and incubated for 1 hour at RT. Meanwhile samples to be tested were prepared by mixing 5 µl fresh normal serum, 15 µl VB and 5 µl VB containing anti-C2 mAb. A positive control sample was made by adding 5 µl normal fresh serum to 20 ul veronal buffer without anti-C2 mAb, and a negative control sample was made by mixing 5 µl normal fresh serum, 15 µl veronal buffer and 5 µl 100 mM EDTA. Subsequently, all samples were incubated for 20 minutes at RT. Next, 10 µl of each sample were added to the wells in duplicate and incubated for two hours at RT. Finally, five µl of Fluoroquench (Sanbio) was added to the wells. After 30 minutes the Terasaki tray was read by using automated microscope (Leica) and in some experiments cell lysis was calculated with a special program called "Leica Q WIN", whereas in other experiments lysis was scored by an experienced technician. A cytotoxicity score of "0" means no lysis of the cells, whereas a score of 8 was given when >80% of the cells were lysed.

The anti-C2 antibodies were tested at concentration ranging from 0.6 to 1.5 mg per ml. Anti-C2 mAbs 18, 19, 23, 31 and 63 had no effect on complement dependent killing of the cells sensitized with anti-HLA antibodies (see FIG. 8). In contrast the mAbs anti-C2 13, 32, 35, 60, 7, 24, 79 all inhibited complement-dependent cytotoxicity in this model for antibody-mediated allograft rejection.

Example 7: Characterization of Domains on Human Complement C2 Recognized by Mouse Anti-Human Complement C2 Antibodies 13, 32, 35, 60 and 5F2.4

(a). Mapping of Epitopes for mAbs Anti-C2-13, -32, -35, -60 and -5F2.4 on Glycosylated Recombinant Human Subcomponents C2a and C2b with Western Blotting Glycosylated recombinant human C2 (range 125-500 ng/lane, see FIG. 9; U-protein Express) or C1s-cleaved glycosylated recombinant human C2 (range 62.5-1000 ng/lane, see FIG. 9; for C2 cleavage procedure, see Example 1(b)) were electrophorized using 4-12% Tris-Bis gels and MOPS running buffer (Invitrogen) under non-reducing conditions in pre-cast SDS-PAGE (NuPage® Novex® system). Then, the C2 proteins were electro-blotted onto a polyvinylidene fluoride (PDVF) transfer membrane (Millipore). After blocking with PBS/0.05% Tween 20/1% BSA fraction V (Roche) for 20 min at RT, PDVF membranes were incubated with anti-C2 mAbs anti-C2-C2-5F2.4 (100 ng/mL), anti-C2-13 (200 ng/mL), anti-C2-32 (200 ng/mL), anti-C2-35 (100 ng/mL) and anti-C2-60 (200 ng/mL) for 1 hour at RT. After extensive washing in PBS/0.05% Tween 20, binding of anti-C2 mAbs was determined with 1:10,000 diluted horseradish peroxidase-conjugated goat anti-mouse Fcγ-specific antibodies (Jackson ImmunoResearch) for 1 hour at RT, followed by a ready-to-use solution of TMB substrate (Sigma) for colorimetric detection.

As shown in FIG. 9, all examined anti-C2 mAbs bound to non-cleaved glycosylated recombinant human C2 (≈100 kDa). In addition, mAb anti-C2-5F2.4 and anti-C2-35 specifically recognized glycosylated subcomponent C2b (z 30 kDa), whereas mAbs anti-C2-13 and anti-C2-32 specifically recognized glycosylated subcomponent C2a (≈70 kDa). MAb anti-C2-60 seemed to bind to both glycosylated subcomponents C2a and C2b.

(b). Binding of mAbs Anti-C2-13, -32, -35, -60 and -5F2.4 to Glycosylated Recombinant Human Subcomponent C2a with ELISA Glycosylated recombinant human C2a was purified from C1s-cleaved C2 (for C2 cleavage procedure, see Example 1(b)) by size-exclusion chromatography (Yarra™ 3U sec 2000 300×4.60 column). On SDS-PAGE using the pre-cast gel NuPage® Novex® system (Invitrogen) the C2a preparation was >95% homogeneous (not shown). Subsequently, purified anti-C2 mAbs were further analyzed for the binding to purified C2a (200 ng per well) using the ELISA procedure described above in Example 1(c).

As shown in FIG. 10A, and consistent with the Western blotting data (see Example 7(a)), mAbs anti-C2-13 and anti-C2-32 demonstrated a dose-dependent binding (i.e., saturation at 0.1 µg/mL) to purified glycosylated recombinant C2a, whereas mAbs anti-C2-60 showed intermediate binding to C2a, and mAbs anti-C2-5F2.4 and anti-C2-35 hardly bound to C2a. A trace amount of non-cleaved glycosylated recombinant C2 explained the observed binding of mAbs anti-C2-5F2.4 and anti-C2-35.

(c). Binding of mAb Anti-C2-5F2.4 to Deglycosylated, Denatured and Reduced Recombinant Human C2 with ELISA Deglycosylation of recombinant C2 was performed using the procedure described above in Example 1(b) but the reaction buffer was without denaturation/reduction reagents, and treatment with Peptide-N-Glycosidase F (PNGase F; New England Biolabs) was overnight at 37° C. Denaturation and reduction of recombinant C2 were performed using NuPAGE® LDS Sample Buffer 4× (Invitogen) with or without NuPAGE® Reducing Agent 10× (Invitrogen), respectively. Subsequently, purified mAb anti-C2-5F2.4 was further analyzed for the binding to untreated recombinant C2 (200 ng per well), deglycosylated recombinant C2 (100 ng per well), denatured recombinant C2 (200 ng per well), and reduced recombinant C2 (200 ng per well) using the ELISA procedure described above in Example 1(c).

As shown in FIG. 10B, mAb anti-C2-5F2.4 demonstrated a dose-dependent binding to deglycosylated (non-denatured/non-reduced) recombinant C2. As shown in FIG. 10C, mAb anti-C2-5F2.4 demonstrated a dose-dependent binding to denatured recombinant C2, and showed no binding to reduced (denatured) recombinant C2.

In summary (see FIG. 20), mAb anti-C2-5F2.4 seemed to recognize an epitope on the subcomponent C2b of human C2 and not an epitope on subcomponent C2a of human C2 (see Examples 7(a) and 7(b)). The binding of mAb anti-C2-5F2.4 on subcomponent C2b seemed to be insensitive to C1s cleavage (see Example 3(b)), deglycosylation and denaturation of human C2. However, internal cysteine bridges seemed to be critical for the binding of mAb anti-C2-5F2.4 on subcomponent C2b.

Example 8: Anti-C2 mAbs 13, 32, 35, 60 and 5F2 Inhibit the Cleavage of C2 in Fresh Human Serum by Fluid-Phase Aggregated IgG To investigate the mechanism of inhibition of the anti-C2 mAbs, 10 µl of serum was incubated with 10 µl of anti-C2 mAb at 0.48 mg/ml at room temperature. Then 10 µl of aggregated IgG at 1 mg/ml was added and samples were incubated for 30 min at 37° C. 35 µl water and 35 µl sample buffer were added to the samples, which subsequently were boiled for 10 minutes. Finally, 15 μl of the mixture was then separated on 7.5% SDS-PAGE. Samples were blotted and incubated with 5 μg biotinylated anti-C2-5F2.4. As shown in the previous example, this antibody binds to native C2 and to C2b, which has a Mr≈30.000. Hence, in case of non-inhibiting antibody added to serum prior to activation with aggregated IgG the majority of C2 is expected to be present in the serum sample as C2b (and C2a which is not visualized on the blot) and a minority as intact C2 with Mr≈90.000. Indeed this was observed with control human IgG (FIG. 11, the lane labelled with IgG), with a control mAb not directed to C2 (lane labelled C in FIG. 11), and with a non-inhibiting C2 mAb (lane labelled with 63 in FIG. 11), though this mAb showed somewhat less cleavage of C2 as compared to that observed with the control mAbs not directed to C2, probably due to some steric hindrance. All the other mAbs decreased the cleavage of C2 in serum upon activation of the complement system with aggregated IgG (FIG. 11).

Example 9: MAbs Anti-C2-13, -32, -35, -60 and -5F2.4 do not Inhibit the Cleavage of Free Fluid-Phase Glycosylated Recombinant Human C2 by Human C1s To investigate the mechanism of inhibition of the anti-C2 mAbs, glycosylated recombinant human C2 was pre-incubated with mAbs anti-C2-5F2.4, anti-C2-13, anti-C2-32, anti-C2-35 and anti-C2-60 (at a molar C2-to-antibody ratio of 1:2) for 30 min at RT. In parallel, isotype controls of mouse IgG1κ and IgG2aκ (both from BD Biosciences) were tested as negative controls. Then, human C1s (C1s-to-C2 ratio of 1:25; Calbiochem) was added for 1 hour at 37° C. The mixtures were analyzed by SDS-PAGE using the precast gel NuPage® Novex® system (Invitrogen), and stained with Coomassie brilliant blue.

As shown in FIG. 12, none of the anti-C2 mAbs inhibited the cleavage of recombinant C2 by C1s. Moreover, no effect on the cleavage of C2 by C1s was observed (data not shown) when higher concentrations (at molar C2-to-antibody ratios from ≈1:3 to ≈1:7) of anti-C2 mAbs were used. Collectively, these results demonstrated that mAbs anti-C2-5F2.4, anti-C2-13, anti-C2-32, anti-C2-35 and anti-C2-60 did not recognize an epitope on or near the C1s cleavage site (i.e., $Arg^{243}$–|–$Lys^{244}$ bond; http://www.uniprot.org/uniprot/P09871).

Example 10: Molecular Genetic Characterization of Mouse Anti-C2-5F2.4, -13, -32, -35 and -60 with Degenerated Primers Hybridoma cells were washed with PBS, and aliquoted in microvials containing $5×10^6$ cells, and stored as pellets at −80° C. These cell pellets were used to isolate RNA by using RNeasy Mini Isolation Kit (QIAGEN). RNA concentration was determined (A260 nm), and RNA was stored at −80° C. By reverse transcriptase, cDNA was synthesized from 2 μg of RNA using the RevertAid™ H Minus First Strand cDNA Synthesis Kit (Fermentas), and stored at −20° C. Based on the isotype of the antibodies, primers as shown in Table 3 were designed to amplify the V-regions of mouse anti-human C2-5F2.4, -13, -32, -35 and -60.

TABLE 3

PCR primers used to clone cDNA of the anti-C2 mAbs

| region+ | primer no.* | primer sequence** | direction | gene |
|---|---|---|---|---|
| 5F2.4 VL | 317 | CTCTTGGTTCCAGGTTCCAC | s | kappa |
| | 4 | ACACTCATTCCTGTTGAAGCTCTTG | as | kappa cs |
| 5F2.4 VH | 1 | SAGGTSMARCTGVAGSAGTCWGG | s | IgG FR1 |
| | 204 | TGGACAGGGATCCAGAGTTC | as | IgG cs |
| 13 VL | 213 | GCGCTTAACACAAACCCNCCNYT | s | kappa FR1 |
| | 4 | ACACTCATTCCTGTTGAAGCTCTTG | as | kappa cs |
| 13 VH | 1 | SAGGTSMARCTGVAGSAGTCWGG | s | IgG FR1 |
| | 2 | AATTTTCTTGTCCACYTTGGTGCT | as | IgG cs |
| 32 VL | 265 | GCGATATACARATGACNCARAC | s | kappa FR1 |
| | 4 | ACACTCATTCCTGTTGAAGCTCTTG | as | kappa cs |
| 32 VH | 1 | SAGGTSMARCTGVAGSAGTCWGG | s | IgG FR1 |
| | 2 | AATTTTCTTGTCCACYTTGGTGCT | as | IgG cs |
| 35 VL | 201 | GACAGTTGGTGCAGCATCAG | as | kappa cs |
| | 201 | GACAGTTGGTGCAGCATCAG | as | kappa cs |
| 35 VH | 1 | SAGGTSMARCTGVAGSAGTCWGG | s | IgG FR1 |
| | 2 | AATTTTCTTGTCCACYTTGGTGCT | as | IgG cs |
| 60 VL | 201 | GACAGTTGGTGCAGCATCAG | as | kappa cs |
| | 201 | GACAGTTGGTGCAGCATCAG | as | kappa cs |
| 60 VH | 1 | SAGGTSMARCTGVAGSAGTCWGG | s | IgG FR1 |
| | 2 | AATTTTCTTGTCCACYTTGGTGCT | as | IgG cs | s = sense; as = antisense, cs = constant region
+VL = variable light chain region, VH = variable heavy chain region; *no. according to Bioceros internal coding system; **degenerated primers: M = C or A; V = G, A, or C; N = A, C, G, or T; Y = C or T; R = A or G; W = A or T; and S = G or C.

Primer 1 is a sense primer designed to anneal with framework 1 (FR1) of mouse VH region; primers 2 and 204 are antisense primers annealing with the constant region of mouse heavy chains. Primers 213 and 265 are both sense primers annealing with FR1 of mouse VL regions (κ); primers 4 and 201 are both antisense primers designed to anneal with the constant mouse κ light chain. Finally, primer 317 was designed to recognize a part of a mouse signal peptide sequence upstream of the FR1 region.

Various different PCRs were done using primer combinations shown in Table 3. V-regions of mouse anti-C2-5F2.4, -13, -32, -35 and -60 were amplified. Remarkably, variable light chain regions of mouse anti-C2-35 and -60 were amplified using antisense primer 201 only.

Accuprime™ Pfx DNA Polymerase (Invitrogen) was used to amplify the variable regions of heavy and light chains of mouse anti-C2-5F2.4, -13, -32, -35 and -60. The PCR products were analyzed on a 1% agarose gel. Products of PCR reactions were gel-purified and cloned in the pCR-Blunt II-TOPO® vector for sequence analysis. From plasmids containing a PCR insert, cloned inserts were analysed by DNA sequencing (performed by ServicXS B.V., Leiden, The Netherlands and Macrogen, Amsterdam, The Netherlands) to obtain the consensus sequence for V-regions of the anti-C2 mAbs. At least 3 informative sequences of VH and of VL were obtained for all examined mAbs. It should be noted that due to the nature of the sense primers used, the first 6-8 N-terminal amino acids are dictated by the used degenerated primers for almost all determined amino acid consensus sequences. Theoretically, original mouse sequences can differ in these regions. The amino acid consensus sequences of VH- and VL-regions of mouse anti-C2-5F2.4, -13, -32, -35 and -60 were determined, i.e., SEQ ID NO. 2 and NO. 3, SEQ ID NO. 10 and NO. 11, SEQ ID NO. 18 and NO. 19, SEQ ID NO. 26 and NO. 27, SEQ ID NO. 34 and NO. 35, respectively.

The listing or discussion of an apparently prior-published document in this specification should not necessarily be taken as an acknowledgement that the document is part of the state of the art or is common general knowledge.

Example 11: Generation of Chimeric Human IgG1κ and/or Human IgG4κ (i.e., Swapping Constant Mouse IgGκ Domains for Constant Human IgGκ Domains) Anti-Human Complement C2-5F2.4, -13, -32, -35 and -60

Based on the murine V-regions sequences identified (see Example 10) chimeric human antibody versions of the mouse anti-C2-5F2.4, -13, -32, -35 and -60 mAbs were designed. To this end, CHO cell-optimized cDNA sequences SEQ ID NO. 47 (coding for chimeric human IgG1 heavy chain of mAb anti-human C2-32) and SEQ ID NO. 48 (coding for chimeric human κ light chain of anti-human C2-32) were purchased from GENEART (Regensburg, Germany), which encoded for a murine signal peptide followed by either the murine variable heavy chain linked to the human IgG1 constant region or followed by the murine variable light chain linked to the human kappa constant region, respectively.

In addition, a chimeric human (stabilized) IgG4 format of anti-C2-5F2.4, -13, -32, -35 and -60 was generated. For this, variable heavy and variable light chain regions were PCR-amplified with primers shown in Table 4. For sub-cloning purposes, appropriate restriction sites were incorporated in N- and C-terminal parts of cDNAs encoding V-regions. Kappa light chain of anti-human complement C2 antibody no. 32 was not amplified, because a construct was already available from the chimeric human κ construct used for the generation of chimeric human IgG1κ (see above). Native murine cDNAs were used as templates for all PCR reactions, except for the variable heavy chain of anti-human complement C2 antibody no. 32. For the latter, CHO-optimized cDNA of the chimeric human IgG1 construct was used (see above).

TABLE 4

PCR primers used to amplify variable heavy and variable light chain regions of the anti-C2 mAbs

| region+ | no.* | primer sequence** | |
|---|---|---|---|
| 5F2.4 VL | 356 | CCGCGGGAGTGCACAGCGACATTGTGCTGACACAGTCTCC | s |
| | 301 | CGGTCCGTTTTATTTCCAACTTG | as |
| 5F2.4 VH | 379 | GCCGCGGGAGTGCACAGCGAGGTGCAGCTGCAGCAGTCTGG | s |
| | 382 | CGCTAGCAGCAGAGACAGTGACCAGAGT | as |
| 13 VL | 336 | CCGCGGGAGTGCACAGCGATGTCCTCATGACACAAACGCCTCTCTCCCTG | s |
| | 286 | CGGTCCGTTTGATTTCCAGCTTG | as |
| 13 VH | 333 | CCGCGGGAGTGCACAGTCAGGTCCAACTGCAGCAGCCTGG | s |
| | 290 | GCTAGCTGAGGAGACGGTGACTG | as |
| 32 VH | 359 | CCGCGGGAGTGCACAGTCAGGTGCAGCTGCAGCAGTCTG | s |
| | 361 | GCTAGCAGAGGACACGGTCACGG | as |
| 35 VL | 342 | CCGCGGGAGTGCACAGCGACATTGTGATGTCACAGTCTCC | s |
| | 286 | CGGTCCGTTTGATTTCCAGCTTG | as |
| 35 VH | 339 | CCGCGGGAGTGCACAGTCAGGTCCAGCTGCAGCAGTCTGG | s |
| | 290 | GCTAGCTGAGGAGACGGTGACTG | as |
| 60 VL | 349 | CCGCGGGAGTGCACAGCGACATCCAGATGACTCAGTCTCC | s |
| | 301 | CGGTCCGTTTTATTTCCAACTTG | as |

TABLE 4-continued

PCR primers used to amplify variable heavy and variable light chain regions of the anti-C2 mAbs

| region⁺ | no.* | primer sequence** | |
|---|---|---|---|
| 60 VH | 345 | CCGCGGGAGTGCACAGCCAGGTGCAGCTGCAGCAGTCTGGCCCTGG | s |
| | 348 | GCTAGCTGAGGAGACGGTGACCGTGG | as | s = sense; as = antisense
⁺VL = variable light chain region, VH = variable heavy chain region; *no according to Bioceros internal coding system; **degenerated primers: M = C or A; V = G, A, or C; N = A, C, G, or T; Y = C or T; R = A or G; W = A or T; and S = G or C.

Accuprime™ Pfx DNA Polymerase (Invitrogen) was used to amplify the variable regions of heavy and light chains of anti-C2-5F2.4, -13, -35 and -60, and the variable heavy chain of anti-C2-32. PCR products were analyzed on a 1% agarose gel. Products of PCR reactions were gel-purified and cloned in the pCR-Blunt II-TOPO® vector for sequence analysis. From plasmids containing a PCR insert, cloned inserts were analysed by DNA sequencing (Macrogen, Amsterdam, The Netherlands) to obtain the correct V-regions containing the appropriate restriction sites. Subsequently, variable heavy chain regions were sub-cloned in expression plasmid v319 using SacII/NheI, which is a pcDNA3.1 derivative containing cDNA encoding a murine signal peptide followed by the stabilized human IgG4 heavy chain constant region. Variable light chain regions were sub-cloned in a similar expression plasmid v322 using SacII/RsrII, however, containing cDNA encoding a murine signal peptide in combination with the human κ light chain constant region.

For cDNA sequences of chimeric human IgG4κ anti-human complement C2 antibodies, see SEQ ID NO. 42 (coding for chimeric human IgG4 heavy chain of anti-C2-5F2.4), NO. 43 (coding for chimeric human κ light chain of anti-C2-5F2.4), NO. 44 (coding for chimeric human IgG4 heavy chain of anti-C2-13), NO. 45 (coding for chimeric human κ light chain of anti-C2-13), NO. 46 (coding for chimeric human IgG4 heavy chain of anti-C2-32), NO. 48 (coding for chimeric human κ light chain of anti-C2-32), NO. 49 (coding for chimeric human IgG4 heavy chain of anti-C2-35), NO. 50 (coding for chimeric human κ light chain of anti-C2-35), NO. 51 (coding for chimeric human IgG4 heavy chain of anti-C2-60), and NO. 52 (coding for chimeric human κ light chain of anti-C2-60).

For amino acid sequences of chimeric human IgG1 κ and chimeric human IgG4κ anti-human complement C2 antibodies, see SEQ ID NO. 53 (chimeric human IgG4 heavy chain of anti-C2-5F2.4), NO. 54 (chimeric human κ light chain of anti-C2-5F2.4), NO. 55 (chimeric human IgG4 heavy chain of anti-C2-13), NO. 56 (chimeric human κ light chain of anti-C2-13), NO. 57 (chimeric human IgG4 heavy chain of anti-C2-32), NO. 58 (chimeric human IgG1 heavy chain of anti-C2-32), NO. 59 (chimeric human κ light chain of anti-C2-32), NO. 60 (chimeric human IgG4 heavy chain of anti-C2-35), NO. 61 (chimeric human κ light chain of anti-C2-35), NO. 62 (chimeric human IgG4 heavy chain of anti-C2-60), and NO. 63 (chimeric human κ light chain of anti-C2-60).

Example 12: Binding Characterization of Chimeric Mouse-Human IgG1κ and/or IgG4κ Anti-Human Complement C2 Antibodies 5F2.4, 13, 32, 35 and 60

Chimeric mouse-human antibodies (human IgG1κ version for anti-C2-32, and human IgG4κ version for anti-C2-5F2.4, -13, -32, -35 and -60) were expressed using FreeStyle™ MAX CHO (CHO-S cells) Expression System (Invitrogen). Expressed chimeric mouse-human anti-human complement C2 antibodies were purified using affinity chromatography protein A columns (GE Healthcare). Using the same ELISA procedure as described in Example 3, all anti-C2 chimeric mAbs were tested for binding to high (200 ng per well) and low (25 ng per well) recombinant C2. Briefly, ELISA plates (Corning) were coated with the indicated amount of C2 in PBS overnight at 4° C. After extensive washing in PBS/0.05% Tween 20, plates were blocked with PBS/0.05% Tween 20/1% BSA fraction V (Roche) for 1 hour at RT. Subsequently, plates were incubated with 0, 0.00002-20.0 (10-fold dilution steps in block buffer) μg/mL protein A-purified chimeric mouse-human IgG1κ and/or IgG4κ anti-C2-5F2.4, -13, -32, -35 and -60 for 1 hour at RT. After extensive washing in PBS/0.05% Tween 20, binding of antibodies was determined with 1:5000 diluted horseradish peroxidase-conjugated goat anti-human IgG-specific (heavy and light chains) antibodies (Jackson ImmunoResearch) for 1 hour at RT, followed by a ready-to-use solution of TMB substrate (Invitrogen) for colorimetric detection. After adding 1 M $H_2SO_4$, optical densities were measured at a wavelength of 450 nm (reference wavelength of 655 nm) using a microplate reader (BioRad).

FIG. 13 (mean±SD, n=2) shows that the binding characteristics of the chimeric antibodies were exactly the same as those of the purified murine antibodies (FIG. 4). Chimeric anti-C2-13 and -32 did not bind well to C2 coated at low concentration, whereas the other chimeric antibodies bound well to both concentrations of C2. Hence, the (relative) affinity of chimeric mouse-human anti-C2-13 (chuIgG4κ) and -32 (both chuIgG4κ and chuIgG1κ) seemed to be lower than that of chimeric mouse-human (chuIgG4K) anti-C2-5F2.4, -35 and -60.

Example 13: Functional Activity of Chimeric Mouse-Human IgG4κ Anti-Human C2-5F2.4, -13, -32, -35 and -60

The chimeric mouse-human anti-C2 mAbs were tested in the same assays as described in Examples 4 (C3 fixation to solid-phase IgG), 5 (fluid-phase C3 activation in serum by aggregated IgG) and 6 (complement-dependent cytotoxicity by anti-HLA antibodies). The functional activities of the 5 chimeric mouse-human antibodies in these assays were similarly as described for the murine antibodies, i.e. they inhibited fixation of C3 to solid phase IgG, they inhibited the activation of C3 in serum by aggregated IgG (FIG. 14) and prevented complement-dependent cytotoxicity by anti-HLA antibodies (FIG. 15).

Example 14: Determination of N-Terminal Amino Acid Sequences of Variable Regions from Mouse Anti-C2-5F2.4, -35 and -60 with Primers Annealing in Signal Peptide Regions As mentioned in Example 10, theoretically, consensus mouse N-terminal amino acid sequences of variable regions can differ from determined sequences due to the use of degenerated sense primers. Therefore, the VH and VL regions of anti-C2-5F2.4, -35, and -60 were determined again using primers, which are described in Table 5, i.e., the sense primers anneal in signal peptide regions of murine antibodies.

TABLE 5

PCR primers used to amplify consensus mouse variable heavy and variable light chain regions of anti-C2-5F2.4, -35 and -60

| region+ | no. | primer sequence** | |
|---|---|---|---|
| 5F2.4 VL | 393 | ATGGAAGCCCCAGCTCAGCTTCTCTTCC | s |
| | 394 | ACTGGATGGTGGGAAGATGG | as |
| 5F2.4 VH | 410 | ATGGRATGGAGCKGGGTCTTTMTCTT | s |
| | 417 | CAGTGGATAGACCGATGGGGG | as |
| 35 VL | 389 | ATGGGCWTCAAAGATGGAGTCACA | s |
| | 394 | ACTGGATGGTGGGAAGATGG | as |
| 35 VH | 404 | ATGAAATGCAGCTGGGGCATSTTCTTC | s |
| | 416 | CAGTGGATAGACAGATGGGGG | as |
| 60 VL | 383 | ATGAAGTTGCCTGTTAGGCTGTTGGTGCTG | s |
| | 394 | ACTGGATGGTGGGAAGATGG | as |
| 60 VH | 413 | ATGGGCAGACTTACATTCTCATTCCTG | s |
| | 416 | CAGTGGATAGACAGATGGGGG | as | s = sense; as = antisense
+VL = variable light chain region, VH = variable heavy chain region; * no according to Bioceros internal coding system; ' primers: M = C or A; V = G, A, or C; N = A, C, G, or T; Y = C or T; R = A or G; W = A or T; and S = G or C.

RNA was isolated from hybridoma cells by using RNeasy Mini Isolation Kit (QIAGEN). RNA concentration was determined (A260 nm), and RNA was stored at −80° C. By reverse transcriptase, cDNA was synthesized from 2 μg of RNA using the RevertAid™ H Minus First Strand cDNA Synthesis Kit (Fermentas), and stored at −20° C.

Accuprime™ Pfx DNA Polymerase (Invitrogen) was used to amplify the variable regions of heavy and light chains of mouse anti-C2-5F2.4, -35 and -60. Used primer sets are shown in Table 5. The PCR products were gel-purified and cloned in the pCR-Blunt II-TOPO® vector for sequence analysis. From plasmids containing a PCR insert, cloned inserts were analysed by DNA sequencing (performed by Macrogen, Amsterdam, The Netherlands) to obtain the consensus sequence for V-regions of these three anti-C2 mAbs. At least 3 informative sequences of VH and of VL were obtained for all examined mAbs.

By using primer sets from Table 5, the consensus mouse variable heavy chain amino acid sequence of anti-C2-5F2.4, and consensus mouse variable light chain amino acid sequences of anti-C2-35 and -60 were found to be identical to amino acid sequences found in Example 10 (i.e., SEQ ID NO. 2, 27, and 35, respectively).

However, the N-terminal variable light chain amino acid sequence of anti-C2-5F2.4 (SEQ ID NO. 96) differed one amino acid (I2N) from the N-terminal variable light chain amino acid sequence anti-C2-5F2.4 (SEQ ID NO. 3) found in Example 10. The N-terminal variable heavy chain amino acid sequence of anti-C2-35 (SEQ ID NO. 97) differed one amino acid (Q1E) from the N-terminal variable heavy chain amino acid sequence of anti-C2-35 (SEQ ID NO. 26) found in Example 10. The N-terminal variable heavy chain amino acid sequence of anti-C2-60 (SEQ ID NO. 98) differed three amino acids (Q3A, Q5K, and Q6E) from the N-terminal variable heavy chain amino acid sequence of anti-C2-60 (SEQ ID NO. 34) found in Example 10.

Example 15: Generation of Humanized IgG4/Kappa Anti-Human Complement C2-5F2.4

Based on determined murine V-regions (SEQ ID NO: 2 for VH region, and SEQ ID NO: 96 for VL region, see Example 13) of mouse anti-C2-5F2.4, humanized antibody versions were generated.

Humanized variable light chain sequences and humanized variable heavy chain sequences of mouse anti-C2-5F2.4 were obtained using Germline Humanisation (CDR-grafting) technology (performed by Antitope Ltd, Cambridge, UK). For humanized variable light chain and heavy chain amino acid sequences, see SEQ ID NO. 99 (5F2.4-VL1), 100 (5F2.4-VL2), 101 (5F2.4-VL3), 102 (5F2.4-VL4), and 103 (5F2.4-VH1), 104 (5F2.4VH2), 105 (5F2.4-VH3), 106 (5F2.4-VH4), respectively.

After this design, cDNA sequences (see SEQ ID NO. 107, 108, 109, and 110 (coding for full length humanized light κ chain 5F2.4 versions, i.e., VL1, VL2, VL3, and VL4, resp.), and SEQ ID NO. 111, 112, 113, and 114 (coding for full length humanized heavy IgG4 5F2.4 versions, i.e., VH1, VH2, VH3, and VH4, resp.)) were purchased from GENEART (Regensburg, Germany), which code for a signal peptide followed by either the humanized variable light chain linked to human kappa constant region, and a signal peptide followed by the humanized variable heavy chain linked to human IgG4 constant region. Furthermore, all humanized antibodies were expressed as stabilized (Angal et al., Mol Immunol 1993, 30: 105) human IgG4 molecules. Using suitable restriction enzymes, generated cDNAs were subcloned in pcDNA3.1-derived expression plasmids.

Humanized anti-C2-5F2.4 versions were expressed using the FreeStyle™ 293 Expression System (Life Technologies). Generated humanized antibodies were purified using affinity chromatography protein A columns (GE Healthcare). In this manner, eight purified humanized versions of antibody 5F2.4 were generated, i.e., VL1VH1, VL2VH1, VL1VH2, VL2VH2, VL3VH3, VL4VH3, VL3VH4, and VL4VH4.

For full length humanized anti-C2-5F2.4 antibody amino acid sequences, see SEQ ID NO. 115, 116, 117, and 118 (coding for humanized light κ chain 5F2.4 versions, i.e., VL1, VL2, VL3, and VL4, resp.), and SEQ ID NO. 119, 120, 121, and 122 (coding for humanized heavy IgG4 chain 5F2.4 versions, i.e., VH1, VH2, VH3, and VH4, resp.).

Example 16: Binding Characterization of Humanized IgG4/Kappa Anti-Human Complement C2-5F2.4

Binding of humanized anti-C2-5F2.4 mAbs versions VL3VH3, VL4VH3, VL3VH4, and VL4VH4 to C2 was assessed by ELISA like described above in Example 12 (recombinant human C2 was immobilized to plates at 2 μg/ml). As shown in FIG. 17, all four examined humanized anti-5F2.4 mAb versions demonstrated similar binding to solid phase C2 compared with chimeric anti-C2-5F2.4 mAb.

Example 17: Functional Activity of Humanized IgG4/Kappa Anti-Human Complement C2-5F2.4

Modified cross test experiments were carried out similarly as described for mouse anti-C2 antibodies in Example 6.

First anti-HLA monoclonal antibody (clone W6/32) was used to sensitize cells. The chimeric anti-C2-5F2.4 and humanized anti-C2 antibodies versions VL3VH3, VL4VH3, VL3VH4, and VL4VH4 were tested at molar Ab:C2 ratios, which ranged from 5:1 to 0.312:1 (native C2 concentration in normal serum was assumed to be 20 μg/ml). All anti-C2 mAbs (chimeric and four examined humanized Ab versions) dose-dependently inhibited complement-dependent killing of anti-HLA antibody W6/32-sensitized cells (see FIG. 18). VL3-containing versions (i.e., VL3VH3 and VL3VH4) showed comparable inhibition to chimeric anti-C2-5F2.4 mAb in the cross test. In addition, VL3-containing versions (i.e., VL3VH3 and VL3VH4) seemed to outperform VL4-containing versions (i.e., VL4VH3 and VL4VH4).

In addition, a cross test using patient serum containing high levels of anti-HLA antibodies to sensitize cells was also performed, which resembles the physiological situation more closely. The chimeric anti-C2-5F2.4 and humanized anti-C2 antibodies versions VL3VH3, VL4VH3, VL3VH4, and VL4VH4 were tested at 160 μg/ml. All anti-C2 mAbs (chimeric and four examined humanized Ab versions) inhibited complement-dependent killing of serum anti-HLA antibody-sensitized cells (see FIG. 19).

---

The invention claimed is:

1. A nucleic acid molecule encoding a binding molecule or an antibody that binds to human complement factor C2, the binding molecule or antibody comprising an immunoglobulin heavy chain variable region and an immunoglobulin light chain variable region
   (a) comprising the amino acid sequences of SEQ ID NO: 2 and SEQ ID NO: 3 respectively; SEQ ID NO: 2 and SEQ ID NO: 96 respectively; SEQ ID NO: 10 and SEQ ID NO: 11 respectively; SEQ ID NO: 18 and SEQ ID NO: 19 respectively; SEQ ID NO: 26 and SEQ ID NO: 27 respectively; SEQ ID NO: 97 and SEQ ID NO: 27 respectively; SEQ ID NO: 34 and SEQ ID NO: 35 respectively; or SEQ ID NO: 98 and SEQ ID NO: 35 respectively; or
   (b) comprising the amino acid sequences of SEQ ID NO: 103 and SEQ ID NO: 99 respectively; SEQ ID NO: 104 and SEQ ID NO: 99 respectively; SEQ ID NO: 105 and SEQ ID NO: 99 respectively; SEQ ID NO: 106 and SEQ ID NO: 99 respectively; SEQ ID NO: 103 and SEQ ID NO: 100 respectively; SEQ ID NO: 104 and SEQ ID NO: 100 respectively; SEQ ID NO: 105 and SEQ ID NO: 100 respectively; SEQ ID NO: 106 and SEQ ID NO: 100 respectively; SEQ ID NO: 103 and SEQ ID NO: 101 respectively; SEQ ID NO: 104 and SEQ ID NO: 101 respectively; SEQ ID NO: 105 and SEQ ID NO: 101 respectively; SEQ ID NO: 106 and SEQ ID NO: 101 respectively; SEQ ID NO: 103 and SEQ ID NO: 102 respectively; SEQ ID NO: 104 and SEQ ID NO: 102 respectively; SEQ ID NO: 105 and SEQ ID NO: 102 respectively; or SEQ ID NO: 106 and SEQ ID NO: 102 respectively; or
   (c) comprising the amino acid sequences specified under (a) and/or (b) but wherein one or both of said sequences comprise 1-5 amino acid substitutions not in a CDR region.

2. The nucleic acid molecule according to claim 1, comprising the nucleic acid sequences of SEQ ID NO: 42; SEQ ID NO: 43; SEQ ID NO: 44; SEQ ID NO: 45; SEQ ID NO: 46; SEQ ID NO: 47; SEQ ID NO: 48; SEQ ID NO: 49; SEQ ID NO: 50; SEQ ID NO: 51; SEQ ID NO: 52; SEQ ID NO: 107; SEQ ID NO: 108; SEQ ID NO: 109; SEQ ID NO: 110; SEQ ID NO: 111; SEQ ID NO: 112; SEQ ID NO: 113; or SEQ ID NO: 114.

3. The nucleic acid molecule according to claim 1, wherein the binding molecule is a Fab fragment, a single chain Fv (scFv) fragment, or an antigen binding fragment thereof of an antibody.

4. The nucleic acid molecule according to claim 1, wherein the binding molecule or antibody is a humanized or deimmunized IgG, IgA, IgD, IgE or IgM antibody, such as IgG1, IgG2, IgG3 or IgG4 antibody.

5. The nucleic acid molecule according to claim 4, wherein the humanized or deimmunized antibody
   (a) comprises the amino acid sequences of SEQ ID NO: 53 and SEQ ID NO: 54; SEQ ID NO: 55 and SEQ ID NO: 56; SEQ ID NO: 57 and SEQ ID NO: 58; SEQ ID NO: 57 and SEQ ID NO: 59; SEQ ID NO: 60 and SEQ ID NO: 61; or SEQ ID NO: 62 and SEQ ID NO: 63; or
   (b) comprises the amino acid sequences of SEQ ID NO: 115 and SEQ ID NO: 119; SEQ ID NO: 115 and SEQ ID NO: 120; SEQ ID NO: 115 and SEQ ID NO: 121; SEQ ID NO: 115 and SEQ ID NO: 122; SEQ ID NO: 116 and SEQ ID NO: 119; SEQ ID NO: 116 and SEQ ID NO: 120; SEQ ID NO: 116 and SEQ ID NO: 121; SEQ ID NO: 116 and SEQ ID NO: 122; SEQ ID NO: 117 and SEQ ID NO: 119; SEQ ID NO: 117 and SEQ ID NO: 120; SEQ ID NO: 117 and SEQ ID NO: 121; SEQ ID NO: 117 and SEQ ID NO: 122; SEQ ID NO: 118 and SEQ ID NO: 119; SEQ ID NO: 118 and SEQ ID NO: 120; SEQ ID NO: 118 and SEQ ID NO: 121; or SEQ ID NO: 118 and SEQ ID NO: 122; or
   (c) comprises the amino acid sequences specified under (a) and/or (b) but wherein one or both of said sequences comprise 1-5 amino acid substitutions not in a CDR region.

6. A gene delivery vehicle or vector comprising a nucleic acid molecule according to claim 1.

7. An isolated or recombinant cell, or in vitro cell culture cell comprising a nucleic acid molecule according to claim 1.

8. An isolated or recombinant cell, or in vitro cell culture cell comprising the gene delivery vehicle or vector according to claim 6.

9. The cell of claim 7, wherein the cell is selected from the group consisting of a hybridoma cell line, a CHO cell, and an NS0 cell.

10. A method for producing a binding molecule comprising: culturing the cell of claim 7, and harvesting the binding molecule produced by the cell.

11. A nucleic acid molecule encoding a binding molecule or an antibody that binds to human complement factor C2, the binding molecule or antibody comprising an immunoglobulin heavy chain variable region and an immunoglobulin light chain variable region,
   wherein the heavy chain variable region comprises:
      (a) a heavy chain CDR1 comprising the amino acid sequence of SEQ ID NO:4;
      (b) a heavy chain CDR2 comprising the amino acid sequence of SEQ ID NO:5; and
      (c) a heavy chain CDR3 comprising the amino acid sequence of SEQ ID NO:6;
   and wherein the light chain variable region comprises:
      (d) a light chain CDR1 comprising the amino acid sequence of SEQ ID NO:7;

(e) a light chain CDR2 comprising the amino acid sequence of SEQ ID NO:8; and (f) a light chain CDR3 comprising the amino acid sequence of SEQ ID NO:9.

12. The nucleic acid molecule according to claim 11, wherein the binding molecule is a Fab fragment, a single chain Fv (scFv) fragment, or an antigen binding fragment thereof of an antibody.

13. The nucleic acid molecule according to claim 11, wherein the binding molecule or antibody is a humanized or deimmunized IgG, IgA, IgD, IgE or IgM antibody, such as IgG1, IgG2, IgG3 or IgG4 antibody.

14. An isolated or recombinant cell, or in vitro cell culture cell comprising a nucleic acid molecule according to claim 11.

15. A method for producing a binding molecule comprising: culturing the cell of claim 14, and harvesting the binding molecule produced by the cell.

16. A nucleic acid molecule encoding a binding molecule or an antibody that binds to human complement factor C2, the binding molecule or antibody comprising an immunoglobulin heavy chain variable region comprising the amino acid sequence encoded by SEQ ID NO: 114; and an immunoglobulin light chain variable region comprising the amino acid sequence encoded by SEQ ID NO: 109.

17. The nucleic acid molecule according to claim 16, wherein the binding molecule is a Fab fragment, a single chain Fv (scFv) fragment, or an antigen binding fragment thereof of an antibody.

18. The nucleic acid molecule according to claim 16, wherein the binding molecule or antibody is a humanized or deimmunized IgG, IgA, IgD, IgE or IgM antibody, such as IgG1, IgG2, IgG3 or IgG4 antibody.

19. An isolated or recombinant cell, or in vitro cell culture cell comprising a nucleic acid molecule according to claim 16.

20. A method for producing a binding molecule comprising: culturing the cell of claim 19, and harvesting the binding molecule produced by the cell.

* * * * *

SEQUENCE LISTING

```
<160> NUMBER OF SEQ ID NOS: 122

<210> SEQ ID NO 1
<211> LENGTH: 752
<212> TYPE: PRT
<213> ORGANISM: Homo sapiens

<400> SEQUENCE: 1

Met Gly Pro Leu Met Val Leu Phe Cys Leu Leu Phe Leu Tyr Pro Gly
1               5                   10                  15

Leu Ala Asp Ser Ala Pro Ser Cys Pro Gln Asn Val Asn Ile Ser Gly
            20                  25                  30

Gly Thr Phe Thr Leu Ser His Gly Trp Ala Pro Gly Ser Leu Leu Thr
        35                  40                  45

Tyr Ser Cys Pro Gln Gly Leu Tyr Pro Ser Pro Ala Ser Arg Leu Cys
    50                  55                  60

Lys Ser Ser Gly Gln Trp Gln Thr Pro Gly Ala Thr Arg Ser Leu Ser
65                  70                  75                  80

Lys Ala Val Cys Lys Pro Val Arg Cys Pro Ala Pro Val Ser Phe Glu
                85                  90                  95

Asn Gly Ile Tyr Thr Pro Arg Leu Gly Ser Tyr Pro Val Gly Gly Asn
                100                 105                 110

Val Ser Phe Glu Cys Glu Asp Gly Phe Ile Leu Arg Gly Ser Pro Val
            115                 120                 125

Arg Gln Cys Arg Pro Asn Gly Met Trp Asp Gly Glu Thr Ala Val Cys
        130                 135                 140

Asp Asn Gly Ala Gly His Cys Pro Asn Pro Gly Ile Ser Leu Gly Ala
145                 150                 155                 160

Val Arg Thr Gly Phe Arg Phe Gly His Gly Asp Lys Val Arg Tyr Arg
                165                 170                 175

Cys Ser Ser Asn Leu Val Leu Thr Gly Ser Ser Glu Arg Glu Cys Gln
```

-continued

Gly Asn Gly Val Trp Ser Gly Thr Glu Pro Ile Cys Arg Gln Pro Tyr
180             185                 190
            195                 200             205

Ser Tyr Asp Phe Pro Glu Asp Val Ala Pro Ala Leu Gly Thr Ser Phe
    210             215                 220

Ser His Met Leu Gly Ala Thr Asn Pro Thr Gln Lys Thr Lys Glu Ser
225             230                  235                 240

Leu Gly Arg Lys Ile Gln Ile Gln Arg Ser Gly His Leu Asn Leu Tyr
                245                 250                 255

Leu Leu Leu Asp Cys Ser Gln Ser Val Ser Glu Asn Asp Phe Leu Ile
            260             265                 270

Phe Lys Glu Ser Ala Ser Leu Met Val Asp Arg Ile Phe Ser Phe Glu
        275                 280                 285

Ile Asn Val Ser Val Ala Ile Ile Thr Phe Ala Ser Glu Pro Lys Val
    290                 295                 300

Leu Met Ser Val Leu Asn Asp Asn Ser Arg Asp Met Thr Glu Val Ile
305             310                 315                 320

Ser Ser Leu Glu Asn Ala Asn Tyr Lys Asp His Glu Asn Gly Thr Gly
                325                 330                 335

Thr Asn Thr Tyr Ala Ala Leu Asn Ser Val Tyr Leu Met Met Asn Asn
            340                 345                 350

Gln Met Arg Leu Leu Gly Met Glu Thr Met Ala Trp Gln Glu Ile Arg
            355                 360                 365

His Ala Ile Ile Leu Leu Thr Asp Gly Lys Ser Asn Met Gly Gly Ser
        370                 375                 380

Pro Lys Thr Ala Val Asp His Ile Arg Glu Ile Leu Asn Ile Asn Gln
385                 390                 395                 400

Lys Arg Asn Asp Tyr Leu Asp Ile Tyr Ala Ile Gly Val Gly Lys Leu
                405                 410                 415

Asp Val Asp Trp Arg Glu Leu Asn Glu Leu Gly Ser Lys Lys Asp Gly
                420                 425                 430

Glu Arg His Ala Phe Ile Leu Gln Asp Thr Lys Ala Leu His Gln Val
            435                 440                 445

Phe Glu His Met Leu Asp Val Ser Lys Leu Thr Asp Thr Ile Cys Gly
        450                 455                 460

Val Gly Asn Met Ser Ala Asn Ala Ser Asp Gln Glu Arg Thr Pro Trp
465                 470                 475                 480

His Val Thr Ile Lys Pro Lys Ser Gln Glu Thr Cys Arg Gly Ala Leu
                485                 490                 495

Ile Ser Asp Gln Trp Val Leu Thr Ala Ala His Cys Phe Arg Asp Gly
            500                 505                 510

Asn Asp His Ser Leu Trp Arg Val Asn Val Gly Asp Pro Lys Ser Gln
            515                 520                 525

Trp Gly Lys Glu Phe Leu Ile Glu Lys Ala Val Ile Ser Pro Gly Phe
            530                 535                 540

Asp Val Phe Ala Lys Lys Asn Gln Gly Ile Leu Glu Phe Tyr Gly Asp
545                 550                 555                 560

Asp Ile Ala Leu Leu Lys Leu Ala Gln Lys Val Lys Met Ser Thr His
                565                 570                 575

Ala Arg Pro Ile Cys Leu Pro Cys Thr Met Glu Ala Asn Leu Ala Leu
            580                 585                 590

Arg Arg Pro Gln Gly Ser Thr Cys Arg Asp His Glu Asn Glu Leu Leu
            595                 600                 605

```
Asn Lys Gln Ser Val Pro Ala His Phe Val Ala Leu Asn Gly Ser Lys
        610                 615                 620

Leu Asn Ile Asn Leu Lys Met Gly Val Glu Trp Thr Ser Cys Ala Glu
625                 630                 635                 640

Val Val Ser Gln Glu Lys Thr Met Phe Pro Asn Leu Thr Asp Val Arg
                645                 650                 655

Glu Val Val Thr Asp Gln Phe Leu Cys Ser Gly Thr Gln Glu Asp Glu
                660                 665                 670

Ser Pro Cys Lys Gly Glu Ser Gly Gly Ala Val Phe Leu Glu Arg Arg
            675                 680                 685

Phe Arg Phe Phe Gln Val Gly Leu Val Ser Trp Gly Leu Tyr Asn Pro
690                 695                 700

Cys Leu Gly Ser Ala Asp Lys Asn Ser Arg Lys Arg Ala Pro Arg Ser
705                 710                 715                 720

Lys Val Pro Pro Arg Asp Phe His Ile Asn Leu Phe Arg Met Gln
                725                 730                 735

Pro Trp Leu Arg Gln His Leu Gly Asp Val Leu Asn Phe Leu Pro Leu
                740                 745                 750

<210> SEQ ID NO 2
<211> LENGTH: 118
<212> TYPE: PRT
<213> ORGANISM: Artificial Sequence
<220> FEATURE:
<223> OTHER INFORMATION: Amino acid sequence of no. 5F2.4 heavy chain
      variable region

<400> SEQUENCE: 2

Glu Val Gln Leu Gln Gln Ser Gly Ala Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Asp Ile Asn Pro Asn Tyr Glu Ser Thr Gly Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Glu Asp Asp His Asp Ala Phe Ala Tyr Trp Gly Gln Gly Thr
            100                 105                 110

Leu Val Thr Val Ser Ala
        115

<210> SEQ ID NO 3
<211> LENGTH: 112
<212> TYPE: PRT
<213> ORGANISM: Artificial Sequence
<220> FEATURE:
<223> OTHER INFORMATION: Amino acid sequence of no. 5F2.4 light chain
      variable region

<400> SEQUENCE: 3

Asp Ile Val Leu Thr Gln Ser Pro Ala Ser Val Val Val Ser Leu Gly
1               5                   10                  15

Gln Arg Ala Thr Ile Ser Cys Arg Ala Ser Lys Ser Val Arg Thr Ser
            20                  25                  30
```

-continued

```
Gly Tyr Asn Tyr Met His Trp Tyr Gln Gln Lys Pro Gly Gln Pro Pro
         35                  40                  45

Lys Leu Leu Ile Tyr Leu Ala Ser Asn Leu Lys Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Ala Asp Ala Ala Thr Tyr Tyr Cys Gln His Ser Arg
                 85                  90                  95

Glu Leu Pro Tyr Thr Phe Gly Gly Gly Thr Lys Leu Glu Ile Lys Arg
            100                 105                 110

<210> SEQ ID NO 4
<211> LENGTH: 5
<212> TYPE: PRT
<213> ORGANISM: Artificial Sequence
<220> FEATURE:
<223> OTHER INFORMATION: Amino acid sequence of no. 5F2.4 heavy chain
      CDR1

<400> SEQUENCE: 4

Asp Tyr Asn Met Asp
 1               5

<210> SEQ ID NO 5
<211> LENGTH: 17
<212> TYPE: PRT
<213> ORGANISM: Artificial Sequence
<220> FEATURE:
<223> OTHER INFORMATION: Amino acid sequence of no. 5F2.4 heavy chain
      CDR2

<400> SEQUENCE: 5

Asp Ile Asn Pro Asn Tyr Glu Ser Thr Gly Tyr Asn Gln Lys Phe Lys
 1               5                  10                  15

Gly

<210> SEQ ID NO 6
<211> LENGTH: 9
<212> TYPE: PRT
<213> ORGANISM: Artificial Sequence
<220> FEATURE:
<223> OTHER INFORMATION: Amino acid sequence of no. 5F2.4 heavy chain
      CDR3

<400> SEQUENCE: 6

Glu Asp Asp His Asp Ala Phe Ala Tyr
 1               5

<210> SEQ ID NO 7
<211> LENGTH: 15
<212> TYPE: PRT
<213> ORGANISM: Artificial Sequence
<220> FEATURE:
<223> OTHER INFORMATION: Amino acid sequence of no. 5F2.4 light chain
      CDR1

<400> SEQUENCE: 7

Arg Ala Ser Lys Ser Val Arg Thr Ser Gly Tyr Asn Tyr Met His
 1               5                  10                  15

<210> SEQ ID NO 8
<211> LENGTH: 7
<212> TYPE: PRT
<213> ORGANISM: Artificial Sequence
```

```
<220> FEATURE:
<223> OTHER INFORMATION: Amino acid sequence of no. 5F2.4 light chain
      CDR2

<400> SEQUENCE: 8

Leu Ala Ser Asn Leu Lys Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Amino acid sequence of no. 5F2.4 light chain
      CDR3

<400> SEQUENCE: 9

Gln His Ser Arg Glu Leu Pro Tyr Thr
1               5

<210> SEQ ID NO 10
<211> LENGTH: 118
<212> TYPE: PRT
<213> ORGANISM: Artificial Sequence
<220> FEATURE:
<223> OTHER INFORMATION: Amino acid sequence of no. 13 heavy chain
      variable region

<400> SEQUENCE: 10

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ile Tyr
            20                  25                  30

Tyr Met Tyr Trp Val Lys Gln Arg Pro Gly Gln Gly Leu Glu Trp Ile
        35                  40                  45

Gly Glu Val Asp Pro Ser Ile Gly Gly Ile Ser Phe Asn Glu Lys Phe
    50                  55                  60

Lys Ser Lys Ala Thr Leu Thr Val Asp Arg Ser Ser Ser Thr Ala Tyr
65                  70                  75                  80

Met His Leu Ser Ser Leu Thr Ser Glu Asp Ser Ala Val Tyr Tyr Cys
                85                  90                  95

Thr Arg Gly Gly Thr Tyr Tyr Ala Met Asp Tyr Trp Gly Gln Gly Thr
            100                 105                 110

Ser Val Thr Val Ser Ser
        115

<210> SEQ ID NO 11
<211> LENGTH: 113
<212> TYPE: PRT
<213> ORGANISM: Artificial Sequence
<220> FEATURE:
<223> OTHER INFORMATION: Amino acid sequence of no. 13 light chain
      variable region

<400> SEQUENCE: 11

Asp Val Leu Met Thr Gln Thr Pro Leu Ser Leu Pro Val Ser Leu Gly
1               5                   10                  15

Asp Gln Ala Ser Ile Ser Cys Arg Ala Gly Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
```

```
                   50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                     85                  90                  95

Ser His Val Pro Trp Thr Phe Gly Gly Gly Thr Lys Leu Glu Ile Lys
                100                 105                 110

Arg

<210> SEQ ID NO 12
<211> LENGTH: 5
<212> TYPE: PRT
<213> ORGANISM: Artificial Sequence
<220> FEATURE:
<223> OTHER INFORMATION: Amino acid sequence of no. 13 heavy chain CDR1

<400> SEQUENCE: 12

Ile Tyr Tyr Met Tyr
 1               5

<210> SEQ ID NO 13
<211> LENGTH: 17
<212> TYPE: PRT
<213> ORGANISM: Artificial Sequence
<220> FEATURE:
<223> OTHER INFORMATION: Amino acid sequence of no. 13 heavy chain CDR2

<400> SEQUENCE: 13

Glu Val Asp Pro Ser Ile Gly Gly Ile Ser Phe Asn Glu Lys Phe Lys
 1               5                  10                  15

Ser

<210> SEQ ID NO 14
<211> LENGTH: 9
<212> TYPE: PRT
<213> ORGANISM: Artificial Sequence
<220> FEATURE:
<223> OTHER INFORMATION: Amino acid sequence of no. 13 heavy chain CDR3

<400> SEQUENCE: 14

Gly Gly Thr Tyr Tyr Ala Met Asp Tyr
 1               5

<210> SEQ ID NO 15
<211> LENGTH: 16
<212> TYPE: PRT
<213> ORGANISM: Artificial Sequence
<220> FEATURE:
<223> OTHER INFORMATION: Amino acid sequence of no. 13 light chain CDR1

<400> SEQUENCE: 15

Arg Ala Gly Gln Ser Ile Val His Ser Asn Gly Asn Thr Tyr Leu Glu
 1               5                  10                  15

<210> SEQ ID NO 16
<211> LENGTH: 7
<212> TYPE: PRT
<213> ORGANISM: Artificial Sequence
<220> FEATURE:
<223> OTHER INFORMATION: Amino acid sequence of no. 13 light chain CDR2

<400> SEQUENCE: 16

Lys Val Ser Asn Arg Phe Ser
 1               5
```

<210> SEQ ID NO 17
<211> LENGTH: 9
<212> TYPE: PRT
<213> ORGANISM: Artificial Sequence
<220> FEATURE:
<223> OTHER INFORMATION: Amino acid sequence of no. 13 light chain CDR3

<400> SEQUENCE: 17

Phe Gln Gly Ser His Val Pro Trp Thr
1               5

<210> SEQ ID NO 18
<211> LENGTH: 118
<212> TYPE: PRT
<213> ORGANISM: Artificial Sequence
<220> FEATURE:
<223> OTHER INFORMATION: Amino acid sequence of no. 32 heavy chain
      variable region

<400> SEQUENCE: 18

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Asp Met Tyr Trp Val Lys Gln Arg Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ser Thr Ala His
65                  70                  75                  80

Met Gln Leu Ser Ser Leu Thr Ser Glu Asp Ser Ala Val Tyr Tyr Cys
                85                  90                  95

Thr Arg Gly Gly Thr Phe Tyr Ala Met Asp Tyr Trp Gly Gln Gly Thr
            100                 105                 110

Ser Val Thr Val Ser Ser
        115

<210> SEQ ID NO 19
<211> LENGTH: 113
<212> TYPE: PRT
<213> ORGANISM: Artificial Sequence
<220> FEATURE:
<223> OTHER INFORMATION: Amino acid sequence of no. 32 light chain
      variable region

<400> SEQUENCE: 19

Asp Ile Gln Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys

```
                      100                 105                 110
Arg

<210> SEQ ID NO 20
<211> LENGTH: 5
<212> TYPE: PRT
<213> ORGANISM: Artificial Sequence
<220> FEATURE:
<223> OTHER INFORMATION: Amino acid sequence of no. 32 heavy chain CDR1

<400> SEQUENCE: 20

Ser Tyr Asp Met Tyr
1               5

<210> SEQ ID NO 21
<211> LENGTH: 17
<212> TYPE: PRT
<213> ORGANISM: Artificial Sequence
<220> FEATURE:
<223> OTHER INFORMATION: Amino acid sequence of no. 32 heavy chain CDR2

<400> SEQUENCE: 21

Glu Ile Asn Pro Ser Asn Gly Asp Thr Asn Phe Asn Glu Lys Phe Lys
1               5                   10                  15

Ser

<210> SEQ ID NO 22
<211> LENGTH: 9
<212> TYPE: PRT
<213> ORGANISM: Artificial Sequence
<220> FEATURE:
<223> OTHER INFORMATION: Amino acid sequence of no. 32 heavy chain CDR3

<400> SEQUENCE: 22

Gly Gly Thr Phe Tyr Ala Met Asp Tyr
1               5

<210> SEQ ID NO 23
<211> LENGTH: 16
<212> TYPE: PRT
<213> ORGANISM: Artificial Sequence
<220> FEATURE:
<223> OTHER INFORMATION: Amino acid sequence of no. 32 light chain CDR1

<400> SEQUENCE: 23

Arg Ser Ser Gln Ser Ile Val His Ser Asn Gly Asn Thr Tyr Leu Glu
1               5                   10                  15

<210> SEQ ID NO 24
<211> LENGTH: 7
<212> TYPE: PRT
<213> ORGANISM: Artificial Sequence
<220> FEATURE:
<223> OTHER INFORMATION: Amino acid sequence of no. 32 light chain CDR2

<400> SEQUENCE: 24

Lys Val Ser Asn Arg Phe Ser
1               5

<210> SEQ ID NO 25
<211> LENGTH: 9
<212> TYPE: PRT
<213> ORGANISM: Artificial Sequence
<220> FEATURE:
<223> OTHER INFORMATION: Amino acid sequence of no. 32 light chain CDR3
```

```
<400> SEQUENCE: 25

Phe Gln Gly Ser His Val Pro Trp Thr
1               5

<210> SEQ ID NO 26
<211> LENGTH: 117
<212> TYPE: PRT
<213> ORGANISM: Artificial Sequence
<220> FEATURE:
<223> OTHER INFORMATION: Amino acid sequence of no. 35 heavy chain
      variable region

<400> SEQUENCE: 26

Gln Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Glu Trp Lys Phe Tyr Ala Met Asp Asp Trp Gly Gln Gly Thr Ser
            100                 105                 110

Val Thr Val Ser Ser
        115

<210> SEQ ID NO 27
<211> LENGTH: 114
<212> TYPE: PRT
<213> ORGANISM: Artificial Sequence
<220> FEATURE:
<223> OTHER INFORMATION: Amino acid sequence of no. 35 light chain
      variable region

<400> SEQUENCE: 27

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Arg Thr Phe Gly Gly Gly Thr Lys Leu Glu Ile
            100                 105                 110

Lys Arg

<210> SEQ ID NO 28
<211> LENGTH: 5
<212> TYPE: PRT
<213> ORGANISM: Artificial Sequence
```

```
<220> FEATURE:
<223> OTHER INFORMATION: Amino acid sequence of no. 35 heavy chain CDR1

<400> SEQUENCE: 28

Asp Tyr Tyr Met His
1               5

<210> SEQ ID NO 29
<211> LENGTH: 17
<212> TYPE: PRT
<213> ORGANISM: Artificial Sequence
<220> FEATURE:
<223> OTHER INFORMATION: Amino acid sequence of no. 35 heavy chain CDR2

<400> SEQUENCE: 29

Trp Ile Asp Pro Glu Asn Gly Asp Thr Glu Tyr Ala Pro Lys Phe Gln
1               5                   10                  15

Gly

<210> SEQ ID NO 30
<211> LENGTH: 8
<212> TYPE: PRT
<213> ORGANISM: Artificial Sequence
<220> FEATURE:
<223> OTHER INFORMATION: Amino acid sequence of no. 35 heavy chain CDR3

<400> SEQUENCE: 30

Trp Lys Phe Tyr Ala Met Asp Asp
1               5

<210> SEQ ID NO 31
<211> LENGTH: 17
<212> TYPE: PRT
<213> ORGANISM: Artificial Sequence
<220> FEATURE:
<223> OTHER INFORMATION: Amino acid sequence of no. 35 light chain CDR1

<400> SEQUENCE: 31

Lys Ser Ser Gln Ser Leu Leu Tyr Ser Ser Asn Gln Lys Asn Tyr Leu
1               5                   10                  15

Ala

<210> SEQ ID NO 32
<211> LENGTH: 7
<212> TYPE: PRT
<213> ORGANISM: Artificial Sequence
<220> FEATURE:
<223> OTHER INFORMATION: Amino acid sequence of no. 35 light chain CDR2

<400> SEQUENCE: 32

Trp Ala Ser Thr Arg Glu Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Amino acid sequence of no. 35 light chain CDR3

<400> SEQUENCE: 33

Gln Gln Tyr Tyr Ser Tyr Pro Arg Thr
1               5

<210> SEQ ID NO 34
```

```
<211> LENGTH: 124
<212> TYPE: PRT
<213> ORGANISM: Artificial Sequence
<220> FEATURE:
<223> OTHER INFORMATION: Amino acid sequence of no. 60 heavy chain
      variable region

<400> SEQUENCE: 34

Gln Val Gln Leu Gln Gln Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Asn Met Gly Val Gly Trp Ile Arg Gln Pro Ser Gly Lys Gly Leu Glu
        35                  40                  45

Trp Leu Ala His Ile Trp Trp Asp Asp Lys Arg Tyr Asn Pro Ala
    50                  55                  60

Leu Lys Ser Arg Leu Thr Ile Ser Lys Asp Thr Ser Ser Asn Gln Val
65                  70                  75                  80

Phe Leu Lys Ile Ala Ser Val Asp Thr Ala Asp Thr Ala Thr Tyr Phe
                85                  90                  95

Cys Ala Arg Ile Gly Arg Pro Thr Met Ile Thr Thr Trp Tyr Leu Asp
            100                 105                 110

Val Trp Gly Ala Gly Thr Thr Val Thr Val Ser Ser
        115                 120

<210> SEQ ID NO 35
<211> LENGTH: 108
<212> TYPE: PRT
<213> ORGANISM: Artificial Sequence
<220> FEATURE:
<223> OTHER INFORMATION: Amino acid sequence of no. 60 light chain
      variable region

<400> SEQUENCE: 35

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Lys Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Asn Tyr Tyr Cys Gln His Phe Trp Asn Thr Pro Tyr
                85                  90                  95

Thr Phe Gly Gly Gly Thr Lys Leu Glu Ile Lys Arg
            100                 105

<210> SEQ ID NO 36
<211> LENGTH: 7
<212> TYPE: PRT
<213> ORGANISM: Artificial Sequence
<220> FEATURE:
<223> OTHER INFORMATION: Amino acid sequence of no. 60 heavy chain CDR1

<400> SEQUENCE: 36

Thr Ser Asn Met Gly Val Gly
1               5
```

```
<210> SEQ ID NO 37
<211> LENGTH: 16
<212> TYPE: PRT
<213> ORGANISM: Artificial Sequence
<220> FEATURE:
<223> OTHER INFORMATION: Amino acid sequence of no. 60 heavy chain CDR2

<400> SEQUENCE: 37

His Ile Trp Trp Asp Asp Lys Arg Tyr Asn Pro Ala Leu Lys Ser
1               5                   10                  15

<210> SEQ ID NO 38
<211> LENGTH: 14
<212> TYPE: PRT
<213> ORGANISM: Artificial Sequence
<220> FEATURE:
<223> OTHER INFORMATION: Amino acid sequence of no. 60 heavy chain CDR3

<400> SEQUENCE: 38

Ile Gly Arg Pro Thr Met Ile Thr Thr Trp Tyr Leu Asp Val
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Amino acid sequence of no. 60 light chain CDR1

<400> SEQUENCE: 39

Arg Ala Ser Glu Asn Ile Tyr Ser Asn Leu Ala
1               5                   10

<210> SEQ ID NO 40
<211> LENGTH: 7
<212> TYPE: PRT
<213> ORGANISM: Artificial Sequence
<220> FEATURE:
<223> OTHER INFORMATION: Amino acid sequence of no. 60 light chain CDR2

<400> SEQUENCE: 40

Ala Ala Thr Lys Leu Ala Asp
1               5

<210> SEQ ID NO 41
<211> LENGTH: 9
<212> TYPE: PRT
<213> ORGANISM: Artificial Sequence
<220> FEATURE:
<223> OTHER INFORMATION: Amino acid sequence of no. 60 light chain CDR3

<400> SEQUENCE: 41

Gln His Phe Trp Asn Thr Pro Tyr Thr
1               5

<210> SEQ ID NO 42
<211> LENGTH: 1392
<212> TYPE: DNA
<213> ORGANISM: Homo sapiens

<400> SEQUENCE: 42
atggaatgga gcggcgtgtt catgttcctg ctgtccgtga ccgcgggagt gcacagcgag      60
gtgcagctgc agcagtctgg agctgagctg gtgaagcctg gggcttcagt gaagatatcc     120
tgcaaggctt ctggctacac attcactgac tacaacatgg actgggtgaa acagagccat     180
ggaaagagcc ttgagtggat tggagatatt aatcctaatt atgaaagtac tgggtacaac     240
```

```
cagaagttca agggaaaggc cacattgact gttgacaagt cctccagcac agcctacatg      300
gaactccgca gcctgacatc tgaggacact gcagtctatt actgtgcaag agaggatgat      360
cacgacgcct ttgcttactg gggccaaggg actctggtca ctgtctctgc agctagcacc      420
aagggcccct ccgtgtttcc tctggcccct gctccagatc cacctccgac gtctaccgcc      480
gctctgggct gcctcgtgaa ggactacttc cccgagcccg tgacagtgtc ttggaactct      540
ggcgccctga cctccggcgt gcacacattt ccagctgtgc tgcagtcctc cggcctgtac      600
tccctgtcct ccgtcgtgac tgtgccttcc tctagcctgg caccaagac ctacacctgt       660 aacgtggacc acaagccctc caacaccaag gtggacaagc gggtggaatc taagtacggc      720
cctccttgcc caccctgccc tgccctgaa tttctgggcg gaccttccgt gttcctgttt        780
cccccaaagc caaggacac cctgatgatc tcccggaccc cgaagtgac ctgcgtggtg         840 gtggatgtgt cccaggaaga tcccgaggtg cagttcaatt ggtacgtgga cggcgtggaa      900
gtgcacaacg ccaagaccaa gcccagagag aacagttca actccaccta ccgggtggtg       960
tccgtgctga ccgtgctgca ccaggattgg ctgaacggca agagtacaa gtgcaaggtg      1020 tccaacaagg gcctgccctc cagcatcgaa aagaccatct ccaaggccaa gggccagccc      1080
cgggaacccc aggtgtacac actgcctcca agccaggaag atgaccaa gaaccaggtg       1140 tccctgacct gtctcgtgaa aggcttctac ccctccgata tcgccgtgga atgggagtcc      1200
aacggccagc ctgagaacaa ctacaagacc accccccctg tgctggactc cgacggctcc      1260
ttcttcctgt actctcgcct gaccgtggac aagtcccggt ggcaggaagg caacgtgttc      1320
tcctgctctg tgatgcacga ggccctgcac aaccactaca cccagaagtc cctgtccctg      1380
tctctgggca ag                                                          1392
```

<210> SEQ ID NO 43
<211> LENGTH: 711
<212> TYPE: DNA
<213> ORGANISM: Artificial Sequence
<220> FEATURE:
<223> OTHER INFORMATION: chimeric no. 5F2.4 human kappa chain

<400> SEQUENCE: 43

```
atggaatgga gcggcgtgtt catgttcctg ctgtccgtga ccgcgggagt gcacagcgac       60
attgtgctga cacagtctcc tgcttccgta gttgtatctc tggggcagag ggccaccatc      120
tcatgcaggg ccagcaaaag tgtcagaaca tctggctata attatatgca ctggtaccaa      180
cagaaaccag gacagccacc caaactcctc atctatcttg catccaacct aaaatctggg      240
gtccctgcca ggttcagtgg cagtgggtct gggacagact tcaccctcaa catccatcct      300
gtggaggagg cggatgctgc aacctattac tgtcagcaca gtagggagct tccgtacacg      360
ttcggagggg ggaccaagct ggaaataaaa cggaccgtag ccgcccttc cgtgttcatc      420 tttccaccct ccgacgagca gctgaagtct ggcaccgctt ccgtcgtgtg cctgctgaac      480
aacttctacc ccgcgaggc caaggtgcag tggaaggtgg acaacgccct gcagtccggc      540
aactcccagg aaagcgtgac cgagcaggac tccaaggaca gcacctactc cctgtcctcc      600
accctgaccc tgtccaaggc cgactacgag aagcacaagg tgtacgcctg cgaagtgacc      660
caccagggcc tgtctagccc cgtgaccaag tctttcaacc ggggcgagtg c               711
```

<210> SEQ ID NO 44
<211> LENGTH: 1392
<212> TYPE: DNA

<213> ORGANISM: Artificial Sequence
<220> FEATURE:
<223> OTHER INFORMATION: chimeric no. 13 human IgG4 chain

<400> SEQUENCE: 44

```
atggaatgga gcggcgtgtt catgttcctg ctgtccgtga ccgcgggagt gcacagtcag      60
gtccaactgc agcagcctgg ggctgaactg gtgaagcctg ggcttcagt gaagttgtcc     120
tgcaaggctt ctggctacac cttcaccatc tactatatgt actgggtgaa gcagaggcct     180
ggacaaggcc ttgagtggat tggggaggtt gatcctagca ttggtggtat tagcttcaat     240
gagaagttca gagcaaggc cacactgact gtagacagat cctccagcac agcatacatg     300
caccctcagca gcctgacatc tgaggactct gcggtctatt actgtacaag aggtgggacg     360
tactatgcta tggactactg gggtcaagga acctcagtca ccgtctcctc agctagcacc     420
aagggcccct ccgtgtttcc tctggcccct gctccagat ccacctccga gtctaccgcc     480
gctctgggct gcctcgtgaa ggactacttc cccgagcccg tgacagtgtc ttggaactct     540
ggcgccctga cctccggcgt gcacacattt ccagctgtgc tgcagtcctc cggcctgtac     600
tccctgtcct ccgtcgtgac tgtgccttcc tctagcctgg caccaagac ctacacctgt     660
aacgtggacc acaagccctc caacaccaag gtggacaagc gggtggaatc taagtacggc     720
cctccttgcc caccctgccc tgccctgaa tttctgggcg gaccttccgt gttcctgttt     780
ccccccaaagc caaggacac cctgatgatc tcccggaccc ccgaagtgac ctgcgtggtg     840
gtggatgtgt cccaggaaga tcccgaggtg cagttcaatt ggtacgtgga cggcgtggaa     900
gtgcacaacg ccaagaccaa gcccagagag aacagttca actccaccta ccgggtggtg     960
tccgtgctga ccgtgctgca ccaggattgg ctgaacggca agagtacaa gtgcaaggtg    1020
tccaacaagg gcctgccctc cagcatcgaa aagaccatct ccaaggccaa gggccagccc    1080
cgggaaccc agtgtacac actgcctcca gccaggaag gatgaccaa gaaccaggtg    1140
tccctgacct gtctcgtgaa aggcttctac ccctccgata tcgccgtgga atgggagtcc    1200
aacggccagc ctgagaacaa ctacaagacc accccccctg tgctggactc cgacggctcc    1260
ttcttcctgt actctcgcct gaccgtggac aagtcccggt ggcaggaagg caacgtgttc    1320
tcctgctctg tgatgcacga ggccctgcac aaccactaca cccagaagtc cctgtccctg    1380
tctctgggca ag                                                        1392
```

<210> SEQ ID NO 45
<211> LENGTH: 714
<212> TYPE: DNA
<213> ORGANISM: Artificial Sequence
<220> FEATURE:
<223> OTHER INFORMATION: chimeric no. 13 human kappa chain

<400> SEQUENCE: 45

```
atggaatgga gcggcgtgtt catgttcctg ctgtccgtga ccgcgggagt gcacagcgat      60
gtcctcatga cacaaacgcc tctctcccctg cctgtcagtc ttggagatca agcctccatc     120
tcttgcagag ctggtcagag cattgtacat agtaatggaa acacctattt agaatggtac     180
ctgcagaaac caggccagtc tccaaagctc ctgatctaca agtttccaa ccgattttct     240
ggggtcccag acaggttcag tggcagtgga tcaggacag atttcacact caagatcagc     300
agagtggagg ctgaggatct gggagtttat tactgctttc agggttcaca tgttccgtgg     360
acgttcggtg gaggcaccaa gctggaaatc aaacggaccg tagccgcccc ttccgtgttc     420
atctttccac cctccgacga gcagctgaag tctggcaccg cttccgtcgt gtgcctgctg     480
```

```
aacaacttct accccccgcga ggccaaggtg cagtggaagg tggacaacgc cctgcagtcc        540
ggcaactccc aggaaagcgt gaccgagcag gactccaagg acagcaccta ctccctgtcc        600
tccaccctga ccctgtccaa ggccgactac gagaagcaca aggtgtacgc ctgcgaagtg        660
acccaccagg gcctgtctag ccccgtgacc aagtctttca accggggcga gtgc              714
```

<210> SEQ ID NO 46
<211> LENGTH: 1392
<212> TYPE: DNA
<213> ORGANISM: Artificial Sequence
<220> FEATURE:
<223> OTHER INFORMATION: chimeric no. 32 human IgG4 chain

<400> SEQUENCE: 46

```
atggaatgga gcggcgtgtt catgttcctg ctgtccgtga ccgcgggagt gcacagtcag         60
gtgcagctgc agcagtctgg cgccgagctg gtgaaacctg gcgcctccgt gaagctgtcc        120
tgcaaggcct ccggctacac cttcaccagc tacgacatgt actgggtgaa acagcggcct        180
ggccagggcc tggaatggat cggcgagatc aaccccctcca acgcgacac caacttcaac        240 gagaagttca gtccaaggc caccctgacc gtggacaagt cctcctccac cgcccacatg         300
cagctgtcct ccctgacctc cgaggactcc gccgtgtact actgcaccag aggcggcacc        360
ttctacgcta tggactactg gggccagggc acctccgtga ccgtgtcctc tgctagcacc        420
aagggcccct ccgtgtttcc tctggcccct gctccagat ccacctccga gtctaccgcc         480
gctctgggct gcctcgtgaa ggactacttc cccgagccg tgacagtgtc ttggaactct        540
ggcgccctga cctccggcgt gcacacattt ccagctgtgc tgcagtcctc cggcctgtac       600
tccctgtcct ccgtcgtgac tgtgccttcc tctagcctgg gcaccaagac ctacacctgt       660
aacgtggacc acaagccctc caacaccaag gtggacaagc gggtggaatc taagtacggc       720
cctccttgcc cacctgccc tgcccctgaa tttctgggcg accttccgt gttcctgttt         780 cccccaaagc ccaaggacac cctgatgatc tcccggaccc cgaagtgac ctgcgtggtg        840 gtggatgtgt cccaggaaga tcccgaggtg cagttcaatt ggtacgtgga cggcgtggaa       900
gtgcacaacg ccaagaccaa gcccagagag gaacagttca ctccaccta ccgggtggtg       960 tccgtgctga ccgtgctgca ccaggattgg ctgaacggca agagtacaa gtgcaaggtg      1020 tccaacaagg gcctgccctc cagcatcgaa aagaccatct ccaaggccaa gggccagccc      1080
cgggaacccc aggtgtacac actgcctcca agccaggaag agatgaccaa gaaccaggtg      1140
tccctgacct gtctcgtgaa aggcttctac ccctccgata tcgccgtgga atgggagtcc      1200
aacggccagc ctgagaacaa ctacaagacc ccccccctg tgctggactc cgacggctcc      1260
ttcttcctgt actctcgcct gaccgtggac aagtccggt ggcaggaagg caacgtgttc      1320
tcctgctctg tgatgcacga ggccctgcac aaccactaca cccagaagtc cctgtccctg     1380
tctctgggca ag                                                         1392
```

<210> SEQ ID NO 47
<211> LENGTH: 1401
<212> TYPE: DNA
<213> ORGANISM: Artificial Sequence
<220> FEATURE:
<223> OTHER INFORMATION: CHO-optimized cDNA sequence coding for chimeric
      no. 32 human IgG1 chain

<400> SEQUENCE: 47

```
atggagtggt ccggcgtgtt catgttcctg ctgtccgtga ccgctggcgt gcactcccag         60
```

```
gtgcagctgc agcagtctgg cgccgagctg gtgaaacctg gcgcctccgt gaagctgtcc      120
tgcaaggcct ccggctacac cttcaccagc tacgacatgt actgggtgaa acagcggcct      180
ggccagggcc tggaatggat cggcgagatc aaccccctcca acggcgacac caacttcaac    240
gagaagttca gtccaaggcc caccctgacc gtggacaagt cctcctccac cgcccacatg      300
cagctgtcct ccctgacctc cgaggactcc gccgtgtact actgcaccag aggcggcacc      360
ttctacgcta tggactactg gggccagggc acctccgtga ccgtgtcctc tgcctccacc      420
aagggcccct ccgtgttccc tctggccccc tccagcaagt ccacctctgg cggcaccgct      480
gccctgggct gcctggtgaa agactacttc cccgagcctg tgacagtgtc ctggaactct      540
ggcgccctga ccagcggcgt gcacaccttc cctgccgtgc tgcagtcctc cggcctgtac      600
tccctgtcca gcgtggtgac agtgccctcc tccagcctgg caccagac ctacatctgc       660 aacgtgaacc acaagccctc caacaccaag gtggacaaga aggtggaacc caagtcctgc     720
gacaagaccc acacctgtcc ccctgccct gccctgaac tgctgggcgg accttccgtg       780
ttcctgttcc ccccaaagcc taaggacacc ctgatgatct cccggacccc cgaagtgacc    840
tgcgtggtgg tggacgtgtc ccacgaggac cctgaagtga agttcaattg gtacgtggac    900
ggcgtggaag tgcacaacgc caagaccaag cccagagagg aacagtacaa ctccacctac     960
cgggtggtgt ccgtgctgac cgtgctgcac caggactggc tgaacggcaa agagtacaag   1020
tgcaaggtgt ccaacaaggc cctgcctgcc cccatcgaaa agaccatctc caaggccaag   1080
ggccagcccc gcgagcccca ggtgtacacc ctgccccta gccgggacga gctgaccaag     1140
aaccaggtgt ccctgacctg tctggtgaaa ggcttctacc cctccgatat cgccgtggaa   1200
tgggagtcca acggccagcc cgagaacaac tacaagacca ccccccctgt gctggactcc   1260
gacggctcat tcttcctgta ctccaagctg acagtggata gtcccggtg cagcagggc    1320 aacgtgttct cctgctccgt gatgcacgag gccctgcaca accactacac ccagaagtcc   1380
ctgtccctga gccccggcaa g                                            1401
```

<210> SEQ ID NO 48
<211> LENGTH: 714
<212> TYPE: DNA
<213> ORGANISM: Artificial Sequence
<220> FEATURE:
<223> OTHER INFORMATION: CHO-optimized cDNA sequence coding for chimeric
      no. 32 human kappa chain

<400> SEQUENCE: 48

```
atggagtggt ccggcgtgtt catgttcctg ctgtccgtga ccgctggcgt gcactccgac     60
atccagatga cccagacccc cctgtccctg ccgtgtctc tgggcgacca ggcctccatc    120
tcctgccggt cctcccagtc catcgtgcac tccaacggca cacctacct ggaatggtat    180 ctgcagaagc ccggccagtc ccccaagctg ctgatctaca aggtgtccaa ccggttctcc    240
ggcgtgcccg acagattctc cggctccggc tctggcaccg acttcaccct gaagatctcc    300
cgggtggaag ccgaggacct gggcgtgtac tactgttttc agggctccca cgtgccctgg   360
accttcggcg aggcaccaa gctggaaatc aagcggaccg tggccgctcc ctccgtgttc     420
atcttcccac cctccgacga gcagctgaag tccggcaccg cctccgtggt gtgcctgctg    480
aacaacttct accccccgcga ggccaaggtg cagtggaagg tggacaacgc cctgcagtcc    540
ggcaactccc aggaatccgt caccgagcag gactccaagg acagcaccta ctccctgtcc    600
tccaccctga cctgtccaa ggcgactac gagaagcaca aggtgtacgc ctgcgaagtg      660
```

| | |
|---|---|
| acccaccagg gcctgtccag ccccgtgacc aagtccttca accggggcga gtgc | 714 |

<210> SEQ ID NO 49
<211> LENGTH: 1389
<212> TYPE: DNA
<213> ORGANISM: Artificial Sequence
<220> FEATURE:
<223> OTHER INFORMATION: chimeric no. 35 human IgG4 chain

<400> SEQUENCE: 49

| | |
|---|---|
| atggaatgga gcggcgtgtt catgttcctg ctgtccgtga ccgcgggagt gcacagtcag | 60 |
| gtccagctgc agcagtctgg ggcagagctt gtgaggtcag ggcctcagt caagttgtcc | 120 |
| tgcacagctt ctggcttcaa cattaaagac tactatatgc actgggtgaa gcagaggcct | 180 |
| gaacagggcc tggagtggat tggatggatt gatcctgaga atggtgatac tgaatatgcc | 240 |
| ccgaagttcc agggcaaggc cactatgact gcagacacgt cctccaacac agcctacctg | 300 |
| cagctcagca gcctgacatc tgaggacact gccgtctatt actgtaattg ggaaaaattc | 360 |
| tatgctatgg acgactgggg tcaaggaacc tcagtcaccg tctcctcagc tagcaccaag | 420 |
| ggccctccg tgtttcctct ggccccttgc tccagatcca cctccgagtc taccgccgct | 480 |
| ctgggctgcc tcgtgaagga ctacttcccc gagcccgtga cagtgtcttg aactctggc | 540 |
| gccctgacct ccggcgtgca cacatttcca gctgtgctgc agtcctccgg cctgtactcc | 600 |
| ctgtcctccg tcgtgactgt gccttcctct agcctgggca ccaagaccta cacctgtaac | 660 |
| gtggaccaca gcccctccaa caccaaggtg gacaagcggg tggaatctaa gtacggccct | 720 |
| ccttgcccac cctgccctgc cctgaatttt ctgggcggac cttccgtgtt cctgttccc | 780 |
| ccaaagccca aggacaccct gatgatctcc cggaccccg aagtgacctg cgtggtggtg | 840 |
| gatgtgtccc aggaagatcc cgaggtgcag ttcaattggt acgtggacgg cgtggaagtg | 900 |
| cacaacgcca agaccaagcc cagagaggaa cagttcaact ccacctaccg ggtggtgtcc | 960 |
| gtgctgaccg tgctgcacca ggattggctg aacggcaaag agtacaagtg caaggtgtcc | 1020 |
| aacaagggcc tgccctccag catcgaaaag accatctcca aggccaaggg ccagccccgg | 1080 |
| gaaccccagg tgtacacact gcctccaagc caggaagaga tgaccaagaa ccaggtgtcc | 1140 |
| ctgacctgtc tcgtgaaagg cttctacccc tccgatatcg ccgtggaatg ggagtccaac | 1200 |
| ggccagcctg agaacaacta caagaccacc cccctgtgc tggactccga cggctccttc | 1260 |
| ttcctgtact ctcgcctgac cgtggacaag tccggtggc aggaaggcaa cgtgttctcc | 1320 |
| tgctctgtga tgcacgaggc cctgcacaac cactacaccc agaagtccct gtccctgtct | 1380 |
| ctgggcaag | 1389 |

<210> SEQ ID NO 50
<211> LENGTH: 717
<212> TYPE: DNA
<213> ORGANISM: Artificial Sequence
<220> FEATURE:
<223> OTHER INFORMATION: chimeric no. 35 human kappa chain

<400> SEQUENCE: 50

| | |
|---|---|
| atggaatgga gcggcgtgtt catgttcctg ctgtccgtga ccgcgggagt gcacagcgac | 60 |
| attgtgatgt cacagtctcc atcctcccta gctgtgtcag ttggagagaa ggttactatg | 120 |
| agctgcaagt ccagtcagag ccttttatat agtagcaatc aaaagaacta cttggcctgg | 180 |
| taccagcaga accagggca gtctcctaaa ctactgattt actgggcatc cactagggaa | 240 |

```
tctgggtcc ctgatcgctt cacaggcagt ggatctggga cagatttcac tctcaccatc    300
agcagtgtga aggctgaaga cctggcagtt tattactgtc agcaatatta tagctatcct    360
cggacgttcg gtggaggcac aagctggaa atcaaacgga ccgtagccgc ccttccgtg    420 ttcatctttc caccctccga cgagcagctg aagtctggca ccgcttccgt cgtgtgcctg    480
ctgaacaact tctacccccg cgaggccaag gtgcagtgga aggtggacaa cgccctgcag    540
tccggcaact cccaggaaag cgtgaccgag caggactcca aggacagcac ctactccctg    600
tcctccaccc tgaccctgtc caaggccgac tacgagaagc acaaggtgta cgcctgcgaa    660
gtgacccacc agggcctgtc tagccccgtg accaagtctt tcaaccgggg cgagtgc       717

<210> SEQ ID NO 51
<211> LENGTH: 1410
<212> TYPE: DNA
<213> ORGANISM: Artificial Sequence
<220> FEATURE:
<223> OTHER INFORMATION: chimeric no. 60 human IgG4 chain

<400> SEQUENCE: 51
atggaatgga gcggcgtgtt catgttcctg ctgtccgtga ccgcgggagt gcacagccag    60
gtgcagctgc agcagtctgg ccctgggatt ttgcagccct cccagaccct cagtctgact    120
tgttctttct ctgggttttc actgagcacc tctaatatgg gtgtaggctg gattcgtcag    180
ccttcaggga agggtctgga gtggctggca cacatttggt gggatgatga caagcgctat    240
aatccagccc tgaagagccg actgacaatc tccaaggata cctccagcaa ccaggtattc    300
ctcaagatcg ccagtgtgga cactgcagat actgccacat acttctgtgc tcgaataggc    360
cgacctacta tgattacgac gtggtacctc gatgtctggg gcgcagggac cacggtcacc    420
gtctcctcag ctagcaccaa gggccccctcc gtgtttcctc tggccccttg ctccagatcc    480
acctccgagt ctaccgccgc tctgggctgc ctcgtgaagg actacttccc cgagcccgtg    540
acagtgtctt ggaactctgg cgccctgacc tccggcgtgc acacatttcc agctgtgctg    600
cagtcctccg gcctgtactc cctgtcctcc gtcgtgactg tgccttcctc tagcctgggc    660
accaagacct acacctgtaa cgtggaccac aagcccccca acaccaaggt ggacaagcgg    720
gtggaatcta agtacggccc tccttgccca ccctgccctg cccctgaatt tctgggcgga    780
ccttccgtgt tcctgtttcc cccaaagccc aaggacaccc tgatgatctc ccggacccccc    840 gaagtgacct gcgtggtggt ggatgtgtcc caggaagatc ccgaggtgca gttcaattgg    900
tacgtggacg gcgtggaagt gcacaacgcc aagaccaagc cagagagga acagttcaac    960 tccacctacc gggtggtgtc cgtgctgacc gtgctgcacc aggattggct gaacggcaaa    1020
gagtacaagt gcaaggtgtc caacaagggc ctgccctcca gcatcgaaaa gaccatctcc    1080
aaggccaagg ccagccccg ggaaccccag gtgtacacac tgcctccaag ccaggaagag    1140
atgaccaaga accaggtgtc cctgacctgt ctcgtgaaag gcttctaccc ctccgatatc    1200
gccgtggaat gggagtccaa cggccagcct gagaacaact acaagaccac ccccctgtg    1260 ctggactccg acggctcctt cttcctgtac tctcgcctga ccgtggacaa gtcccggtgg    1320
caggaaggca acgtgttctc ctgctctgtg atgcacgagg ccctgcacaa ccactacacc    1380
cagaagtccc tgtccctgtc tctgggcaag                                     1410

<210> SEQ ID NO 52
<211> LENGTH: 699
<212> TYPE: DNA
<213> ORGANISM: Artificial Sequence
```

<220> FEATURE:
<223> OTHER INFORMATION: chimeric no. 60 human kappa chain

<400> SEQUENCE: 52

```
atggaatgga gcggcgtgtt catgttcctg ctgtccgtga ccgcgggagt gcacagcgac      60
atccagatga ctcagtctcc agcctcccta tctgtatctg tgggagaaac tgtcaccatc     120
acatgtcgag caagtgagaa tatttacagt aatttagcat ggtatcagca gaaacaggga     180
aaatctcctc agctcctggt ctatgctgca acaaaattag cagatggtgt gccatcaagg     240
ttcagtggca gcggatcagg cacacagtat ccctcaaga tcaacagcct gcagtctgaa      300
gattttggga actattactg tcaacatttt tggaatactc cgtacacgtt cggaggggggg    360
accaagctgg aaataaaacg gaccgtagcc gccccttccg tgttcatctt ccaccctcc      420
gacgagcagc tgaagtctgg caccgcttcc gtcgtgtgcc tgctgaacaa cttctacccc     480
cgcgaggcca aggtgcagtg gaaggtggac aacgccctgc agtccggcaa ctcccaggaa     540
agcgtgaccg agcaggactc caaggacagc acctactccc tgtcctccac cctgaccctg     600
tccaaggccg actacgagaa gcacaaggtg tacgcctgcg aagtgaccca ccagggcctg     660
tctagccccg tgaccaagtc tttcaaccgg ggcgagtgc                            699
```

<210> SEQ ID NO 53
<211> LENGTH: 464
<212> TYPE: PRT
<213> ORGANISM: Artificial Sequence
<220> FEATURE:
<223> OTHER INFORMATION: chimeric no. 5F2.4 human IgG4 chain

<400> SEQUENCE: 53

```
Met Glu Trp Ser Gly Val Phe Met Phe Leu Leu Ser Val Thr Ala Gly
1               5                   10                  15

Val His Ser Glu Val Gln Leu Gln Gln Ser Gly Ala Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Met Asp Trp Val Lys Gln Ser His Gly Lys Ser Leu
    50                  55                  60

Glu Trp Ile Gly Asp Ile Asn Pro Asn Tyr Glu Ser Thr Gly Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Thr Ala Val
            100                 105                 110

Tyr Tyr Cys Ala Arg Glu Asp Asp His Asp Ala Phe Ala Tyr Trp Gly
        115                 120                 125

Gln Gly Thr Leu Val Thr Val Ser Ala Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Lys Thr Tyr Thr Cys Asn Val Asp His
```

```
            210                 215                 220
Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
                245                 250                 255

Val Phe Leu Phe Pro Pro Lys Pro Lys Asp Thr Leu Met Ile Ser Arg
                260                 265                 270

Thr Pro Glu Val Thr Cys Val Val Val Asp Val Ser Gln Glu Asp Pro
                275                 280                 285

Glu Val Gln Phe Asn Trp Tyr Val Asp Gly Val Glu Val His Asn Ala
            290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
                340                 345                 350

Ile Ser Lys Ala Lys Gly Gln Pro Arg Glu Pro Gln Val Tyr Thr Leu
            355                 360                 365

Pro Pro Ser Gln Glu Glu Met Thr Lys Asn Gln Val Ser Leu Thr Cys
                370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Arg Leu Thr Val Asp Lys Ser
                420                 425                 430

Arg Trp Gln Glu Gly Asn Val Phe Ser Cys Ser Val Met His Glu Ala
            435                 440                 445

Leu His Asn His Tyr Thr Gln Lys Ser Leu Ser Leu Ser Leu Gly Lys
                450                 455                 460

<210> SEQ ID NO 54
<211> LENGTH: 237
<212> TYPE: PRT
<213> ORGANISM: Artificial Sequence
<220> FEATURE:
<223> OTHER INFORMATION: chimeric no. 5F2.4 human kappa chain

<400> SEQUENCE: 54

Met Glu Trp Ser Gly Val Phe Met Phe Leu Leu Ser Val Thr Ala Gly
1               5                   10                  15

Val His Ser Asp Ile Val Leu Thr Gln Ser Pro Ala Ser Val Val Val
                20                  25                  30

Ser Leu Gly Gln Arg Ala Thr Ile Ser Cys Arg Ala Ser Lys Ser Val
            35                  40                  45

Arg Thr Ser Gly Tyr Asn Tyr Met His Trp Tyr Gln Gln Lys Pro Gly
        50                  55                  60

Gln Pro Pro Lys Leu Leu Ile Tyr Leu Ala Ser Asn Leu Lys Ser Gly
65                  70                  75                  80

Val Pro Ala Arg Phe Ser Gly Ser Gly Ser Gly Thr Asp Phe Thr Leu
                85                  90                  95

Asn Ile His Pro Val Glu Glu Ala Asp Ala Ala Thr Tyr Tyr Cys Gln
                100                 105                 110

His Ser Arg Glu Leu Pro Tyr Thr Phe Gly Gly Gly Thr Lys Leu Glu
```

```
                    115                 120                 125
Ile Lys Arg Thr Val Ala Ala Pro Ser Val Phe Ile Phe Pro Pro Ser
            130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
                195                 200                 205

Tyr Glu Lys His Lys Val Tyr Ala Cys Glu Val Thr His Gln Gly Leu
            210                 215                 220

Ser Ser Pro Val Thr Lys Ser Phe Asn Arg Gly Glu Cys
225                 230                 235

<210> SEQ ID NO 55
<211> LENGTH: 464
<212> TYPE: PRT
<213> ORGANISM: Artificial Sequence
<220> FEATURE:
<223> OTHER INFORMATION: chimeric no.13 human IgG4 chain

<400> SEQUENCE: 55

Met Glu Trp Ser Gly Val Phe Met Phe Leu Leu Ser Val Thr Ala Gly
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Thr Phe
        35                  40                  45

Thr Ile Tyr Tyr Met Tyr Trp Val Lys Gln Arg Pro Gly Gln Gly Leu
    50                  55                  60

Glu Trp Ile Gly Glu Val Asp Pro Ser Ile Gly Gly Ile Ser Phe Asn
65                  70                  75                  80

Glu Lys Phe Lys Ser Lys Ala Thr Leu Thr Val Asp Arg Ser Ser Ser
                85                  90                  95

Thr Ala Tyr Met His Leu Ser Ser Leu Thr Ser Glu Asp Ser Ala Val
            100                 105                 110

Tyr Tyr Cys Thr Arg Gly Gly Thr Tyr Tyr Ala Met Asp Tyr Trp Gly
        115                 120                 125

Gln Gly Thr Ser Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
```

```
                245                 250                 255
Val Phe Leu Phe Pro Pro Lys Pro Lys Asp Thr Leu Met Ile Ser Arg
            260                 265                 270

Thr Pro Glu Val Thr Cys Val Val Asp Val Ser Gln Glu Asp Pro
            275                 280                 285

Glu Val Gln Phe Asn Trp Tyr Val Asp Gly Val Glu Val His Asn Ala
            290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
                340                 345                 350

Ile Ser Lys Ala Lys Gly Gln Pro Arg Glu Pro Gln Val Tyr Thr Leu
                355                 360                 365

Pro Pro Ser Gln Glu Glu Met Thr Lys Asn Gln Val Ser Leu Thr Cys
            370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                    405                 410                 415

Ser Asp Gly Ser Phe Phe Leu Tyr Ser Arg Leu Thr Val Asp Lys Ser
                420                 425                 430

Arg Trp Gln Glu Gly Asn Val Phe Ser Cys Ser Val Met His Glu Ala
            435                 440                 445

Leu His Asn His Tyr Thr Gln Lys Ser Leu Ser Leu Ser Leu Gly Lys
            450                 455                 460

<210> SEQ ID NO 56
<211> LENGTH: 238
<212> TYPE: PRT
<213> ORGANISM: Artificial Sequence
<220> FEATURE:
<223> OTHER INFORMATION: chimeric no.13 human kappa chain

<400> SEQUENCE: 56

Met Glu Trp Ser Gly Val Phe Met Phe Leu Leu Ser Val Thr Ala Gly
1               5                   10                  15

Val His Ser Asp Val Leu Met Thr Gln Thr Pro Leu Ser Leu Pro Val
                20                  25                  30

Ser Leu Gly Asp Gln Ala Ser Ile Ser Cys Arg Ala Gly Gln Ser Ile
            35                  40                  45

Val His Ser Asn Gly Asn Thr Tyr Leu Glu Trp Tyr Leu Gln Lys Pro
        50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Trp Thr Phe Gly Gly Gly Thr Lys Leu
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
```

```
145                 150                 155                 160
Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
                180                 185                 190

Lys Asp Ser Thr Tyr Ser Leu Ser Ser Thr Leu Thr Leu Ser Lys Ala
                195                 200                 205

Asp Tyr Glu Lys His Lys Val Tyr Ala Cys Glu Val Thr His Gln Gly
            210                 215                 220

Leu Ser Ser Pro Val Thr Lys Ser Phe Asn Arg Gly Glu Cys
225                 230                 235

<210> SEQ ID NO 57
<211> LENGTH: 464
<212> TYPE: PRT
<213> ORGANISM: Artificial Sequence
<220> FEATURE:
<223> OTHER INFORMATION: chimeric no. 32 human IgG4 chain

<400> SEQUENCE: 57

Met Glu Trp Ser Gly Val Phe Met Phe Leu Leu Ser Val Thr Ala Gly
1               5                   10                  15

Val His Ser Gln Val Gln Leu Gln Gln Ser Gly Ala Glu Leu Val Lys
                20                  25                  30

Pro Gly Ala Ser Val Lys Leu Ser Cys Lys Ala Ser Gly Tyr Thr Phe
            35                  40                  45

Thr Ser Tyr Asp Met Tyr Trp Val Lys Gln Arg Pro Gly Gln Gly Leu
    50                  55                  60

Glu Trp Ile Gly Glu Ile Asn Pro Ser Asn Gly Asp Thr Asn Phe Asn
65                  70                  75                  80

Glu Lys Phe Lys Ser Lys Ala Thr Leu Thr Val Asp Lys Ser Ser Ser
                85                  90                  95

Thr Ala His Met Gln Leu Ser Ser Leu Thr Ser Glu Asp Ser Ala Val
                100                 105                 110

Tyr Tyr Cys Thr Arg Gly Gly Thr Phe Tyr Ala Met Asp Tyr Trp Gly
            115                 120                 125

Gln Gly Thr Ser Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
            195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
                245                 250                 255

Val Phe Leu Phe Pro Pro Lys Pro Lys Asp Thr Leu Met Ile Ser Arg
                260                 265                 270

Thr Pro Glu Val Thr Cys Val Val Val Asp Val Ser Gln Glu Asp Pro
```

```
                275                 280                 285
Glu Val Gln Phe Asn Trp Tyr Val Asp Gly Val Glu Val His Asn Ala
290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
            325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
            355                 360                 365

Pro Pro Ser Gln Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Arg Leu Thr Val Asp Lys Ser
            420                 425                 430

Arg Trp Gln Glu Gly Asn Val Phe Ser Cys Ser Val Met His Glu Ala
            435                 440                 445

Leu His Asn His Tyr Thr Gln Lys Ser Leu Ser Leu Ser Leu Gly Lys
            450                 455                 460

<210> SEQ ID NO 58
<211> LENGTH: 467
<212> TYPE: PRT
<213> ORGANISM: Artificial Sequence
<220> FEATURE:
<223> OTHER INFORMATION: chimeric no. 32 human IgG1 chain

<400> SEQUENCE: 58

Met Glu Trp Ser Gly Val Phe Met Phe Leu Leu Ser Val Thr Ala Gly
1               5                   10                  15

Val His Ser Gln Val Gln Leu Gln Gln Ser Gly Ala Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Asp Met Tyr Trp Val Lys Gln Arg Pro Gly Gln Gly Leu
    50                  55                  60

Glu Trp Ile Gly Glu Ile Asn Pro Ser Asn Gly Asp Thr Asn Phe Asn
65                  70                  75                  80

Glu Lys Phe Lys Ser Lys Ala Thr Leu Thr Val Asp Lys Ser Ser Ser
                85                  90                  95

Thr Ala His Met Gln Leu Ser Ser Leu Thr Ser Glu Asp Ser Ala Val
            100                 105                 110

Tyr Tyr Cys Thr Arg Gly Gly Thr Phe Tyr Ala Met Asp Tyr Trp Gly
        115                 120                 125

Gln Gly Thr Ser Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
```

```
              180                 185                 190
Val Leu Gln Ser Ser Gly Leu Tyr Ser Leu Ser Ser Val Val Thr Val
              195                 200                 205

Pro Ser Ser Ser Leu Gly Thr Gln Thr Tyr Ile Cys Asn Val Asn His
        210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 59
<211> LENGTH: 238
<212> TYPE: PRT
<213> ORGANISM: Artificial Sequence
<220> FEATURE:
<223> OTHER INFORMATION: chimeric no. 32 human kappa chain

<400> SEQUENCE: 59

Met Glu Trp Ser Gly Val Phe Met Phe Leu Leu Ser Val Thr Ala Gly
1               5                   10                  15

Val His Ser Asp Ile Gln Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
```

```
                65                  70                  75                  80
Gly Val Pro Asp Arg Phe Ser Gly Ser Gly Ser Gly Thr Asp Phe Thr
                        85                  90                  95

Leu Lys Ile Ser Arg Val Glu Ala Glu Asp Leu Gly Val Tyr Tyr Cys
                100                 105                 110

Phe Gln Gly Ser His Val Pro Trp Thr Phe Gly Gly Gly Thr Lys Leu
                115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
                180                 185                 190

Lys Asp Ser Thr Tyr Ser Leu Ser Ser Thr Leu Thr Leu Ser Lys Ala
                195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235
```

<210> SEQ ID NO 60
<211> LENGTH: 463
<212> TYPE: PRT
<213> ORGANISM: Artificial Sequence
<220> FEATURE:
<223> OTHER INFORMATION: chimeric no. 35 human IgG4 chain

<400> SEQUENCE: 60

```
Met Glu Trp Ser Gly Val Phe Met Phe Leu Leu Ser Val Thr Ala Gly
1               5                   10                  15

Val His Ser Gln Val Gln Leu Gln Gln Ser Gly Ala Glu Leu Val Arg
                20                  25                  30

Ser Gly Ala Ser Val Lys Leu Ser Cys Thr Ala Ser Gly Phe Asn Ile
            35                  40                  45

Lys Asp Tyr Tyr Met His Trp Val Lys Gln Arg Pro Glu Gln Gly Leu
    50                  55                  60

Glu Trp Ile Gly Trp Ile Asp Pro Glu Asn Gly Asp Thr Glu Tyr Ala
65                  70                  75                  80

Pro Lys Phe Gln Gly Lys Ala Thr Met Thr Ala Asp Thr Ser Ser Asn
                85                  90                  95

Thr Ala Tyr Leu Gln Leu Ser Ser Leu Thr Ser Glu Asp Thr Ala Val
                100                 105                 110

Tyr Tyr Cys Asn Trp Glu Lys Phe Tyr Ala Met Asp Asp Trp Gly Gln
                115                 120                 125

Gly Thr Ser Val Thr Val Ser Ser Ala Ser Thr Lys Gly Pro Ser Val
130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
                180                 185                 190

Leu Gln Ser Ser Gly Leu Tyr Ser Leu Ser Ser Val Val Thr Val Pro
```

```
            195                 200                 205
Ser Ser Ser Leu Gly Thr Lys Thr Tyr Thr Cys Asn Val Asp His Lys
    210                 215                 220

Pro Ser Asn Thr Lys Val Asp Lys Arg Val Glu Ser Lys Tyr Gly Pro
225                 230                 235                 240

Pro Cys Pro Pro Cys Pro Ala Pro Glu Phe Leu Gly Gly Pro Ser Val
            245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser Gln Glu Asp Pro Glu
            275                 280                 285

Val Gln Phe Asn Trp Tyr Val Asp Gly Val Glu Val His Asn Ala Lys
        290                 295                 300

Thr Lys Pro Arg Glu Glu Gln Phe Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Gly Leu Pro Ser Ser Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Gln Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Arg Leu Thr Val Asp Lys Ser Arg
            420                 425                 430

Trp Gln Glu Gly Asn Val Phe Ser Cys Ser Val Met His Glu Ala Leu
        435                 440                 445

His Asn His Tyr Thr Gln Lys Ser Leu Ser Leu Ser Leu Gly Lys
    450                 455                 460

<210> SEQ ID NO 61
<211> LENGTH: 239
<212> TYPE: PRT
<213> ORGANISM: Artificial Sequence
<220> FEATURE:
<223> OTHER INFORMATION: chimeric no. 35 human kappa chain

<400> SEQUENCE: 61

Met Glu Trp Ser Gly Val Phe Met Phe Leu Leu Ser Val Thr Ala Gly
1               5                   10                  15

Val His Ser Asp Ile Val Met Ser Gln Ser Pro Ser Ser Leu Ala Val
                20                  25                  30

Ser Val Gly Glu Lys Val Thr Met Ser Cys Lys Ser Ser Gln Ser Leu
            35                  40                  45

Leu Tyr Ser Ser Asn Gln Lys Asn Tyr Leu Ala Trp Tyr Gln Gln Lys
    50                  55                  60

Pro Gly Gln Ser Pro Lys Leu Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Ser Val Lys Ala Glu Asp Leu Ala Val Tyr Tyr
```

```
            100             105                 110
Cys Gln Gln Tyr Tyr Ser Tyr Pro Arg Thr Phe Gly Gly Gly Thr Lys
            115                 120                 125

Leu Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 62
<211> LENGTH: 470
<212> TYPE: PRT
<213> ORGANISM: Artificial Sequence
<220> FEATURE:
<223> OTHER INFORMATION: chimeric no. 60 human IgG4 chain

<400> SEQUENCE: 62

Met Glu Trp Ser Gly Val Phe Met Phe Leu Leu Ser Val Thr Ala Gly
1               5                   10                  15

Val His Ser Gln Val Gln Leu Gln Gln Ser Gly Pro Gly Ile Leu Gln
            20                  25                  30

Pro Ser Gln Thr Leu Ser Leu Thr Cys Ser Phe Ser Gly Phe Ser Leu
        35                  40                  45

Ser Thr Ser Asn Met Gly Val Gly Trp Ile Arg Gln Pro Ser Gly Lys
    50                  55                  60

Gly Leu Glu Trp Leu Ala His Ile Trp Trp Asp Asp Asp Lys Arg Tyr
65                  70                  75                  80

Asn Pro Ala Leu Lys Ser Arg Leu Thr Ile Ser Lys Asp Thr Ser Ser
                85                  90                  95

Asn Gln Val Phe Leu Lys Ile Ala Ser Val Asp Thr Ala Asp Thr Ala
            100                 105                 110

Thr Tyr Phe Cys Ala Arg Ile Gly Arg Pro Thr Met Ile Thr Thr Trp
        115                 120                 125

Tyr Leu Asp Val Trp Gly Ala Gly Thr Thr Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Lys Thr Tyr
    210                 215                 220

Thr Cys Asn Val Asp His Lys Pro Ser Asn Thr Lys Val Asp Lys Arg
```

```
                225                 230                 235                 240

Val Glu Ser Lys Tyr Gly Pro Pro Cys Pro Pro Cys Pro Ala Pro Glu
                        245                 250                 255

Phe Leu Gly Gly Pro Ser Val Phe Leu Phe Pro Pro Lys Pro Lys Asp
                        260                 265                 270

Thr Leu Met Ile Ser Arg Thr Pro Glu Val Thr Cys Val Val Val Asp
                        275                 280                 285

Val Ser Gln Glu Asp Pro Glu Val Gln Phe Asn Trp Tyr Val Asp Gly
                        290                 295                 300

Val Glu Val His Asn Ala Lys Thr Lys Pro Arg Glu Glu Gln Phe Asn
        305                 310                 315                 320

Ser Thr Tyr Arg Val Val Ser Val Leu Thr Val Leu His Gln Asp Trp
                        325                 330                 335

Leu Asn Gly Lys Glu Tyr Lys Cys Lys Val Ser Asn Lys Gly Leu Pro
                        340                 345                 350

Ser Ser Ile Glu Lys Thr Ile Ser Lys Ala Lys Gly Gln Pro Arg Glu
                        355                 360                 365

Pro Gln Val Tyr Thr Leu Pro Pro Ser Gln Glu Glu Met Thr Lys Asn
                        370                 375                 380

Gln Val Ser Leu Thr Cys Leu Val Lys Gly Phe Tyr Pro Ser Asp Ile
        385                 390                 395                 400

Ala Val Glu Trp Glu Ser Asn Gly Gln Pro Glu Asn Asn Tyr Lys Thr
                        405                 410                 415

Thr Pro Pro Val Leu Asp Ser Asp Gly Ser Phe Phe Leu Tyr Ser Arg
                        420                 425                 430

Leu Thr Val Asp Lys Ser Arg Trp Gln Glu Gly Asn Val Phe Ser Cys
                        435                 440                 445

Ser Val Met His Glu Ala Leu His Asn His Tyr Thr Gln Lys Ser Leu
                        450                 455                 460

Ser Leu Ser Leu Gly Lys
        465                 470

<210> SEQ ID NO 63
<211> LENGTH: 233
<212> TYPE: PRT
<213> ORGANISM: Artificial Sequence
<220> FEATURE:
<223> OTHER INFORMATION: chimeric no. 60 human kappa chain

<400> SEQUENCE: 63

Met Glu Trp Ser Gly Val Phe Met Phe Leu Leu Ser Val Thr Ala Gly
        1               5                   10                  15

Val His Ser Asp Ile Gln Met Thr Gln Ser Pro Ala Ser Leu Ser Val
                        20                  25                  30

Ser Val Gly Glu Thr Val Thr Ile Thr Cys Arg Ala Ser Glu Asn Ile
                        35                  40                  45

Tyr Ser Asn Leu Ala Trp Tyr Gln Gln Lys Gly Lys Ser Pro Gln
        50                  55                  60

Leu Leu Val Tyr Ala Ala Thr Lys Leu Ala Asp Gly Val Pro Ser Arg
        65                  70                  75                  80

Phe Ser Gly Ser Gly Ser Gly Thr Gln Tyr Ser Leu Lys Ile Asn Ser
                        85                  90                  95

Leu Gln Ser Glu Asp Phe Gly Asn Tyr Tyr Cys Gln His Phe Trp Asn
                        100                 105                 110

Thr Pro Tyr Thr Phe Gly Gly Gly Thr Lys Leu Glu Ile Lys Arg Thr
```

```
                115                 120                 125
Val Ala Ala Pro Ser Val Phe Ile Phe Pro Pro Ser Asp Glu Gln Leu
            130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 64
<211> LENGTH: 20
<212> TYPE: DNA
<213> ORGANISM: Artificial Sequence
<220> FEATURE:
<223> OTHER INFORMATION: primer

<400> SEQUENCE: 64
ctcttggttc caggttccac                                              20

<210> SEQ ID NO 65
<211> LENGTH: 25
<212> TYPE: DNA
<213> ORGANISM: Artificial Sequence
<220> FEATURE:
<223> OTHER INFORMATION: primer

<400> SEQUENCE: 65
acactcattc ctgttgaagc tcttg                                        25

<210> SEQ ID NO 66
<211> LENGTH: 23
<212> TYPE: DNA
<213> ORGANISM: Artificial Sequence
<220> FEATURE:
<223> OTHER INFORMATION: primer

<400> SEQUENCE: 66
saggtsmarc tgvagsagtc wgg                                          23

<210> SEQ ID NO 67
<211> LENGTH: 20
<212> TYPE: DNA
<213> ORGANISM: Artificial Sequence
<220> FEATURE:
<223> OTHER INFORMATION: primer

<400> SEQUENCE: 67
tggacaggga tccagagttc                                              20

<210> SEQ ID NO 68
<211> LENGTH: 23
<212> TYPE: DNA
<213> ORGANISM: Artificial Sequence
<220> FEATURE:
<223> OTHER INFORMATION: primer
<220> FEATURE:
```

```
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 68
gcgcttaaca caaacccncc nyt                                          23

<210> SEQ ID NO 69
<211> LENGTH: 24
<212> TYPE: DNA
<213> ORGANISM: Artificial Sequence
<220> FEATURE:
<223> OTHER INFORMATION: primer

<400> SEQUENCE: 69
aattttcttg tccacyttgg tgct                                         24

<210> SEQ ID NO 70
<211> LENGTH: 22
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (17)..(17)
<223> OTHER INFORMATION: n is a, c, g, or t

<400> SEQUENCE: 70
gcgatataca ratgacncar ac                                           22

<210> SEQ ID NO 71
<211> LENGTH: 20
<212> TYPE: DNA
<213> ORGANISM: Artificial Sequence
<220> FEATURE:
<223> OTHER INFORMATION: primer

<400> SEQUENCE: 71
gacagttggt gcagcatcag                                              20

<210> SEQ ID NO 72
<211> LENGTH: 40
<212> TYPE: DNA
<213> ORGANISM: Artificial Sequence
<220> FEATURE:
<223> OTHER INFORMATION: primer

<400> SEQUENCE: 72
ccgcgggagt gcacagcgac attgtgctga cacagtctcc                        40

<210> SEQ ID NO 73
<211> LENGTH: 23
<212> TYPE: DNA
<213> ORGANISM: Artificial Sequence
<220> FEATURE:
<223> OTHER INFORMATION: primer

<400> SEQUENCE: 73
cggtccgttt tatttccaac ttg                                          23

<210> SEQ ID NO 74
<211> LENGTH: 41
```

```
<212> TYPE: DNA
<213> ORGANISM: Artificial Sequence
<220> FEATURE:
<223> OTHER INFORMATION: primer

<400> SEQUENCE: 74
gccgcgggag tgcacagcga ggtgcagctg cagcagtctg g                 41

<210> SEQ ID NO 75
<211> LENGTH: 28
<212> TYPE: DNA
<213> ORGANISM: Artificial Sequence
<220> FEATURE:
<223> OTHER INFORMATION: primer

<400> SEQUENCE: 75
cgctagcagc agagacagtg accagagt                                28

<210> SEQ ID NO 76
<211> LENGTH: 50
<212> TYPE: DNA
<213> ORGANISM: Artificial Sequence
<220> FEATURE:
<223> OTHER INFORMATION: primer

<400> SEQUENCE: 76
ccgcgggagt gcacagcgat gtcctcatga cacaaacgcc tctctccctg        50

<210> SEQ ID NO 77
<211> LENGTH: 23
<212> TYPE: DNA
<213> ORGANISM: Artificial Sequence
<220> FEATURE:
<223> OTHER INFORMATION: primer

<400> SEQUENCE: 77
cggtccgttt gatttccagc ttg                                     23

<210> SEQ ID NO 78
<211> LENGTH: 40
<212> TYPE: DNA
<213> ORGANISM: Artificial Sequence
<220> FEATURE:
<223> OTHER INFORMATION: primer

<400> SEQUENCE: 78
ccgcgggagt gcacagtcag gtccaactgc agcagcctgg                   40

<210> SEQ ID NO 79
<211> LENGTH: 23
<212> TYPE: DNA
<213> ORGANISM: Artificial Sequence
<220> FEATURE:
<223> OTHER INFORMATION: primer

<400> SEQUENCE: 79
gctagctgag gagacggtga ctg                                     23

<210> SEQ ID NO 80
<211> LENGTH: 39
<212> TYPE: DNA
<213> ORGANISM: Artificial Sequence
<220> FEATURE:
<223> OTHER INFORMATION: primer

<400> SEQUENCE: 80
```
ccgcgggagt gcacagtcag gtgcagctgc agcagtctg          39

<210> SEQ ID NO 81
<211> LENGTH: 23
<212> TYPE: DNA
<213> ORGANISM: Artificial Sequence
<220> FEATURE:
<223> OTHER INFORMATION: primer

<400> SEQUENCE: 81
gctagcagag gacacggtca cgg          23

<210> SEQ ID NO 82
<211> LENGTH: 40
<212> TYPE: DNA
<213> ORGANISM: Artificial Sequence
<220> FEATURE:
<223> OTHER INFORMATION: primer

<400> SEQUENCE: 82
ccgcgggagt gcacagcgac attgtgatgt cacagtctcc          40

<210> SEQ ID NO 83
<211> LENGTH: 40
<212> TYPE: DNA
<213> ORGANISM: Artificial Sequence
<220> FEATURE:
<223> OTHER INFORMATION: primer

<400> SEQUENCE: 83
ccgcgggagt gcacagtcag gtccagctgc agcagtctgg          40

<210> SEQ ID NO 84
<211> LENGTH: 40
<212> TYPE: DNA
<213> ORGANISM: Artificial Sequence
<220> FEATURE:
<223> OTHER INFORMATION: primer

<400> SEQUENCE: 84
ccgcgggagt gcacagcgac atccagatga ctcagtctcc          40

<210> SEQ ID NO 85
<211> LENGTH: 46
<212> TYPE: DNA
<213> ORGANISM: Artificial Sequence
<220> FEATURE:
<223> OTHER INFORMATION: primer

<400> SEQUENCE: 85
ccgcgggagt gcacagccag gtgcagctgc agcagtctgg ccctgg          46

<210> SEQ ID NO 86
<211> LENGTH: 26
<212> TYPE: DNA
<213> ORGANISM: Artificial Sequence
<220> FEATURE:
<223> OTHER INFORMATION: primer

<400> SEQUENCE: 86
gctagctgag gagacggtga ccgtgg          26

<210> SEQ ID NO 87
<211> LENGTH: 28
<212> TYPE: DNA
<213> ORGANISM: Artificial Sequence

```
<220> FEATURE:
<223> OTHER INFORMATION: primer

<400> SEQUENCE: 87
atggaagccc cagctcagct tctcttcc                                          28

<210> SEQ ID NO 88
<211> LENGTH: 20
<212> TYPE: DNA
<213> ORGANISM: Artificial Sequence
<220> FEATURE:
<223> OTHER INFORMATION: primer

<400> SEQUENCE: 88
actggatggt gggaagatgg                                                   20

<210> SEQ ID NO 89
<211> LENGTH: 26
<212> TYPE: DNA
<213> ORGANISM: Artificial Sequence
<220> FEATURE:
<223> OTHER INFORMATION: primer

<400> SEQUENCE: 89
atggratgga gckgggtctt tmtctt                                            26

<210> SEQ ID NO 90
<211> LENGTH: 21
<212> TYPE: DNA
<213> ORGANISM: Artificial Sequence
<220> FEATURE:
<223> OTHER INFORMATION: primer

<400> SEQUENCE: 90
cagtggatag accgatgggg g                                                 21

<210> SEQ ID NO 91
<211> LENGTH: 24
<212> TYPE: DNA
<213> ORGANISM: Artificial Sequence
<220> FEATURE:
<223> OTHER INFORMATION: primer

<400> SEQUENCE: 91
atgggcwtca aagatggagt caca                                              24

<210> SEQ ID NO 92
<211> LENGTH: 27
<212> TYPE: DNA
<213> ORGANISM: Artificial Sequence
<220> FEATURE:
<223> OTHER INFORMATION: primer

<400> SEQUENCE: 92
atgaaatgca gctggggcat sttcttc                                           27

<210> SEQ ID NO 93
<211> LENGTH: 21
<212> TYPE: DNA
<213> ORGANISM: Artificial Sequence
<220> FEATURE:
<223> OTHER INFORMATION: primer

<400> SEQUENCE: 93
cagtggatag acagatgggg g                                                 21
```

<210> SEQ ID NO 94
<211> LENGTH: 30
<212> TYPE: DNA
<213> ORGANISM: Artificial Sequence
<220> FEATURE:
<223> OTHER INFORMATION: primer

<400> SEQUENCE: 94
atgaagttgc ctgttaggct gttggtgctg                                    30

<210> SEQ ID NO 95
<211> LENGTH: 27
<212> TYPE: DNA
<213> ORGANISM: Artificial Sequence
<220> FEATURE:
<223> OTHER INFORMATION: primer

<400> SEQUENCE: 95
atgggcagac ttacattctc attcctg                                       27

<210> SEQ ID NO 96
<211> LENGTH: 112
<212> TYPE: PRT
<213> ORGANISM: Artificial Sequence
<220> FEATURE:
<223> OTHER INFORMATION: Consensus mouse amino acid sequence of no.
      5F2.4 light chain variable region

<400> SEQUENCE: 96

Asp Asn Val Leu Thr Gln Ser Pro Ala Ser Val Val Ser Leu Gly
1               5                   10                  15

Gln Arg Ala Thr Ile Ser Cys Arg Ala Ser Lys Ser Val Arg Thr Ser
            20                  25                  30

Gly Tyr Asn Tyr Met His Trp Tyr Gln Gln Lys Pro Gly Gln Pro Pro
        35                  40                  45

Lys Leu Leu Ile Tyr Leu Ala Ser Asn Leu Lys Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Ala Asp Ala Ala Thr Tyr Tyr Cys Gln His Ser Arg
                85                  90                  95

Glu Leu Pro Tyr Thr Phe Gly Gly Gly Thr Lys Leu Glu Ile Lys Arg
            100                 105                 110

<210> SEQ ID NO 97
<211> LENGTH: 117
<212> TYPE: PRT
<213> ORGANISM: Artificial Sequence
<220> FEATURE:
<223> OTHER INFORMATION: Consensus mouse amino acid sequence of no. 35
      heavy chain variable region

<400> SEQUENCE: 97

Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

```
Gln Gly Lys Ala Thr Met Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Asn Glu Trp Lys Phe Tyr Ala Met Asp Asp Trp Gly Gln Gly Thr Ser
            100                 105                 110

Val Thr Val Ser Ser
            115

<210> SEQ ID NO 98
<211> LENGTH: 124
<212> TYPE: PRT
<213> ORGANISM: Artificial Sequence
<220> FEATURE:
<223> OTHER INFORMATION: Consensus mouse amino acid sequence of no. 60
      heavy chain variable region

<400> SEQUENCE: 98

Gln Val Ala Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Asn Met Gly Val Gly Trp Ile Arg Gln Pro Ser Gly Lys Gly Leu Glu
        35                  40                  45

Trp Leu Ala His Ile Trp Trp Asp Asp Lys Arg Tyr Asn Pro Ala
 50                  55                  60

Leu Lys Ser Arg Leu Thr Ile Ser Lys Asp Thr Ser Ser Asn Gln Val
 65                  70                  75                  80

Phe Leu Lys Ile Ala Ser Val Asp Thr Ala Asp Thr Ala Thr Tyr Phe
                 85                  90                  95

Cys Ala Arg Ile Gly Arg Pro Thr Met Ile Thr Thr Trp Tyr Leu Asp
            100                 105                 110

Val Trp Gly Ala Gly Thr Thr Val Thr Val Ser Ser
            115                 120

<210> SEQ ID NO 99
<211> LENGTH: 111
<212> TYPE: PRT
<213> ORGANISM: Artificial Sequence
<220> FEATURE:
<223> OTHER INFORMATION: humanized light chain variable region VL1 anti-
      C2-5F2.4

<400> SEQUENCE: 99

Asp Asn Val Leu Thr Gln Ser Pro Asp Ser Leu Val Val Ser Leu Gly
1               5                   10                  15

Glu Arg Ala Thr Ile Ser Cys Arg Ala Ser Lys Ser Val Arg Thr Ser
            20                  25                  30

Gly Tyr Asn Tyr Met His Trp Tyr Gln Gln Lys Pro Gly Gln Pro Pro
        35                  40                  45

Lys Leu Leu Ile Tyr Leu Ala Ser Asn Leu Lys Ser Gly Val Pro Ala
 50                  55                  60

Arg Phe Ser Gly Ser Gly Ser Gly Thr Asp Phe Thr Leu Thr Ile Ser
 65                  70                  75                  80

Ser Leu Gln Glu Glu Asp Ala Ala Thr Tyr Tyr Cys Gln His Ser Arg
                 85                  90                  95

Glu Leu Pro Tyr Thr Phe Gly Gln Gly Thr Lys Leu Glu Ile Lys
            100                 105                 110
```

<210> SEQ ID NO 100
<211> LENGTH: 111
<212> TYPE: PRT
<213> ORGANISM: Artificial Sequence
<220> FEATURE:
<223> OTHER INFORMATION: humanized light chain variable region VL2 anti-
      C2-5F2.4

<400> SEQUENCE: 100

```
Asp Asn Val Leu Thr Gln Ser Pro Asp Ser Leu Ala Val Ser Leu Gly
1               5                   10                  15

Glu Arg Ala Thr Ile Ser Cys Arg Ala Ser Lys Ser Val Arg Thr Ser
            20                  25                  30

Gly Tyr Asn Tyr Met His Trp Tyr Gln Gln Lys Pro Gly Gln Pro Pro
        35                  40                  45

Lys Leu Leu Ile Tyr Leu Ala Ser Asn Leu Lys Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Gln Ala Glu Asp Ala Ala Thr Tyr Tyr Cys Gln His Ser Arg
                85                  90                  95

Glu Leu Pro Tyr Thr Phe Gly Gln Gly Thr Lys Leu Glu Ile Lys
            100                 105                 110
```

<210> SEQ ID NO 101
<211> LENGTH: 111
<212> TYPE: PRT
<213> ORGANISM: Artificial Sequence
<220> FEATURE:
<223> OTHER INFORMATION: humanized light chain variable region VL3 anti-
      C2-5F2.4

<400> SEQUENCE: 101

```
Asp Asn Val Leu Thr Gln Ser Pro Asp Ser Leu Ala Val Ser Leu Gly
1               5                   10                  15

Glu Arg Ala Thr Ile Ser Cys Arg Ala Ser Lys Ser Val Arg Thr Ser
            20                  25                  30

Gly Tyr Asn Tyr Met His Trp Tyr Gln Gln Lys Pro Gly Gln Pro Pro
        35                  40                  45

Lys Leu Leu Ile Tyr Leu Ala Ser Asn Leu Lys Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Ala Ala Thr Tyr Tyr Cys Gln His Ser Arg
                85                  90                  95

Glu Leu Pro Tyr Thr Phe Gly Gln Gly Thr Lys Leu Glu Ile Lys
            100                 105                 110
```

<210> SEQ ID NO 102
<211> LENGTH: 111
<212> TYPE: PRT
<213> ORGANISM: Artificial Sequence
<220> FEATURE:
<223> OTHER INFORMATION: humanized light chain variable region VL4 anti-
      C2-5F2.4

<400> SEQUENCE: 102

```
Asp Asn Val Leu Thr Gln Ser Pro Asp Ser Leu Ala Val Ser Leu Gly
1               5                   10                  15

Glu Arg Ala Thr Ile Asn Cys Arg Ala Ser Lys Ser Val Arg Thr Ser
```

```
                    20                  25                  30

Gly Tyr Asn Tyr Met His Trp Tyr Gln Gln Lys Pro Gly Gln Pro Pro
                35                  40                  45

Lys Leu Leu Ile Tyr Leu Ala Ser Asn Leu Lys Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Ala Ala Thr Tyr Tyr Cys Gln His Ser Arg
                85                  90                  95

Glu Leu Pro Tyr Thr Phe Gly Gln Gly Thr Lys Leu Glu Ile Lys
                100                 105                 110

<210> SEQ ID NO 103
<211> LENGTH: 118
<212> TYPE: PRT
<213> ORGANISM: Artificial Sequence
<220> FEATURE:
<223> OTHER INFORMATION: humanized heavy chain variable region VH1 anti-
      C2-5F2.4

<400> SEQUENCE: 103

Glu Val Gln Leu Val Gln Ser Gly Ala Glu Leu Lys Lys Pro Gly Ala
 1               5                  10                  15

Ser Val Lys Ile Ser Cys Lys Ala Ser Gly Tyr Thr Phe Thr Asp Tyr
                20                  25                  30

Asn Met Asp Trp Val Lys Gln Ala His Gly Gln Gly Leu Glu Trp Ile
                35                  40                  45

Gly Asp Ile Asn Pro Asn Tyr Glu Ser Thr Gly Tyr Asn Gln Lys Phe
 50                  55                  60

Lys Gly Arg Ala Thr Leu Thr Val Asp Lys Ser Ile Ser Thr Ala Tyr
 65                  70                  75                  80

Met Glu Leu Arg Ser Leu Thr Ser Glu Asp Thr Ala Val Tyr Tyr Cys
                85                  90                  95

Ala Arg Glu Asp Asp His Asp Ala Phe Ala Tyr Trp Gly Gln Gly Thr
                100                 105                 110

Leu Val Thr Val Ser Ser
                115

<210> SEQ ID NO 104
<211> LENGTH: 118
<212> TYPE: PRT
<213> ORGANISM: Artificial Sequence
<220> FEATURE:
<223> OTHER INFORMATION: humanized heavy chain variable region VH2 anti-
      C2-5F2.4

<400> SEQUENCE: 104

Glu Val Gln Leu Val Gln Ser Gly Ala Glu Val Lys Lys Pro Gly Ala
 1               5                  10                  15

Ser Val Lys Ile Ser Cys Lys Ala Ser Gly Tyr Thr Phe Thr Asp Tyr
                20                  25                  30

Asn Met Asp Trp Val Lys Gln Ala Thr Gly Gln Gly Leu Glu Trp Ile
                35                  40                  45

Gly Asp Ile Asn Pro Asn Tyr Glu Ser Thr Gly Tyr Asn Gln Lys Phe
 50                  55                  60

Lys Gly Arg Ala Thr Leu Thr Val Asp Lys Ser Ile Ser Thr Ala Tyr
 65                  70                  75                  80

Met Glu Leu Ser Ser Leu Arg Ser Glu Asp Thr Ala Val Tyr Tyr Cys
```

```
                    85                  90                  95

Ala Arg Glu Asp Asp His Asp Ala Phe Ala Tyr Trp Gly Gln Gly Thr
                100                 105                 110

Leu Val Thr Val Ser Ser
        115

<210> SEQ ID NO 105
<211> LENGTH: 118
<212> TYPE: PRT
<213> ORGANISM: Artificial Sequence
<220> FEATURE:
<223> OTHER INFORMATION: humanized heavy chain variable region VH3 anti-
      C2-5F2.4

<400> SEQUENCE: 105

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
                20                  25                  30

Asn Met Asp Trp Val Arg Gln Ala Thr Gly Gln Gly Leu Glu Trp Ile
            35                  40                  45

Gly Asp Ile Asn Pro Asn Tyr Glu Ser Thr Gly Tyr Asn Gln Lys Phe
    50                  55                  60

Lys Gly Arg Ala Thr Leu Thr Val Asn Lys Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Asp His Asp Ala Phe Ala Tyr Trp Gly Gln Gly Thr
                100                 105                 110

Leu Val Thr Val Ser Ser
        115

<210> SEQ ID NO 106
<211> LENGTH: 118
<212> TYPE: PRT
<213> ORGANISM: Artificial Sequence
<220> FEATURE:
<223> OTHER INFORMATION: humanized heavy chain variable region VH4 anti-
      C2-5F2.4

<400> SEQUENCE: 106

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Asn Met Asp Trp Val Arg Gln Ala Thr Gly Gln Gly Leu Glu Trp Ile
            35                  40                  45

Gly Asp Ile Asn Pro Asn Tyr Glu Ser Thr Gly Tyr Asn Gln Lys Phe
    50                  55                  60

Lys Gly Arg Ala Thr Met Thr Val Asn Lys Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Asp His Asp Ala Phe Ala Tyr Trp Gly Gln Gly Thr
                100                 105                 110

Leu Val Thr Val Ser Ser
        115
```

<210> SEQ ID NO 107
<211> LENGTH: 654
<212> TYPE: DNA
<213> ORGANISM: Artificial Sequence
<220> FEATURE:
<223> OTHER INFORMATION: humanized light chain 5F2.4 containing humanized VL1

<400> SEQUENCE: 107

```
gacaacgtgc tgacccagtc ccctgactcc ctggtggtgt ctctgggcga gagagccacc      60
atctcttgcc gggcctctaa gtccgtgcgg acctccggct acaactacat gcactggtat     120
cagcagaagc ccggccagcc ccccaagctg ctgatctacc tggcctccaa cctgaagtcc     180
ggcgtgcccg ccagattctc cggctctggc tctggcaccg actttaccct gaccatcagc     240
tccctgcagg aagaggacgc cgccacctac tactgccagc actccagaga gctgccctac     300
acctttggcc agggcaccaa gctggaaatc aagcggaccg tggccgctcc ctccgtgttc     360
atcttcccac cttccgacga gcagctgaag tctggcacag cctccgtcgt gtgcctgctg     420
aacaacttct accccgcga ggccaaggtg cagtggaagg tggacaacgc cctgcagtcc     480
ggcaactccc aggaatccgt gaccgagcag gactccaagg acagcaccta ctccctgtcc     540
tccaccctga ccctgtccaa ggccgactac gagaagcaca aggtgtacgc ctgcgaagtg     600
acccaccagg gcctgtctag ccccgtgacc aagtctttca accggggcga gtgc          654
```

<210> SEQ ID NO 108
<211> LENGTH: 654
<212> TYPE: DNA
<213> ORGANISM: Artificial Sequence
<220> FEATURE:
<223> OTHER INFORMATION: humanized light chain 5F2.4 containing humanized VL2

<400> SEQUENCE: 108

```
gacaacgtgc tgacccagtc ccctgactcc ctggctgtgt ctctgggcga gagagccacc      60
atctcttgcc gggcctctaa gtccgtgcgg acctccggct acaactacat gcactggtat     120
cagcagaagc ccggccagcc ccccaagctg ctgatctacc tggcctccaa cctgaagtcc     180
ggcgtgcccg ccagattctc cggctctggc tctggcaccg actttaccct gaccatcagc     240
tccctgcagg ccgaggatgc cgccacctac tactgccagc actccagaga gctgccctac     300
acctttggcc agggcaccaa gctggaaatc aagcggaccg tggccgctcc ctccgtgttc     360
atcttcccac cttccgacga gcagctgaag tctggcacag cctccgtcgt gtgcctgctg     420
aacaacttct accccgcga ggccaaggtg cagtggaagg tggacaacgc cctgcagtcc     480
ggcaactccc aggaatccgt gaccgagcag gactccaagg acagcaccta ctccctgtcc     540
tccaccctga ccctgtccaa ggccgactac gagaagcaca aggtgtacgc ctgcgaagtg     600
acccaccagg gcctgtctag ccccgtgacc aagtctttca accggggcga gtgc          654
```

<210> SEQ ID NO 109
<211> LENGTH: 654
<212> TYPE: DNA
<213> ORGANISM: Artificial Sequence
<220> FEATURE:
<223> OTHER INFORMATION: humanized light chain 5F2.4 containing humanized VL3

<400> SEQUENCE: 109

```
gacaacgtgc tgacccagtc ccctgactcc ctggctgtgt ctctgggcga gagagccacc      60
atctcttgcc gggcctctaa gtccgtgcgg acctccggct acaactacat gcactggtat     120
```

```
cagcagaagc ccggccagcc ccccaagctg ctgatctacc tggcctccaa cctgaagtcc       180
ggcgtgcccg acagattctc cggctctggc tctggcaccg actttaccct gaccatcagc       240
tccctgcagg ccgaggatgc cgccacctac tactgccagc actccagaga gctgccctac       300
acctttggcc agggcaccaa gctggaaatc aagcggaccg tggccgctcc ctccgtgttc       360
atcttcccac cttccgacga gcagctgaag tctggcacag cctccgtcgt gtgcctgctg       420
aacaacttct accccccgcga ggccaaggtg cagtggaagg tggacaacgc cctgcagtcc      480
ggcaactccc aggaatccgt gaccgagcag gactccaagg acagcaccta ctccctgtcc       540
tccaccctga ccctgtccaa ggccgactac gagaagcaca aggtgtacgc ctgcgaagtg       600
acccaccagg gcctgtctag ccccgtgacc aagtctttca accggggcga gtgc             654
```

<210> SEQ ID NO 110
<211> LENGTH: 654
<212> TYPE: DNA
<213> ORGANISM: Artificial Sequence
<220> FEATURE:
<223> OTHER INFORMATION: humanized light chain 5F2.4 containing
      humanized VL4

<400> SEQUENCE: 110

```
gacaacgtgc tgacccagtc ccctgactcc ctggctgtgt ctctgggcga gagagccacc       60
atcaactgcc gggcctctaa gtccgtgcgg acctccggct acaactacat gcactggtat       120
cagcagaagc ccggccagcc ccccaagctg ctgatctacc tggcctccaa cctgaagtcc       180
ggcgtgcccg acagattctc cggctctggc tctggcaccg actttaccct gaccatcagc       240
tccctgcagg ccgaggatgc cgccacctac tactgccagc actccagaga gctgccctac       300
acctttggcc agggcaccaa gctggaaatc aagcggaccg tggccgctcc ctccgtgttc       360
atcttcccac cttccgacga gcagctgaag tctggcacag cctccgtcgt gtgcctgctg       420
aacaacttct accccccgcga ggccaaggtg cagtggaagg tggacaacgc cctgcagtcc      480
ggcaactccc aggaatccgt gaccgagcag gactccaagg acagcaccta ctccctgtcc       540
tccaccctga ccctgtccaa ggccgactac gagaagcaca aggtgtacgc ctgcgaagtg       600
acccaccagg gcctgtctag ccccgtgacc aagtctttca accggggcga gtgc             654
```

<210> SEQ ID NO 111
<211> LENGTH: 1335
<212> TYPE: DNA
<213> ORGANISM: Artificial Sequence
<220> FEATURE:
<223> OTHER INFORMATION: humanized IgG4 chain 5F2.4 containing humanized
      VH1

<400> SEQUENCE: 111

```
gaagtgcagc tggtgcagtc tggcgccgag ctgaagaaac ctggcgcctc cgtgaagatc       60
tcctgcaagg cctccggcta caccttcacc gactacaaca tggactgggt caagcaggcc       120
cacggccagg gcctggaatg gatcggcgac atcaaccccca actacgagtc caccggctac       180
aaccagaagt tcaagggcag agccacccctg accgtggaca gtccatctc caccgcctac       240 atggaactgc ggtccctgac ctctgaggac accgccgtgt actactgcgc cagagaggac       300
gaccacgacg cctttgctta ttggggccag ggcaccctcg tgaccgtgtc ctctgcttct       360
accaagggcc cctccgtgtt ccctctggcc ccttgctcca gatccaccctc cgagtctacc       420 gccgctctgg gctgcctcgt gaaggactac ttccccgagc ccgtgacagt gtcttggaac       480
```

```
tctggcgctc tgacctccgg cgtgcacacc tttccagctg tgctgcagtc ctccggcctg    540
tactccctgt cctccgtcgt gactgtgccc tccagctctc tgggcaccaa gacctacacc    600
tgtaacgtgg accacaagcc ctccaacacc aaggtggaca agcgggtgga atctaagtac    660
ggccctccct gccctccttg cccagcccct gaatttctgg gcggacccag cgtgttcctg    720
ttccccccaa agcccaagga caccctgatg atctcccgga ccccgaagt gacctgcgtg     780 gtggtggatg tgtcccagga agatcccgag gtgcagttca attggtacgt ggacggcgtg    840
gaagtgcaca acgccaagac caagcctaga gaggaacagt tcaactccac ctaccgggtg    900
gtgtccgtgc tgaccgtgct gcaccaggat tggctgaacg gcaaagagta caagtgcaag    960
gtgtccaaca agggcctgcc ttccagcatc gaaaagacca tctccaaggc caagggccag   1020
ccccgggaac cccaggtgta cacactgcct ccaagccagg aagagatgac caagaaccag   1080
gtgtccctga catgcctcgt gaaaggcttc taccctccg atatcgccgt ggaatgggag    1140
tccaacggcc agcctgagaa caactacaag accacccccc ctgtgctgga ctccgacggc   1200
tccttcttcc tgtactctcg gctgacagtg gataagagcc ggtggcagga aggcaacgtg   1260
ttctcctgct ccgtgatgca cgaggccctg cacaaccact atacccagaa gtccctgtcc   1320
ctgagcctgg gcaag                                                    1335
```

<210> SEQ ID NO 112
<211> LENGTH: 1335
<212> TYPE: DNA
<213> ORGANISM: Artificial Sequence
<220> FEATURE:
<223> OTHER INFORMATION: humanized IgG4 chain 5F2.4 containing humanized
      VH2

<400> SEQUENCE: 112

```
gaagtgcagc tggtgcagtc tggcgccgaa gtgaagaaac ctggcgcctc cgtgaagatc     60
tcctgcaagg cctccggcta caccttcacc gactacaaca tggactgggt caagcaggcc    120
accggccagg gcctggaatg gatcggcgac atcaaccca actacgagtc caccggctac     180
aaccagaagt tcaagggcag agccaccctg accgtggaca gtccatctc caccgcctac    240 atggaactgt cctccctgcg gagcgaggac accgccgtgt actactgcgc cagagaggac    300
gaccacgacg cctttgctta ttggggccag ggcaccctcg tgaccgtgtc ctctgcttct    360
accaagggcc cctccgtgtt ccctctggcc ccttgctcca gatccacctc cgagtctacc    420
gccgctctgg gctgcctcgt gaaggactac ttccccgagc ccgtgacagt gtcttggaac    480
tctggcgccc tgacctccgg cgtgcacacc tttccagctg tgctgcagtc ctccggcctg    540
tactccctgt cctccgtcgt gactgtgccc tccagctctc tgggcaccaa gacctacacc    600
tgtaacgtgg accacaagcc ctccaacacc aaggtggaca agcgggtgga atctaagtac    660
ggccctccct gccctccttg cccagcccct gaatttctgg gcggacccag cgtgttcctg    720
ttccccccaa agcccaagga caccctgatg atctcccgga ccccgaagt gacctgcgtg     780 gtggtggatg tgtcccagga agatcccgag gtgcagttca attggtacgt ggacggcgtg    840
gaagtgcaca acgccaagac caagcctaga gaggaacagt tcaactccac ctaccgggtg    900
gtgtccgtgc tgaccgtgct gcaccaggat tggctgaacg gcaaagagta caagtgcaag    960
gtgtccaaca agggcctgcc ttccagcatc gaaaagacca tctccaaggc caagggccag   1020
ccccgggaac cccaggtgta cacactgcct ccaagccagg aagagatgac caagaaccag   1080
gtgtccctga cctgtctcgt gaaaggcttc taccctccg atatcgccgt ggaatgggag    1140
```

```
tccaacggcc agcctgagaa caactacaag accacccccc ctgtgctgga ctccgacggc      1200
tccttcttcc tgtactctcg gctgacagtg gataagagcc ggtggcagga aggcaacgtg      1260
ttctcctgct ccgtgatgca cgaggccctg cacaaccact atacccagaa gtccctgtcc      1320
ctgtctctgg gaaag                                                      1335

<210> SEQ ID NO 113
<211> LENGTH: 1335
<212> TYPE: DNA
<213> ORGANISM: Artificial Sequence
<220> FEATURE:
<223> OTHER INFORMATION: humanized IgG4 chain 5F2.4 containing humanized
      VH3

<400> SEQUENCE: 113
gaagtgcagc tggtgcagtc tggcgccgaa gtgaagaaac tggcgcctc cgtgaagatc       60 tcctgcaagg cctccggcta caccttcacc gactacaaca tggactgggt gcgacaggct     120
accggccagg cctggaatg gatcggcgac atcaaccca actacgagtc caccggctac       180
aaccagaagt tcaagggcag agccaccctg accgtgaaca gtccatctc caccgcctac     240 atggaactgt cctccctgcg gagcgaggac accgccgtgt actactgcgc cagagaggac     300
gaccacgacg cctttgctta ttggggccag ggcaccctcg tgaccgtgtc ctctgcttct     360
accaagggcc cctccgtgtt ccctctggcc ccttgctcca gatccacctc cgagtctacc     420
gccgctctgg gctgcctcgt gaaggactac ttccccgagc ccgtgacagt gtcttggaac     480
tctggcgccc tgacctccgg cgtgcacacc tttccagctg tgctgcagtc ctccggcctg     540
tactccctgt cctccgtcgt gactgtgccc tccagctctc tgggcaccaa gacctacacc     600
tgtaacgtgg accacaagcc ctccaacacc aaggtggaca gcggtgga atctaagtac      660 ggccctccct gcctccttg cccagccct gaatttctgg gcggaccag cgtgttcctg        720 ttcccccca agcccaagga caccctgatg atctcccga ccccgaagt gacctgcgtg       780 gtggtggatg tgtcccagga agatcccga ggtgcagttca ttggtacgt ggacggcgtg     840 gaagtgcaca cgccaagac caagcctaga gaggaacagt tcaactccac ctaccgggtg     900
gtgtccgtgc tgaccgtgct gcaccaggat tggctgaacg gcaaagagta caagtgcaag     960
gtgtccaaca agggcctgcc ttccagcatc gaaaagacca tctccaaggc caagggccag    1020 cccccgggaac cccaggtgta cacactgcct ccaagccagg aagagatgac caagaaccag    1080
gtgtccctga cctgtctcgt gaaaggcttc taccctccg atatcgccgt ggaatgggag     1140
tccaacggcc agcctgagaa caactacaag accaccccc ctgtgctgga ctccgacggc     1200
tccttcttcc tgtactctcg gctgacagtg gacaagagcc ggtggcagga aggcaacgtg    1260
ttctcctgct ccgtgatgca cgaggccctg cacaaccact atacccagaa gtccctgtcc    1320
ctgtctctgg gaaag                                                     1335

<210> SEQ ID NO 114
<211> LENGTH: 1335
<212> TYPE: DNA
<213> ORGANISM: Artificial Sequence
<220> FEATURE:
<223> OTHER INFORMATION: humanized IgG4 chain 5F2.4 containing humanized
      VH4

<400> SEQUENCE: 114
gaagtgcagc tggtgcagtc tggcgccgaa gtgaagaaac tggcgcctc cgtgaaggtg       60 tcctgcaagg cttccggcta cacctttacc gactacaaca tggactgggt gcgacaggct    120
```

```
accggccagg gcctggaatg gatcggcgac atcaaccccca actacgagtc caccggctac    180
aaccagaagt tcaagggcag agccaccatg accgtgaaca agtccatctc caccgcctac    240
atggaactgt cctccctgcg gagcgaggac accgccgtgt actactgcgc cagagaggac    300
gaccacgacg cctttgctta ttggggccag ggcaccctcg tgaccgtgtc ctctgcttct    360
accaagggcc cctccgtgtt ccctctggcc ccttgctcca gatccacctc cgagtctacc    420
gccgctctgg gctgcctcgt gaaggactac ttccccgagc ccgtgacagt gtcttggaac    480
tctggcgccc tgacctccgg cgtgcacacc tttccagctg tgctgcagtc ctccggcctg    540
tactccctgt cctccgtcgt gactgtgccc tccagctctc tgggcaccaa gacctacacc    600
tgtaacgtgg accacaagcc ctccaacacc aaggtggaca gcgggtgga atctaagtac    660 ggccctccct gcctccttg cccagcccct gaatttctgg gcggaccag cgtgttcctg    720 ttcccccccaa agcccaagga caccctgatg atctccccgga ccccgaagt gacctgcgtg    780 gtggtggatg tgtcccagga agatcccgag gtgcagttca attggtacgt ggacggcgtg    840
gaagtgcaca acgccaagac caagcctaga gaggaacagt tcaactccac ctaccgggtg    900
gtgtccgtgc tgaccgtgct gcaccaggat tggctgaacg gcaaagagta caagtgcaag    960
gtgtccaaca agggcctgcc ttccagcatc gaaaagacca tctccaaggc caagggccag   1020 cccgggaac cccaggtgta cactgcct ccaagccagg aagagatgac caagaaccag   1080
gtgtccctga cctgtctcgt gaaaggcttc taccctccg atatcgccgt ggaatgggag   1140
tccaacggcc agcctgagaa caactacaag accaccccc ctgtgctgga ctccgacggc   1200
tccttcttcc tgtactctcg cctgaccgtg gataagtccc ggtggcagga aggcaacgtg   1260
ttctcctgct ccgtgatgca cgaggccctg cacaaccact atacccagaa gtccctgtcc   1320
ctgtctctgg gaaag                                                    1335
```

<210> SEQ ID NO 115
<211> LENGTH: 218
<212> TYPE: PRT
<213> ORGANISM: Artificial Sequence
<220> FEATURE:
<223> OTHER INFORMATION: humanized light chain 5F2.4 containing humanized VL1

<400> SEQUENCE: 115

```
Asp Asn Val Leu Thr Gln Ser Pro Asp Ser Leu Val Val Ser Leu Gly
1               5                   10                  15

Glu Arg Ala Thr Ile Ser Cys Arg Ala Ser Lys Ser Val Arg Thr Ser
            20                  25                  30

Gly Tyr Asn Tyr Met His Trp Tyr Gln Gln Lys Pro Gly Gln Pro Pro
        35                  40                  45

Lys Leu Leu Ile Tyr Leu Ala Ser Asn Leu Lys Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Gln Glu Glu Asp Ala Ala Thr Tyr Tyr Cys Gln His Ser Arg
                85                  90                  95

Glu Leu Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
```

```
                130                 135                 140
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
210                 215

<210> SEQ ID NO 116
<211> LENGTH: 218
<212> TYPE: PRT
<213> ORGANISM: Artificial Sequence
<220> FEATURE:
<223> OTHER INFORMATION: for humanized light chain 5F2.4 containing
      humanized VL2

<400> SEQUENCE: 116

Asp Asn Val Leu Thr Gln Ser Pro Asp Ser Leu Ala Val Ser Leu Gly
1               5                   10                  15

Glu Arg Ala Thr Ile Ser Cys Arg Ala Ser Lys Ser Val Arg Thr Ser
                20                  25                  30

Gly Tyr Asn Tyr Met His Trp Tyr Gln Gln Lys Pro Gly Gln Pro Pro
            35                  40                  45

Lys Leu Leu Ile Tyr Leu Ala Ser Asn Leu Lys Ser Gly Val Pro Ala
50                  55                  60

Arg Phe Ser Gly Ser Gly Ser Gly Thr Asp Phe Thr Leu Thr Ile Ser
65                  70                  75                  80

Ser Leu Gln Ala Glu Asp Ala Ala Thr Tyr Tyr Cys Gln His Ser Arg
                85                  90                  95

Glu Leu Pro Tyr Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
210                 215

<210> SEQ ID NO 117
<211> LENGTH: 218
<212> TYPE: PRT
<213> ORGANISM: Artificial Sequence
<220> FEATURE:
<223> OTHER INFORMATION: humanized light chain 5F2.4 containing
      humanized VL3
```

-continued

<400> SEQUENCE: 117

```
Asp Asn Val Leu Thr Gln Ser Pro Asp Ser Leu Ala Val Ser Leu Gly
1               5                   10                  15

Glu Arg Ala Thr Ile Ser Cys Arg Ala Ser Lys Ser Val Arg Thr Ser
            20                  25                  30

Gly Tyr Asn Tyr Met His Trp Tyr Gln Gln Lys Pro Gly Gln Pro Pro
        35                  40                  45

Lys Leu Leu Ile Tyr Leu Ala Ser Asn Leu Lys Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Ala Ala Thr Tyr Tyr Cys Gln His Ser Arg
                85                  90                  95

Glu Leu Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 118
<211> LENGTH: 218
<212> TYPE: PRT
<213> ORGANISM: Artificial Sequence
<220> FEATURE:
<223> OTHER INFORMATION: humanized light chain 5F2.4 containing humanized VL4

<400> SEQUENCE: 118

```
Asp Asn Val Leu Thr Gln Ser Pro Asp Ser Leu Ala Val Ser Leu Gly
1               5                   10                  15

Glu Arg Ala Thr Ile Asn Cys Arg Ala Ser Lys Ser Val Arg Thr Ser
            20                  25                  30

Gly Tyr Asn Tyr Met His Trp Tyr Gln Gln Lys Pro Gly Gln Pro Pro
        35                  40                  45

Lys Leu Leu Ile Tyr Leu Ala Ser Asn Leu Lys Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Ala Ala Thr Tyr Tyr Cys Gln His Ser Arg
                85                  90                  95

Glu Leu Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125
```

```
Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 119
<211> LENGTH: 445
<212> TYPE: PRT
<213> ORGANISM: Artificial Sequence
<220> FEATURE:
<223> OTHER INFORMATION: humanized IgG4 chain 5F2.4 containing humanized VH1

<400> SEQUENCE: 119

```
Glu Val Gln Leu Val Gln Ser Gly Ala Glu Leu Lys Lys Pro Gly Ala
1               5                   10                  15

Ser Val Lys Ile Ser Cys Lys Ala Ser Gly Tyr Thr Phe Thr Asp Tyr
            20                  25                  30

Asn Met Asp Trp Val Lys Gln Ala His Gly Gln Gly Leu Glu Trp Ile
        35                  40                  45

Gly Asp Ile Asn Pro Asn Tyr Glu Ser Thr Gly Tyr Asn Gln Lys Phe
    50                  55                  60

Lys Gly Arg Ala Thr Leu Thr Val Asp Lys Ser Ile Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Glu Asp Asp His Asp Ala Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270
```

```
Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 120
<211> LENGTH: 445
<212> TYPE: PRT
<213> ORGANISM: Artificial Sequence
<220> FEATURE:
<223> OTHER INFORMATION: for humanized IgG4 chain 5F2.4 containing
      humanized VH2

<400> SEQUENCE: 120

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Met Asp Trp Val Lys Gln Ala Thr Gly Gln Gly Leu Glu Trp Ile
        35                  40                  45

Gly Asp Ile Asn Pro Asn Tyr Glu Ser Thr Gly Tyr Asn Gln Lys Phe
    50                  55                  60

Lys Gly Arg Ala Thr Leu Thr Val Asp Lys Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Asp His Asp Ala Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
```

```
                180                 185                 190
Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
        210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 121
<211> LENGTH: 445
<212> TYPE: PRT
<213> ORGANISM: Artificial Sequence
<220> FEATURE:
<223> OTHER INFORMATION: humanized IgG4 chain 5F2.4 containing humanized
      VH3

<400> SEQUENCE: 121

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Met Asp Trp Val Arg Gln Ala Thr Gly Gln Gly Leu Glu Trp Ile
        35                  40                  45

Gly Asp Ile Asn Pro Asn Tyr Glu Ser Thr Gly Tyr Asn Gln Lys Phe
    50                  55                  60

Lys Gly Arg Ala Thr Leu Thr Val Asn Lys Ser Ile Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Glu Asp Asp His Asp Ala Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
            210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
            435                 440                 445

<210> SEQ ID NO 122
<211> LENGTH: 445
<212> TYPE: PRT
<213> ORGANISM: Artificial Sequence
<220> FEATURE:
<223> OTHER INFORMATION: humanized IgG4 chain 5F2.4 containing humanized
      VH4

<400> SEQUENCE: 122

Glu Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Asp Tyr
            20                  25                  30

Asn Met Asp Trp Val Arg Gln Ala Thr Gly Gln Gly Leu Glu Trp Ile
        35                  40                  45

Gly Asp Ile Asn Pro Asn Tyr Glu Ser Thr Gly Tyr Asn Gln Lys Phe
 50                  55                  60

Lys Gly Arg Ala Thr Met Thr Val Asn Lys Ser Ile Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Glu Asp Asp His Asp Ala Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380
```

```
Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
                420                 425                 430

His Tyr Thr Gln Lys Ser Leu Ser Leu Ser Leu Gly Lys
            435                 440                 445
```